US009737614B2

(12) United States Patent
Heller et al.

(10) Patent No.: US 9,737,614 B2
(45) Date of Patent: Aug. 22, 2017

(54) FUCOIDAN NANOGELS AND METHODS OF THEIR USE AND MANUFACTURE

(71) Applicant: Memorial Sloan Kettering Cancer Center, New York, NY (US)

(72) Inventors: Daniel A. Heller, New York, NY (US); Yosef Shamay, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 15/069,311

(22) Filed: Mar. 14, 2016

(65) Prior Publication Data

US 2016/0193349 A1  Jul. 7, 2016

Related U.S. Application Data

(62) Division of application No. 14/689,683, filed on Apr. 17, 2015.
(Continued)

(51) Int. Cl.
*A61K 9/00* (2006.01)
*A61K 47/48* (2006.01)
(Continued)

(52) U.S. Cl.
CPC ........ *A61K 47/4823* (2013.01); *A61K 9/0019* (2013.01); *A61K 9/06* (2013.01); *A61K 9/5146* (2013.01); *A61K 31/337* (2013.01); *A61K 31/4412* (2013.01); *A61K 31/704* (2013.01); *A61K 31/737* (2013.01); *A61K 41/0038* (2013.01); *A61K 47/48215* (2013.01); *A61K 47/48284* (2013.01); *A61K 47/48907* (2013.01); *A61K 49/00* (2013.01); *A61K 51/065* (2013.01)

(58) Field of Classification Search
CPC .................................................. A61K 47/4823
See application file for complete search history.

(56) References Cited

U.S. PATENT DOCUMENTS

2007/0238656 A1  10/2007 Harder et al.
2008/0166414 A1   7/2008 Hanes et al.
(Continued)

FOREIGN PATENT DOCUMENTS

WO  WO-2006/091180 A2  8/2006
WO  WO-2007/001448 A2  1/2007
(Continued)

OTHER PUBLICATIONS

Amano, H. et al., Angiotensin II Type 1A Receptor Signaling Facilitates Tumor Metastasis Formation Through P-Selectin-Mediated Interaction of Tumor Cells with Platelets and Endothelial Cells, American Journal of Pathology, 182(2):553-564 (2013).
(Continued)

Primary Examiner — Paul Dickinson
(74) Attorney, Agent, or Firm — Foley & Lardner LLP

(57) ABSTRACT

Described herein are polymeric drug-carrying nanogels that are capable of targeting to P-selectin for the treatment of cancer and other diseases and conditions associated with P-selectin. Furthermore, in certain embodiments, the nanogels presented here offer a drug release mechanism based on acidic pH in the microenvironment of a tumor, thereby providing improved treatment targeting capability and allowing use of lower drug doses, thereby reducing toxicity.

13 Claims, 66 Drawing Sheets

Related U.S. Application Data

(60) Provisional application No. 61/980,643, filed on Apr. 17, 2014.

(51) Int. Cl.

| | |
|---|---|
| A61K 31/704 | (2006.01) |
| A61K 31/337 | (2006.01) |
| A61K 49/00 | (2006.01) |
| A61K 41/00 | (2006.01) |
| A61K 31/737 | (2006.01) |
| A61K 9/51 | (2006.01) |
| A61K 9/06 | (2006.01) |
| A61K 31/4412 | (2006.01) |
| A61K 51/06 | (2006.01) |

(56) References Cited

U.S. PATENT DOCUMENTS

| | | |
|---|---|---|
| 2010/0204102 A1 | 8/2010 | Akiyoshi et al. |
| 2011/0085974 A1 | 4/2011 | Chung et al. |
| 2013/0030282 A1 | 1/2013 | Margel et al. |
| 2013/0039854 A1 | 2/2013 | Shih et al. |
| 2013/0046171 A1 | 2/2013 | Johansen et al. |
| 2014/0107062 A1 | 4/2014 | Shenoy |
| 2014/0220346 A1 | 8/2014 | Heller et al. |
| 2015/0328254 A1 | 11/2015 | Heller et al. |

FOREIGN PATENT DOCUMENTS

| | | |
|---|---|---|
| WO | WO-2013/148158 A1 | 10/2013 |
| WO | WO-2014037429 A2 | 3/2014 |
| WO | WO-2016/130546 A1 | 8/2016 |
| WO | WO-2016/153920 A1 | 9/2016 |

OTHER PUBLICATIONS

Babu, P. et al., Micellar aggregates and hydrogels from phosphonobile salts, Organic and Biomolecular Chemistry, 2:3695-3700 (2005).
Bonfanti, R. et al., PADGEM (GMP140) is a Component of Weibel-Palade Bodies of Human Endothelial Cells, Blood, 73(5):1109-1112 (1989).
Chen, Q. et al., Macrophage binding to receptor VCAM-1 transmits survival signals in breast cancer cells that invade the lungs, Cancer Cell, 20(4):538-549 (2011).
Chow, E.K. and Ho, D., Cancer Nanomedicine: From Drug Delivery to Imaging, Sci Transl Med, 5(216): 216vr4:1-12 (2013).
Da Silva, L.C. et al., Preparation and characterization of polysaccharide-based nanoparticles with anticoagulant activity, International Journal of Nanomedicine, 8:2975-2986 (2012).
Dan, M. et al., Binding, Transcytosis and Biodistribution of Anti-PECAM-1 Iron Oxide Nanoparticles for Brain-Targeted Delivery, PLOS ONE, 8(11):e81051:1-8 (2013).
De Geest, B. G. et al., Biodegradable microcapsules designed via 'click' chemistry, Chem. Commun., 2:190-192 (2008).
Erpenbeck, L. and Schon, M.P., Deadly allies: the fatal interplay between platelets and metastasizing cancer cells, Blood, 115(17):3427-3436 (2010).
Ferrari, M., Cancer Nanotechnology: Opportunities and Challenges, Nature Reviews Cancer, 5(3):161-167 (2005).
Fu, G-D. et al., Preparation of Fluorescent Organometallic Porphyrin Complex Nanogels of Controlled Molecular Structure via Reverse-Emulsion Click Chemistry, Macromol. Rapid Commun., 33:1523-1527 (2012).
Gong, L. et al., P-selectin-mediated platelet activation promotes adhesion of non-small cell lung carcinoma cells on vascular endothelial cells under flow, Mol Med Rep, 5(4):935-942 (2012).
Grodzinski, P. and Farrell, D., Future Opportunities in Cancer Nanotechnology—NCI Strategic Workshop Report, American Association for Cancer Research, 74(5):1307-1310 (2014).
Gunngingham, S.P. et al., The angiogenic factor thymidine phosphorylase up-regulates the cell adhesion molecule P-selectin in human vascular endothelial cells and is associated with P-selectin expression in breast cancers, J Pathol, 212(3):335-344 (2007).
Hallahan, D.E. and Virudachalam, S., Accumulation of P-selectin in the Lumen of Irradiated Blood Vessels, 152:6-13 (1999).
Hallahan, D.E. et al., X-Ray-induced P-selectin Localization to the Lumen of Tumor Blood Vessels, Cancer Res, 58:5216-5220 (1998).
Hamidi, S. et al., Fucodian promotes early step of cardiac differentiation from human embryonic stem cells and long-term maintenance of beating areas. Tissue Engineering: Part A, 20(7-8):1285-1294 (2014).
Heldin, C.H. et al., High Interstitial Fluid Pressure—An Obstacle in Cancer Therapy, Nat Rev Cancer, 4:806-813 (2004).
Heller, D. A. et al., Modular 'Click-in-Emulsion' Bone-Targeted Nanogels, Adv. Mater. 25:1449-1454 (2013).
Hemmerlein, B. et al., Expression of VCAM-1, ICAM-1, E- and P-selectin and tumour-associated macrophages in renal cell carcinoma, Histapathology 37:78-83 (2000).
Hrkach, J. et al., Nanomedicine—Preclinical Development and Clinical Translation of a PSMA-Targeted Docetaxel Nanoparticle with a Differentiated Pharmacological Profile, Sci Transl Med, 4(128):128ra39 (2012).
Huan, M. et al., In vitro and in vivo antitumor activity of a novel ph-activated polymeric drug delivery system for doxorubicin, PLOS One, 7(9):e44116 (2012).
International Search Report for PCT/US2013/073198, dated Jul. 11, 2014 (5 pages).
International Search Report, PCT/US2015/026362, 4 pages, Jul. 10, 2015.
Iwamura, T. et al., P-selectin Expression in a Metastatic Pancreatic Tumor Cell Line (SUIT-2), Cancer Res, 57:1206-1212 (1997).
Kabanov, A. V. and Vinogradov, S. V., Nanogels as Pharmaceutical Carriers: Finite Networks of Infinite Capabilities, Agnew. Chem. Int. Ed. 48:5418-5429, (2009).
Kansas, G. S., Selectins and Their Ligands: Current Concepts and Controversies, Blood, 88(9):3259-3287 (1996).
Lammers, T. et al., Drug targeting to tumors: Principles, pitfalls and (pre-) clinical progress, J Control Release, 161:175-187 (2012).
Laubli, H. and Borsig, L., Selectins promote tumor metastasis, Seminars in Cancer Biology, 20:169-177 (2010).
Lee, K. W. et al., Doxorubicin loading fucoidan acetate nanoparticles for immune and chemotherapy in cancer treatment, Carbohydrate Polymers, 94:850-856 (2013).
Liu, Y. et al., Multifunctional pH-sensitive polymeric nanoparticles for theranostics evaluated experimentally in cancer, Nancoscale, 6:3231-3242 (2014).
Mak, W. et al., Fucoidan from new Zealand Undaraia pinnatifida: Monthly variations and determination of antioxidant activities, Carbohydrate Polymers 95:606-614 (2013).
Matsumura, Y. and Maeda, H., A New Concept for Macromolecular Therapeutics in Cancer Chemotherapy: Mechanism of Tumoritropic Accumulation of Proteins and the Antitumor Agent Smancs, Cancer Research, 461:6387-6392 (1986).
Parodi, A. et al., Biomimetic functionalization with leukocyte membranes imparts cell like functions to synthetic particles, Nature Nanotechnology, 8(1):61-68 (2013).
Prabhakar, U. et al., Challenges and key considerations of the enhanced permeability and retention (EPR) effect for nanomedicine drug delivery in oncology, Cancer Research, 73(8):2412-2417 (2013).
Prasanna, A. et al., Exploiting sensitization windows of opportunity in hyper and hypo-fractionated radiation therapy, J Thorac Dis, 6(4):287-302 (2014).
Righi, L. et al., Role of CD31/Platelet Endothelial Cell Adhesion Molecule-1 Expression in in Vitro and in Vivo Growth and Differentiation of Human Breast Cancer Cells, American Journal of Pathology, 162(4):1163-1174 (2003).
Rosette, C. et al., Role of ICAM1 in invasion of human breast cancer cells, Carcinogenesis, 26(5):943-950 (2005).
Rouzet, F., et al., Radiolabeled Fucoidan as a P-Selectin Targeting Agent for In Vivo Imaging of Platelet-Rich Thrombus and Endothelial Activation, J Nucl Med, 52(9):1433-1440 (2011).

(56) References Cited

OTHER PUBLICATIONS

Schroedar, A. et al., Treating metastatic cancer with nanotechnology, Nature Review Cancer, 12:39-50 (2011).
Varghese, O. P. et al., In Situ Cross-Linkable High Molecular Weight Hyaluronan-Bisphosphonate Conjugate for Localized Delivery and Cell-Specific Targeting: A Hydrogel Linked Prodrug Approach, J. Am. Chem. Soc. 131:8781-8783, (2009).
Wang, G. et al., Bisphosphonate-decorated lipid nanoparticles designed as drug carriers for bone diseases, J. Biomed. Mater. Res. Part A: 100A(3):684-693 (2012).
Written Opinion for PCT/US2013/073198, dated Jul. 11, 2014 (9 pages).
Written Opinion, PCT/US2015/026362, 13 pages, Jul. 10, 2015.
Yang, X. et al., Direct 'Click' Synthesis of Hybrid Bisphosphonate-Hyaluronic Acid Hydrogel in Aqueous Solution for Biomineralization, Chemistry of Materials, 24(9):1690-1697 (2012).
Yuan, W. et al., Effect of Surface Charge of Immortalized Mouse Cerebral Endothelial Cell Monolayer on Transport of Charged Solutes, Annals Biomedical Engineering, 38(4):1463-1472 (2010).
Zhang, Z. et al, Fucoidan extract enhances the anti-cancer activity of chemotherapeutic agents in MDA-MB-231 and MCF-7 breast cancer cells, Marine Drugs, 11:81-98 (2013).
Zhu, J-L. et al., Amphiphilic star-block copolymers and supramolecular transformation of nanogel-like micelles to nanovesicles, Chem. Commun., 47:12849-12851 (2011).
Zitzmann et al, Arginine-Glycine-Aspartic Acid (RGD)-Peptide Binds to Both Tumor-Endothelial Cells in Vivo, Cancer Research 62:5139-5143 (2002).
Bayzylińska, U. et al., Polymeric nanocapsules and nanospheres for encapsulation and long sustained release of hydrophobic cyanine-type photosensitizer, Colloids and Surfaces A: Physicachemical and Engineering Aspects, 442:42-49 (2014).
Cole, A. J. et al., Magnetic brain tumor targeting and biodistribution of long-circulating PEG-modified, cross-linked starch-coated iron oxide nanoparticles, Biomaterials, 32:6291-6301 (2011).
Dolman, M.E.M. et al., Drug targeting to the kidney: Advances in the active targeting of therapeutics to proximal tubular cells, Advanced Drug Delivery Reviews, 62(14):1344-1357 (2010).
Han, H. et al., Camptothecin-conjugated biodegradable prodrug micelles for theranostic near-infrared fluorescent imaging and intracellular drug release, Journal of Controlled Release, vol. 213 (2015).
Hultman, K. L. et al., Magnetic Resonance Imaging of Major Histocompatibility Class II Expression in the Renal Medulla Using Immunotargeted Superparamagnetic Iron Oxide Nanoparticles, 2(3):477-484 (2008).
Illum, L. et al., The Organ Distribution and Circulation Time of Intravenously Injected Colloidal Carriers Sterically Stabilized with a Blockopolymer—Poloxamine 908, Life Science, 40(4):367-374 (1987).
International Search Report, PCT/US2016/017153, 5 pages, Apr. 8, 2015.
International Search Report, PCT/US2016/022879, 7 pages, May 6, 2016.
Kumar Piyush et al., IR 820 dye encapsulated in polycaprolactone glycol chitosan: Poloxamer blend nanoparticles for photo immunotherapy for breast cancer, Materials Science and Engineering C, 57:321-327 (2015).
Kumar, A. et al., Multifunctional magnetic nanoparticles for targeted delivery, Nanomedicine: Nanotechnology, Biology and Medicine 6:64-69 (2010).
Li, Y-P et al., PEGylated PLGA nanoparticles as protein carriers: synthesis, preparation and biodistribution in rats, Journal of Controlled Release, 71(2):203-211 (2001).
Liu, J. et al., Passive Tumor Targeting of Renal-Clearable Luminescent Gold Nanoparticles: Long Tumor Retention and Fast Normal Tissue Clearance, J. Am. Chem. Soc., 135(13):4978-4981 (2013).
Lv Yalin et al.., An activatable theranostic prodrug for target cancer therapy and imaging, Nanomedicine: Nanotechnology, Biology and Medicine, 12:2:479 (2016).
Shenoy, D. et al., Poly(Ethylene Oxide)—Modified Poly(β-Amino Ester) Nanoparticles as a pH-Sensitive System for Tumor-Targeted Delivery of Hydrophobic Drugs: Part 2. In Vivo Distribution and Tumor Localization Studies, Pharmaceutical Research, 22(12):2107-2114 (2005).
Written Opinion, PCT/US2016/017153, 10 pages, Apr. 8, 2016.
Written Opinion, PCT/US2016/022879, 8 pages, May 6, 2016.
Da Silva, LC et al., Preparation and characterization of polysaccharide-based nanoparticles with anticoagulant activity, International Journal of Nanomedicine, 8:2975-2986 (2012).
Jiang, Y. et al., Click hydrogels, microgels and nanogels: Emerging platforms for drug delivery and tissue engineering, Biomaterials, 35:4969-4985 (2014).
Kansas, G.S., Selectins and Their Ligands: Current Concepts and Controversies, Blood, 88(9):3259-3287 (1996).
Perez-Medina, C. et al., A Modular Labeling Strategy for In Vivo PET and Near-Infrared Fluorescence Imaging of Nanoparticle Tumor Targeting, The Journal of Nuclear Medicine, 55(10):1706-1711 (2014).

LOADING EFFICIENCY
91% BY UV-VIS

FUCOIDAN NANOGELS AND METHODS OF THEIR USE AND MANUFACTURE

CROSS REFERENCE TO RELATED APPLICATION

This application is a divisional of U.S. application Ser. No. 14/689,683, filed on Apr. 17, 2015, which claims the benefit of U.S. Application Ser. No. 61/980,643 filed on Apr. 17, 2014, the disclosures of which are is. hereby incorporated by reference in their entireties.

GOVERNMENT SUPPORT

This invention was made with government support under grant number HD075698 awarded by the National Institutes of Health. The government has certain rights in the invention.

TECHNICAL FIELD

This invention relates generally to nanogels and methods of their manufacture and therapeutic use. In particular embodiments, the invention relates to polymeric fucoidan-based nanogel vehicles for the treatment of cancer and other diseases associated with P-selectin.

BACKGROUND

Nanogels—porous nanoscale hydrogel networks—are a class of nanomaterials with tunable chemical properties that facilitate targeting and delivery to specific tissues. They are intrinsically porous and can be loaded with small drugs or macromolecules by physical entrapment, covalent conjugation or controlled self-assembly. The porosity of nanogels protect the drugs they carry from degradation and environmental hazards; hence, nanogels can be used as drug delivery agents and contrast agents for medical imaging.

Fucoidans are a class of sulfated, fucose-rich polymers that can be found, for example, in brown macroalgae. Fucoidans have been reported to have anticoagulant, antiviral, anti-inflammatory, and anticancer activities, as well as high affinity to P-selectin. P-selectin is an inflammatory cell adhesion molecule responsible for leukocyte recruitment and platelet binding. It is expressed constitutively in endothelial cells where it is stored in intracellular granules (Weibel-Palade bodies). Upon endothelial activation with endogenous cytokines or exogenous stimuli such as ionizing radiation, P-selectin translocates to the cell membrane and into the lumen of blood vessels. P-selectin expression has been found to increase significantly in the vasculature of human lung, breast, and kidney cancers. P-selectin has been shown to facilitate the process of metastasis by coordinating the interaction between cancer cells, activated platelets and activated endothelial cells.

It has been unexpectedly found that P-selectin is expressed in stroma and cancer cells in may human tumors, as well as in vasculature. Only one previous report describes P-selectin expression in cancer cells—a metastatic pancreatic tumor cell line. The phenomenon of tumor cell expression of endothelial-specific adhesion molecules such as ICAM-1, VCAM-1, CD31/PECAM-1 and VE-cadherin has been applied to various types of cancer cells and associated with increased metastasis and poor patient prognosis.

The direct administration of fucoidan as a treatment for tumors or metastases can be ineffective, due to toxicity limitations and lack of drug targeting. Disseminated tumors are poorly accessible to nanoscale drug delivery systems due to the vascular barrier, which prevents sufficient extravasation at the tumor site. Strategies to target leaky vasculature via the enhanced permeability and retention (EPR) effect have shown little efficacy on avascular tumors and small metastases.

The clinical potential of nanomedicines has not yet been fulfilled in part due to the endothelium barrier which limits the extravasation of nanoparticles from the circulation into solid tumors. Passive targeting mechanisms such as the enhanced permeability and retention "EPR" effect show preclinical efficacy. Yet the effect is less effective in small tumors and metastases. Endothelial cells (EC) in the neovasculature are promising targets due to their genetic stability and exposure to the circulation. Nanoparticle drug carriers targeting the neovasculature are currently under clinical development, however, targeted delivery of therapeutic agents to micro-metastases or tumors lacking neovasculature remains an enduring challenge.

A nanogel containing fucoidan has been produced by chemical acetylation of the hydroxyl groups of fucoidan, rendering it amphipilic and able to form nanoparticles loaded with doxorubicin (Lee et al., *Carbohydrate Polymers* 95 (2013) 606-614). However, by acetylating the hydroxyl groups of fucose, specific affinity of the drug-containing nanogel to P-selectin is eliminated, thereby adversely affecting the ability of the nanogel to target cancer and other diseases associated with P-selectin.

There exists a need for a fucoidan-based nanogel that has a specific affinity to P-selectin to treat cancer and other diseases and conditions associated with P-selectin.

SUMMARY OF THE INVENTION

Described herein are polymeric drug-carrying nanogels that are capable of targeting to P-selectin and, therefore, are useful in the treatment of cancer and other diseases and conditions associated with P-selectin. Without wishing to be bound to any particular theory, specific affinity to P-selectin requires both free hydroxyls and a proximate negative charge. Thus, presented herein are nanogels having hydroxyls and sulfates that are free for targeting to P-selectin. Furthermore, in certain embodiments, the nanogels presented here offer a drug release mechanism based on acidic pH in the microenvironment of a tumor, thereby providing improved treatment targeting capability and allowing use of lower drug doses, thereby reducing toxicity.

P-selectin is a new target for drug delivery in various cancers and contributes both at the tissue level and the cellular level. Since P-selectin is highly involved in inflammatory processes, it is useful for inflammatory diseases such as arthritis and atherosclerosis, which also involve P-selectin on endothelial cells. P-selectin is a cell adhesion molecule known to facilitate metastasis which is expressed in the vasculature of many human tumors. A delivery nanoparticle platform was developed using an algae-derived polysaccharide with intrinsic nanomolar affinity to P-selectin. The nanoparticles target primary and metastatic tumors to impart a significant anti-tumor activity compared to untargeted nanoparticles encapsulating chemotherapies. Single-dose administration of an encapsulated reversible MEK inhibitor results in prolonged inhibition of ERK phosphorylation and increased apoptosis at the tumor site. Additionally, ionizing radiation-induced P-selectin expression guides the targeted nanoparticles to the tumor site, demonstrating a potential strategy to target disparate drug classes to almost any tumor.

P-selectin was identified as a useful target for drug delivery and was used in a set of in vivo and in vitro models to explore its anti-tumor effectiveness, with multiple applications such as targeting aggressive primary and metastatic tumors using irreversible chemotherapies and reversible kinase inhibitor.

In certain embodiments, the nanogels described herein present fucoidan on their surface, specifically targeting P-selectin on activated platelets and activated endothelium. The fucoidan on the surface of the nanoparticles making up the nanogel have free hydroxyl moieties and free sulfate moieties. The nanoparticles release the drug moieties they contain in the acidic tumor microenvironment and lysosomes. The fucoidan also appears to act as an immunomodulator, likely inducing an immune response against the tumor.

In a specific embodiment, a fucoidan-based nanogel is presented that delivers doxorubicin and releases it via pH-sensitive degradation of a hydrazone bond. The doxorubicin is chemically conjugated to polyethylene glycol (PEG), but is only electrostatically bound to the anionic polymer fucoidan. In other embodiments, other cationic drugs may be used, for example, vincristine. The particle size and charge can be modified according to the intended use.

In other specific embodiments described herein, nanogels are synthesized by non-covalent assembly of fucoidan with a hydrophobic drug. Nanoparticle-drug assemblies synthesized using this method include, for example, particles encapsulating one or more of paclitaxel, MEK162, and ispinesib.

Also, in certain embodiments, the invention encompasses methods of treatment of disease associated with P-selectin using the compositions described herein. For example, the compositions may be used in the treatment of malignant neoplasms including carcinomas, sarcomas, lymphomas, and leukemia. Furthermore, the compositions may be used in other P-selectin-associated diseases such as sickle cell disease, arterial thrombosis, rheumatoid arthritis, ischemia, and reperfusion. Combination therapies are contemplated herein. Also, the use of compositions described herein with radiotherapy for improved P-selectin targeting and activity is contemplated.

In one aspect, the invention is directed to a polymeric nanogel with affinity to P-selectin, the nanogel comprises: (i) a sulfated polymer species comprising free hydroxyl moieties and sulfate moieties capable of targeting to P-selectin; and (ii) a drug.

In certain embodiments, the sulfated polymer species is a sulfated polysaccharide and/or protein. In certain embodiments, the drug is a cationic drug.

In certain embodiments, the sulfated polymer species is a fucoidan. In certain embodiments, the fucoidan is a sulfated polysaccharide comprising sulfated ester moieties of fucose.

In certain embodiments, the nanogel comprises nanoparticles that have a core comprising albumin and a surface comprising fucoidan. In certain embodiments, the nanogel comprises polyethylene glycol (PEG), wherein the drug is conjugated to the polyethylene glycol via hydrozone linkages.

In certain embodiments, the drug is not chemically conjugated to the sulfated polymer species, but is electrostatically bound to the sulfated polymer species. In certain embodiments, the sulfated polymer species is a fucoidan.

In certain embodiments, the drug is doxorubicin (DOX) {(7S,9S)-7-[(2R,4S,5S,5S,6S)-4-amino-5-hydroxy-6-methyloxan-2-yl]oxy-6,9,11-trihydroxy-9-(2-hydroxyacetyl)-4-methoxy-8,10-dihydro-7H-tetracene-5,12-dione} (trade name Adriamycin).

In certain embodiments, the drug is vincristine {(3aR,3a1R,4R,5S,5aR,10bR)-methyl 4-acetoxy-3a-ethyl-9-((5S,7S,9S)-5-ethyl-5-hydroxy-9-(methoxycarbonyl)-2,4,5,6,7,8,9,10-octahydro-1H-3,7-methano[1]azacycloundecino[5,4-b]indol-9-yl)-6-formyl-5-hydroxy-8-methoxy-3a,3a1,4,5,5a,6,11,12-octahydro-1H-indolizino[8,1-cd]carbazole-5-carboxylate}.

In certain embodiments, the cationic drug comprises one or more members selected from the group consisting of: DOX, vincristine, paclitaxel{(2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate}, MEK162 {6-(4-bromo-2-fluoroanilino)-7-fluoro-N-(2-hydroxyethoxy)-3-methylbenzimidazole-5-carboxamide}, ispinesib {N-(3-aminopropyl)-N-[(1R)-1-(3-benzyl-7-chloro-4-oxoquinazolin-2-yl)-2-methylpropyl]-4-methylbenzamide}, daunorubicin (daunomycin) {(8S,10S)-8-acetyl-10-[(2S,4S,5S,6S)-4-amino-5-hydroxy-6-methyl-oxan-2-yl]oxy-6,8,11-trihydroxy-1-methoxy-9,10-dihydro-7H-tetracene-5,12-dione}, epirubicin {(8R,10S)-10-((2S,4S,5R,6S)-4-amino-5-hydroxy-6-methyltetrahydro-2H-pyran-2-yl)-6,8,11-trihydroxy-8-(2-hydroxyacetyl)-1-methoxy-7,8,9,10-tetrahydrotetracene-5,12-dione}, idarubicin {(1S,3S)-3-acetyl-3,5,12-trihydroxy-6,11-dioxo-1,2,3,4,6,11-hexahydrotetracen-1-yl 3-amino-2,3,6-trideoxy-α-L-lyxo-hexopyranoside}, valrubicin {2-oxo-2-[(2S,4S)-2,5,12-trihydroxy-7-methoxy-6,11-dioxo-4-({2,3,6-trideoxy-3-[(trifluoroacetyl)amino]hexopyranosyl}oxy)-1,2,3,4,6,11-hexahydrotetracen-2-yl]ethyl pentanoate}, mitoxantrone {1,4-dihydroxy-5,8-bis[2-(2-hydroxyethylamino)ethylamino]-anthracene-9,10-dione}, vinblastine {dimethyl (2β,3β,4β,5α,12β,19α)-15-[(5S,9S)-5-ethyl-5-hydroxy-9-(methoxycarbonyl)-1,4,5,6,7,8,9,10-octahydro-2H-3,7-methanoazacycloundecino[5,4-b]indol-9-yl]-3-hydroxy-16-methoxy-1-methyl-6,7-didehydroaspidospermidine-3,4-dicarboxylate}, vindesine {methyl (5S,7S,9S)-9-[(2β,3β,4β,5α,12β,19α)-3-(aminocarbonyl)-3,4-dihydroxy-16-methoxy-1-methyl-6,7-didehydroaspidospermidin-15-yl]-5-ethyl-5-hydroxy-1,4,5,6,7,8,9,10-octahydro-2H-3,7-methanoazacycloundecino[5,4-b]indole-9-carboxylate}, vinorelbine {4-(acetyloxy)-6,7-didehydro-15-((2R,6R,8S)-4-ethyl-1,3,6,7,8,9-hexahydro-8-(methoxycarbonyl)-2,6-methano-2H-azecino(4,3-b)indol-8-yl)-3-hydroxy-16-methoxy-1-methyl-methyl ester}, bleomycin {(3-{[(2'-{(5S,8,S9S,10R,13S)-15-{6-amino-2-[(1S)-3-amino-1-{[(2S)-2,3-diamino-3-oxopropyl]amino}-3-oxopropyl]-5-methylpyrimidin-4-yl}-13-[{[(2R,3S,4S,5S,6S)-3-{[(2R,3S,4S,5R,6R)-4-(carbamoyloxy)-3,5-dihydroxy-6-(hydroxymethyl)tetrahydro-2H-pyran-2-yl]oxy}-4,5-dihydroxy-6-(hydroxymethyl)tetrahydro-2H-pyran-2-yl]oxy}(1H-imidazol-5-yl)methyl]-9-hydroxy-5-[(1R)-1-hydroxyethyl]-8,10-dimethyl-4,7,12,15-tetraoxo-3,6,11,14-tetraazapentadec-1-yl}-2,4'-bi-1,3-thiazol-4-yl)carbonyl]amino}propyl)(dimethyl)sulfonium}, actinomycin D (dactinomycin) {2-Amino-N,N'-bis[(6S,9R,10S,13R,18aS)-6,13-diisopropyl-2, 5,9-trimethyl-1,4,7,11,14-pentaoxohexadecahydro-1H-pyrrolo[2,1-i][1,4,7,10,13]oxatetraazacyclohexadecin-10-yl]-4,6-dimethyl-3-oxo-3H-phenoxazine-1,9-dicarboxamide}, sorafenib {4-[4-[[4-chloro-3-(trifluoromethyl)phenyl]carbamoylamino]phenoxy]-N-methyl-pyridine-2-carboxamide}, camptothecin {(S)-4-ethyl-4-hydroxy-1H-pyrano[3',4':6,7]indolizino[1,2-b]quinoline-3,14-(4H,12H)-dione}, topotecan {(S)-10-[(dimethylamino)methyl]-4-ethyl-4,9-dihydroxy-1H-pyrano[3',4':6,7]indolizino[1,2-b]quinoline-3,14(4H,12H)-dione monohydrochloride}, and irinotecan {(S)-

4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate}.

In certain embodiments, the nanogel comprises fucoidan and DOX-PEG-DOX constructs. In certain embodiments, the nanogel comprises fucoidan on the surface of nanoparticles of the nanogel. In certain embodiments, the nanogel comprises particles having an average particle diameter of from about 20 nm to about 400 nm (e.g., from about 100 nm to about 200 nm, or from about 150 nm to about 170 nm).

In certain embodiments, the nanogel further comprises a fluorophore. In certain embodiments, the fluorophore is a near infra-red dye. In certain embodiments, the near infrared dye is IR783 {2-[2-[2-Chloro-3-[2-[1,3-dihydro-3,3-dimethyl-1-(4-sulfobutyl)-2H-indol-2-ylidene]-ethylidene]-1-cyclohexen-1-yl]-ethenyl]-3,3-dimethyl-1-(4-sulfobutyl)-3H-indolium hydroxide, inner salt sodium salt}.

In certain embodiments, the nanogel is a pharmaceutical composition. In certain embodiments, the nanogel is pharmaceutically acceptable.

In another aspect, the invention is directed to a method of treating a P-selectin associated disease, the method comprising a step of administering to a subject in need of treatment a formulation comprising a polymeric nanogel with affinity to P-selectin, the nanogel comprising: (i) a sulfated polymer species comprising free hydroxyl moieties and sulfate moieties capable of targeting to P-selectin; and (ii) a drug; wherein the nanogel binds to P-selectin and translocates an active endothelial barrier. In certain embodiments, the sulfated polymer species is a sulfated polysaccharide and/or protein. In certain embodiments, the drug is a cationic drug.

In certain embodiments, the subject is human. In certain embodiments, the formulation is a therapeutic agent.

In certain embodiments, the P-selectin associated disease is a member selected from the group consisting of carcinoma, sarcoma, lymphoma, leukemia, sickle cell disease, arterial thrombosis, rheumatoid arthritis, ischemia, and reperfusion.

In certain embodiments, the method comprises administering a radiotherapeutic, wherein the nanogel provides improved P-selectin targeting and activity.

In certain embodiments, the step of administering the nanogel results in targeted delivery of the drug to P-selectin. In certain embodiments, upon delivery of the drug to P-selectin, a local environment having an acidic pH causes release of the drug from the nanogel. In certain embodiments, the nanogel comprises PEG and the local acidic pH environment results in breakage of hydrozone linkages between the PEG and the drug.

In another aspect, the invention is directed to a method for manufacturing a nanogel comprising contacting fucoidan and a drug-PEG construct in the presence of a salt to form hydrogel aggregates, and agitating the hydrogel aggregates to form nanoparticles.

In certain embodiments, the drug-PEG construct is DOX-PEG-DOX. In certain embodiments, the salt is a phosphonobile salt (PBS). In certain embodiments, the agitating includes sonicating the hydrogel aggregates.

In another aspect, the invention is directed to a method for manufacturing a nanogel comprising contacting albumin, fucoidan, and sorafenib in an aqueous salt solution to form hydrogel aggregates, and agitating the hydrogel aggregates to form nanoparticles. In certain embodiments, the albumin is Human Serum Albumin. In certain embodiments, the salt solution is a phosphonobile salt (PBS). In certain embodiments, agitating includes sonicating the hydrogel aggregates.

In another aspect, the invention is directed to a method for manufacturing a nanogel comprising contacting fucoidan and paclitaxel in an aqueous solution to form hydrogel aggregates, and agitating the hydrogel aggregates to form nanoparticles.

In certain embodiments, agitating includes sonicating the hydrogel aggregates.

In another aspect, the invention is directed to a polymeric fucoidan-based nanogel with affinity to P-selectin, the nanogel comprising a non-covalent assembly of fucoidan and a hydrophobic drug.

In certain embodiments, the hydrophobic drug comprises one or more members selected from the group consisting of paclitaxel {(2α,4α,5β,7β,10β,13α)-4,10-bis(acetyloxy)-13-{[(2R,3S)-3-(benzoylamino)-2-hydroxy-3-phenylpropanoyl]oxy}-1,7-dihydroxy-9-oxo-5,20-epoxytax-11-en-2-yl benzoate}, docetaxel {1,7β,10β-trihydroxy-9-oxo-5,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}}, Camptothecin {(S)-4-ethyl-4-hydroxy-1H-pyrano[3',4':6,7]indolizino[1,2-b]quinoline-3,14-(4H,12H)-dione}, MEK162 {6-(4-bromo-2-fluoroanilino)-7-fluoro-N-(2-hydroxyethoxy)-3-methylbenzimidazole-5-carboxamide}, sorafenib {4-[4-[[4-chloro-3-(trifluoromethyl)phenyl]carbamoylamino]phenoxy]-N-methyl-pyridine-2-carboxamide}, ispinesib {N-(3-aminopropyl)-N-[(1R)-1-(3-benzyl-7-chloro-4-oxoquinazolin-2-yl)-2-methylpropyl]-4-methylbenzamide}, LY294002 {2-Morpholin-4-yl-8-phenylchromen-4-one}, Selumetinib {6-(4-bromo-2-chloroanilino)-7-fluoro-N-(2-hydroxyethoxy)-3-methylbenzimidazole-5-carboxamide}, PD184352 {2-(2-chloro-4-iodoanilino)-N-(cyclopropylmethoxy)-3,4-difluorobenzamide}, 5-fluorouracil {5-fluoro-1H,3H-pyrimidine-2,4-dione}, Cyclophosphamide {(RS)—N,N-bis(2-chloroethyl)-1,3,2-oxazaphosphinan-2-amine 2-oxide}, Atorvastatin {(3R,5R)-7-[2-(4-fluorophenyl)-3-phenyl-4-(phenylcarbamoyl)-5-propan-2-ylpyrrol-1-yl]-3,5-dihydroxyheptanoic acid}, Lovastatin {(1S,3R,7S,8S,8aR)-8-{2-[(2R,4R)-4-hydroxy-6-oxooxan-2-yl]ethyl}-3,7-dimethyl-1,2,3,7,8,8a-hexahydronaphthalen-1-yl (2S)-2-methylbutanoate}, etoposide {4'-Demethyl-epipodophyllotoxin 9-[4,6-O—(R)-ethylidene-beta-D-glucopyranoside], 4'-(dihydrogen phosphate)}, dexamethasone {(8S,9R,10S,11S,13S,14S,16R,17R)-9-Fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one}, gemcitabine {4-amino-1-(2-deoxy-2,2-difluoro-β-D-erythro-pentofuranosyl)pyrimidin-2(1H)-on}, Rapamycin (Sirolimus) {(3S,6R,7E,9R,10R,12R,14S,15E,17E,19E,21 S,23S, 26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29 (4H,6H,31H)-pentone}, and methotrexate {(2S)-2-[(4-{[(2,4-diaminopteridin-6-yl)methyl](methyl)amino}benzoyl) amino]pentanedioic acid}.

Other features, objects, and advantages of the present invention are apparent in the detailed description and claims that follow. It should be understood, however, that the detailed description and claims, while indicating embodiments of the present invention, are given by way of illustration only, not limitation. Various changes and modifications within the scope of the invention will become apparent to those skilled in the art.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Amino Acid": As used herein, the term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is ad-amino acid; in some embodiments, an amino acid is an 1-amino acid. "Standard amino acid" refers to any of the twenty standard 1-amino acids commonly found in naturally occurring peptides.

"Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

"Antibody polypeptide": As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In particular embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immunoglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity.

"Antigen": As used herein, the term "antigen" is a molecule or entity to which an antibody binds. In some embodiments, an antigen is or comprises a polypeptide or portion thereof. In some embodiments, an antigen is a portion of an infectious agent that is recognized by antibodies. In some embodiments, an antigen is an agent that elicits an immune response; and/or (ii) an agent that is bound by a T cell receptor (e.g., when presented by an MHC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in some embodiments other than a biologic polymer (e.g., other than a nucleic acid or amino acid polymer)] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated moieties are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example, streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, electrostatic interactions, hydrogen bonding, affinity, metal coordination, physical adsorption, host-guest interactions, hydrophobic interactions, pi stacking interactions, van der Waals interactions, magnetic interactions, electrostatic interactions, dipole-dipole interactions, etc.

As used herein, for example, within the claims, the term "ligand" encompasses moieties that are associated with another entity, such as a nanogel polymer, for example. Thus, a ligand of a nanogel polymer can be chemically bound to, physically attached to, or physically entrapped within, the nanogel polymer, for example.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In some embodiments, biodegradable materials are enzymatically broken down. Alternatively or additionally, in some embodiments, biodegradable materials are broken down by hydrolysis. In some embodiments, biodegradable polymeric materials break down into their component polymers. In some embodiments, breakdown of biodegradable materials (including, for example, biodegradable polymeric materials) includes hydrolysis of ester bonds. In some embodiments, breakdown of materials (including, for example, biodegradable polymeric materials) includes cleavage of urethane linkages.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin. In some embodiments, the composition described herein is a carrier.

"Combination Therapy": As used herein, the term "combination therapy", refers to those situations in which two or more different pharmaceutical agents for the treatment of disease are administered in overlapping regimens so that the subject is simultaneously exposed to at least two agents. In some embodiments, the different agents are administered simultaneously. In some embodiments, the administration of one agent overlaps the administration of at least one other agent. In some embodiments, the different agents are administered sequentially such that the agents have simultaneous biologically activity with in a subject.

"Hydrolytically degradable": As used herein, "hydrolytically degradable" materials are those that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Pharmaceutically acceptable": The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

"Pharmaceutical composition": As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation: topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

"Protein": As used herein, the term "protein" refers to a polypeptide (i.e., a string of at least 3-5 amino acids linked to one another by peptide bonds). Proteins may include moieties other than amino acids (e.g., may be glycoproteins, proteoglycans, etc.) and/or may be otherwise processed or modified. In some embodiments "protein" can be a complete polypeptide as produced by and/or active in a cell (with or without a signal sequence); in some embodiments, a "protein" is or comprises a characteristic portion such as a polypeptide as produced by and/or active in a cell. In some embodiments, a protein includes more than one polypeptide chain. For example, polypeptide chains may be linked by one or more disulfide bonds or associated by other means. In some embodiments, proteins or polypeptides as described herein may contain L amino acids, D-amino acids, or both, and/or may contain any of a variety of amino acid modifications or analogs known in the art. Useful modifications include, e.g., terminal acetylation, amidation, methylation, etc. In some embodiments, proteins or polypeptides may comprise natural amino acids, non-natural amino acids, synthetic amino acids, and/or combinations thereof. In some embodiments, proteins are or comprise antibodies, antibody polypeptides, antibody fragments, biologically active portions thereof, and/or characteristic portions thereof.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 7.0 to 7.4.

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, http://www.cco.caltech.edu/~dadgrp/Unnatstruct.gif, which displays structures of non-natural amino acids that have been successfully incorporated into functional ion channels) and/or amino acid analogs as are known in the art may alternatively be employed). In some embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g, modified sugars such as 2'-fluororibose, 2'-deoxyribose, and hexose).

"Substantially": As used herein, the term "substantially", and grammatic equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Subject": As used herein, the term "subject" includes humans and mammals (e.g., mice, rats, pigs, cats, dogs, and horses). In many embodiments, subjects are be mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Drawings are presented herein for illustration purposes only, not for limitation.

BRIEF DESCRIPTION OF THE DRAWINGS

The foregoing and other objects, aspects, features, and advantages of the present disclosure will become more apparent and better understood by referring to the following description taken in conjunction with the accompanying drawings, in which:

FIG. 12A illustrates human tissue microarrays (TMA) stained with P-selectin antibody (Lymphoma normal tissue is from the spleen; Lymphoma 1: non-Hodgkin B cell lymphoma (Lymph node); 2: peripheral T cell lymphoma (Lymph node); 3: brain metastases of non-Hodgkin B cell lymphoma; Lung cancer 1: lung squamous cell carcinoma; 2: small cell undifferentiated carcinoma; 3: metastatic lung adenocarcinoma; Breast cancer 1: Infiltrating ductal carcinoma; 2: advanced infiltrating ductal carcinoma; 3: lymph node metastases of infiltrating ductal carcinoma.)

FIG. 12B illustrates a percentage of positively stained samples from the TMAs calculated with imaging software.

FIG. 12C illustrates data from The Cancer Genome Atlas showing P-selectin gene alterations in various cancers.

FIG. 12D illustrates preparation schemes for fucoidan-encapsulated paclitaxel nanoparticles (FiPAX) via nanoprecipitation (top) and doxorubicin-encapsulated fucoidan nanoparticles (FiDOX) (bottom) via layer-by-layer assembly, and SEM images of FiPAX and FiDOX nanoparticles (right).

FIG. 12E illustrates binding of IR783 dye loaded FiPAX to immobilized human recombinant P-selectin after 15 min of incubation. Fluorescence was measured with a fluorescent plate reader.

FIG. 14A illustrates assay to test penetration of nanoparticles into an activated endothelial monlayer barrier and infiltration into spheroids composed of tumor cells from a small cell lung cancer patient upon activation with TNF-α.

FIG. 14B illustrates fluorescence of FiPAX or DexPAX nanoparticles in the upper and lower chambers was measured with a fluorescence plate reader at 780 nm (excitation) and 815 nm (emission) after 1 h of incubation.

FIG. 14C illustrates the endothelial monolayer component of the chamber was visualized to estimate nanoparticle internalization using a fluorescent microscope equipped with a NIR sensitive XM10 Olympus CCD camera, binding/internalization of FiPAX or control DexPAX nanoparticles to a bEnd.3 endothelial cell monolayer (CellMask Green membrane stain) upon activation with TNF-α.

FIG. 14D illustrates fluorescence images of nanoparticle penetration into tumor spheres upon endothelial activation.

FIG. 14E illustrates quantification of tumor sphere uptake from 6 images per condition using ImageJ.

FIG. 15A illustrates high expression of P-selectin in a PDX model of small cell lung cancer (top), and fluorescence efficiency from IR783 loaded FiPAX and DexPAX injected to tumor bearing mice and imaged with IVIS 24 h and 72 h after injection, n=4 (bottom).

FIG. 15B illustrates tumor growth inhibition of a P-selectin expressing small cell lung cancer PDX after a single treatment on day 12, n=10.

FIG. 15C illustrates radiation induced expression of P-selectin in mice with bilateral 3LL tumors treated with 6 Gy gamma radiation on the right flank tumor only.

FIG. 15D illustrates a percentage of P-selectin positive blood vessels from entire CD31 stained blood vessels. Data is presented as the mean of 4 images per timepoint at 10×.

FIG. 15E illustrates fluorescence efficiency from IR783 loaded FiPAX and DexPAX injected to 3LL tumor bearing mice with or without treatment of 6 Gy gamma radiation on the right flank tumor only.

FIG. 15F illustrates tumor growth inhibition via single administration of nanoparticles after radiation treatment. The data is presented as mean±standard error.

FIG. 17A illustrates representative images of P-selectin and vasculature (CD31) staining in a B16F10 melanoma experimental lung metastasis model 14 days after inoculation.

FIG. 17B illustrates survival data from two experiments using the B16F10 metastasis model treated with a single injection on day 7 after inoculation.

FIG. 17C illustrates survival data from two experiments using the B16F10 metastasis model treated with a single injection on day 7 after inoculation.

FIG. 17D illustrates bioluminescence images acquired 7 days after a single administration of treatment with FiDOX, free doxorubicin (DOX), fucoidan vehicle (Fi), or PBS control.

FIG. 17E illustrates median photon count of the 6 treatment groups measured by IVIS and quantified by LivingImage software.

FIG. 19A illustrates proliferation of and A549 cell lines measured after 4 days of treatment with MEK162 or FI-MEK as indicated (top), and biochemical analysis of A375 and A549 cell lines treated for 4 hours with MEK163 or FI-MEK (bottom).

FIG. 19B illustrates tumor growth of xenograft derived from A375 and SW620 treated once with vehicle, MEK162, FI-MEK or a daily dose of MEK162 (n=6).

FIG. 19C illustrates biochemical (western blot) quantification of pERK and Cleavage PARP on xenografts A375 tumors treated for 2 and 16 hours with MEK163 or FI-MEK.

FIG. 19D illustrates immunohistochemistry of Cleavage PARP on xenogfrat HCT116 tumors treated with MEK162 or MEK-IR.

DETAILED DESCRIPTION

It is contemplated that methods of the claimed invention encompass variations and adaptations developed using information from the embodiments described herein.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Fucoidan is a sulfated polysaccharide that is found in various species of brown algae and brown seaweed. It can be obtained and purified from natural sources, or it may be synthesized. In general, fucoidan has an average molecular weight of from about 10,000 to about 30,000 (e.g., about 20,000), but other molecular weights may be found as well. Naturally-occurring fucoidan includes F-fucoidan, which has a high content of sulfated esters of fucose (e.g., no less than 95 wt. %), and U-fucoidan, which contains sulfates esters of fucose but is about 20% glucuronic acid. The fucoidan used in various embodiments described herein contains no less than 50 wt. %, no less than 60 wt. %, no less than 70 wt. %, no less than 80 wt. %, no less than 90 wt. %, or no less than 95 wt. % sulfate esters of fucose.

Figure 1:
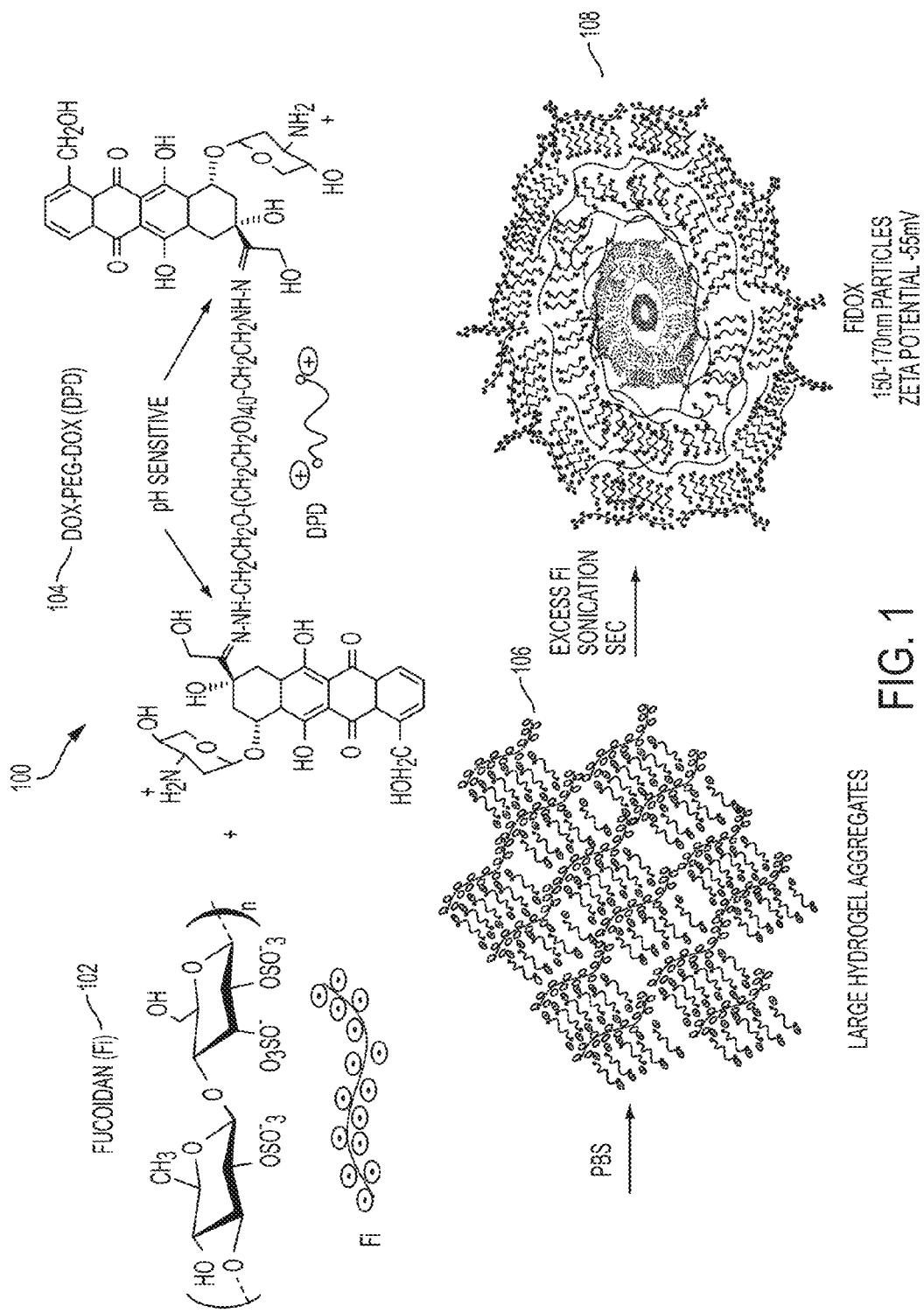
FIG. 1 is a schematic diagram illustrating the preparation of pH-sensitive fucoidan nanogels for the delivery of doxorubicin (FiDOX), according to an illustrative embodiment of the invention.

FIG. 1 is a schematic diagram 100 illustrating the preparation of pH-sensitive fucoidan nanogels for the delivery of doxorubicin (FiDOX). The pH sensitivity is conferred by hydrozone linkages between doxorubicin and polyethylene glycol (PEG). The fucoidan and DOX-PEG-DOX constructs are assembled via a layer-by-layer approach. Fucoidan (Fi) at 102 is contacted with the DOX-PEG-DOX construct (DPD) at 104 in the presence of a phosphonobile salt (PBS), thereby forming hydrogel aggregates at 106. The resulting aggregates are sonicated to form FiDOX nanoparticles. In one example, the particles had average diameter of from about 150 nm to about 170 nm, with a zeta potential of −55 mV.

In various embodiments, the average particle diameter of FiDOX, or other drug-containing fucoidan nanogel, is from about 20 nm to about 400 nm, or from about 100 nm to about 200 nm, or from about 150 nm to about 170 nm. The average particle diameter may be measured, for example, via dynamic light scattering (DLS) of a nanogel dispersed in a solvent, or can be measured via transmission electron micrograph (TEM). In some embodiments, the nanogel has a substantially monodisperse particle size (e.g., has polydispersity index, Mw/Mn of less than 20, more preferably less than 10, and still more preferably less than 5, less than 2, or less than 1.5, e.g., has polydispersity index in the range from 0 to 1, e.g., from 0.05 to 0.3). Nanoparticles similar to FiDOX can be synthesized to encapsulate the drug vincristine, or other cationic drugs, by replacing the DOX-PEG-DOX construct with another drug construct containing the desired drug.

Figure 2A:
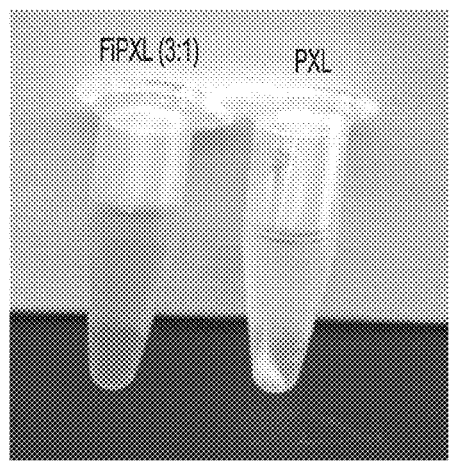
FIG. 2A shows vials containing fucoidan-paclitaxel nanoparticles (FiPXL), according to an illustrative embodiment of the invention.
Figure 2B:
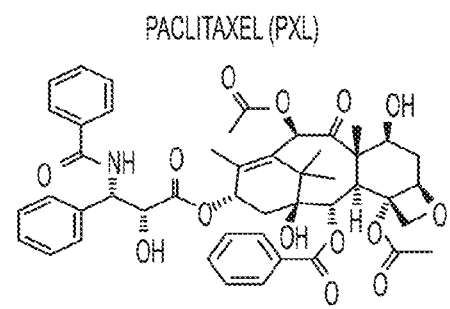
FIG. 2B shows the chemical structure of paclitaxel (PX) and fucoidan (Fi) in the fucoidan-paclitaxel nanoparticles, according to an illustrative embodiment of the invention.
Figure 2B:
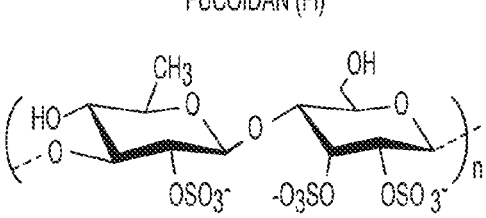

FIG. 2A shows vials containing fucoidan-paclitaxel nanoparticles (FiPXL). These were prepared using a self-assembly approach, without chemical conjugation. This can be performed to encapsulate other drugs as well, such as ispinesib, MEK162, and sorafenib, for example. FIG. 2B shows the chemical structure of paclitaxel (PX) and fucoidan (Fi) in the fucoidan-paclitaxel nanoparticles.

Figure 3A:
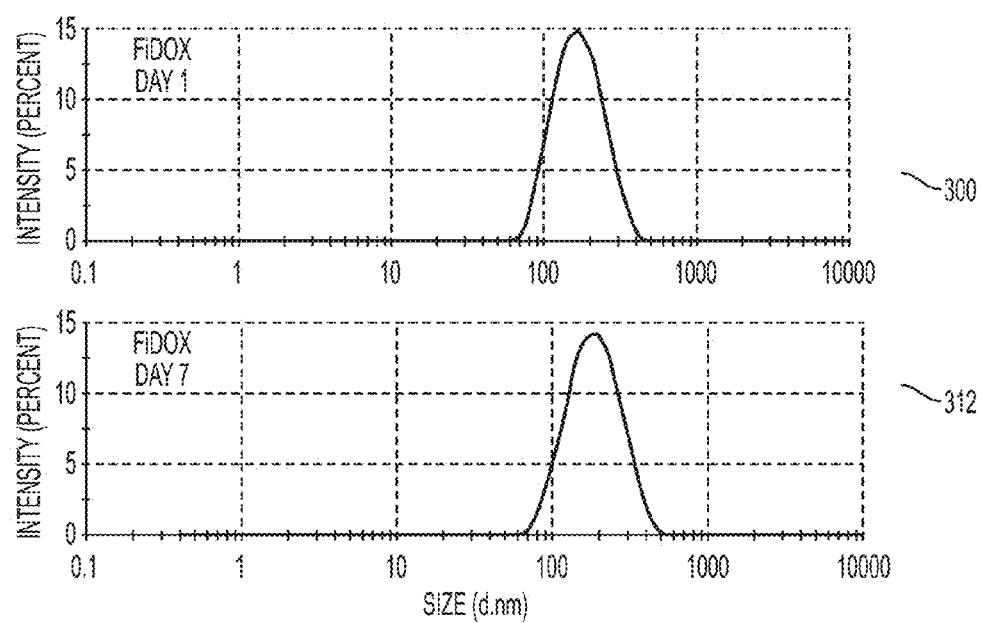
FIG. 3A are plots of dynamic light scattering measurements of FiDOX nanogels, according to an illustrative embodiment of the invention.
Figure 3B:
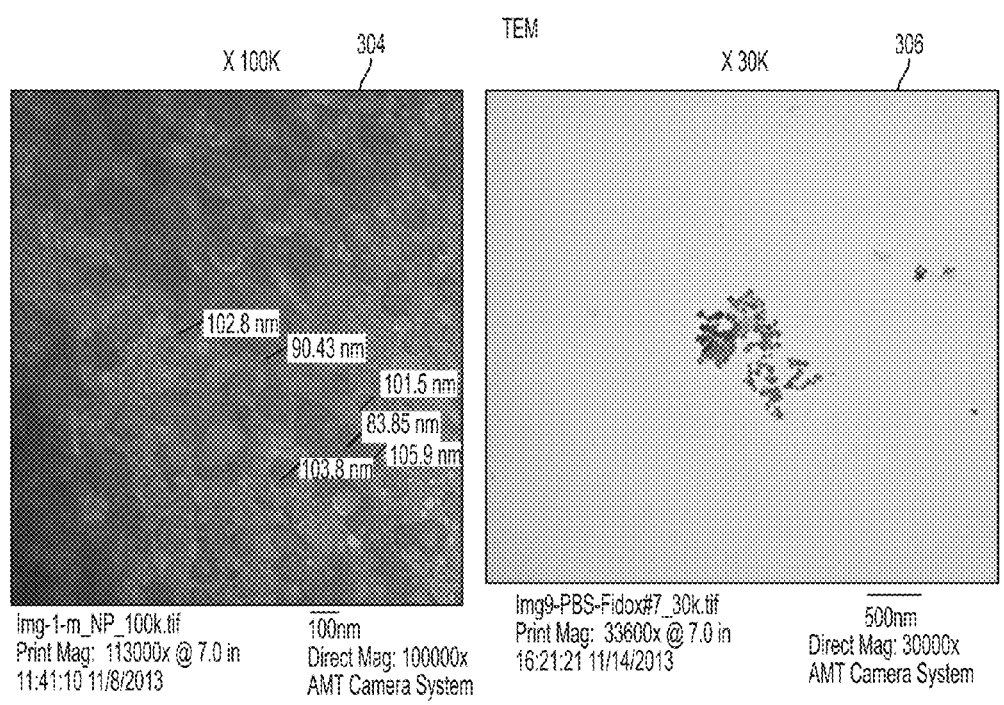
FIG. 3B are transmission electron microscope images of nanogels, according to an illustrative embodiment of the invention.

FIG. 3A shows plots of dynamic light scattering measurements of FiDOX nanogels, showing the particle diameter characterization is stable over at least seven days. FIG. 3B shows transmission electron microscope images of the FiDOX nanogels at different concentrations and magnification.

Figure 4:
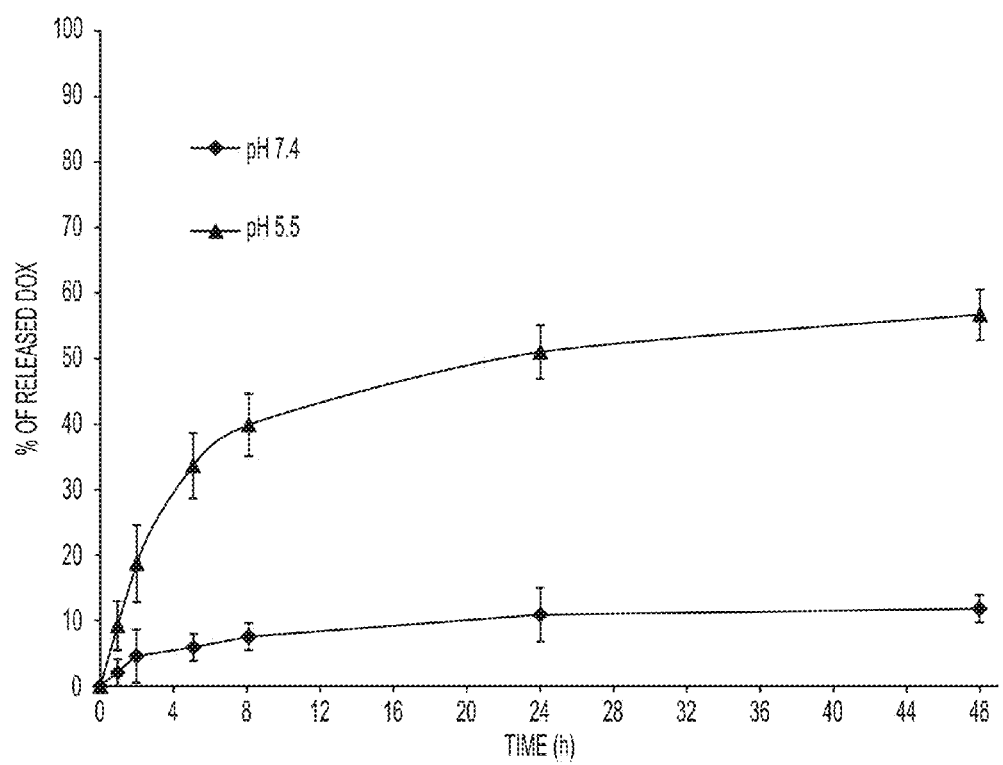
FIG. 4 is a graph showing rate of release of doxorubicin from FiDOX nanogels over time, as a function of pH, according to an illustrative embodiment of the invention.

FIG. 4 is a graph showing the percentage of released doxorubicin from FiDOX nanogels over time, as a function of pH. Low pH allows faster release due to the breakage of hydrazone bonds.

Figure 5A:
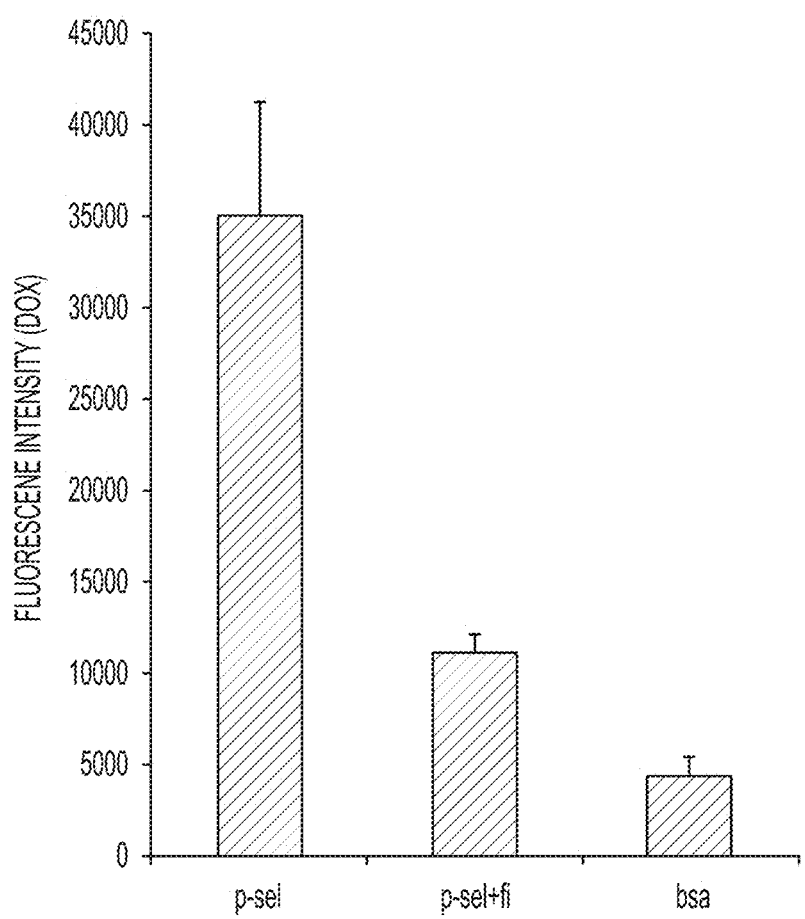
FIG. 5A shows a plot of fluorescence intensity demonstrating in vitro activity of FiDOX nanogels, according to an illustrative embodiment of the invention.

FIG. 5A shows a plot of fluorescence intensity demonstrating in vitro activity of FiDOX nanogels. The binding of FiDOX to immobilized P-selectin was estimated by measuring fluorescence intensity of bound particles. Soluble fucoidan was able to inhibit binding. A recombinant human P-selectin protein was immobilized on an ELISA plate. FiDOX particles were added to the wells for 15 min and then washed. The bound particles were detected with a fluorescence plate reader. Free fucoidan was used to inhibit the binding of the particles to the immobilized P-selectin on the surface. The particles did not bind to immobilized albumin (BSA).

Figure 5B:
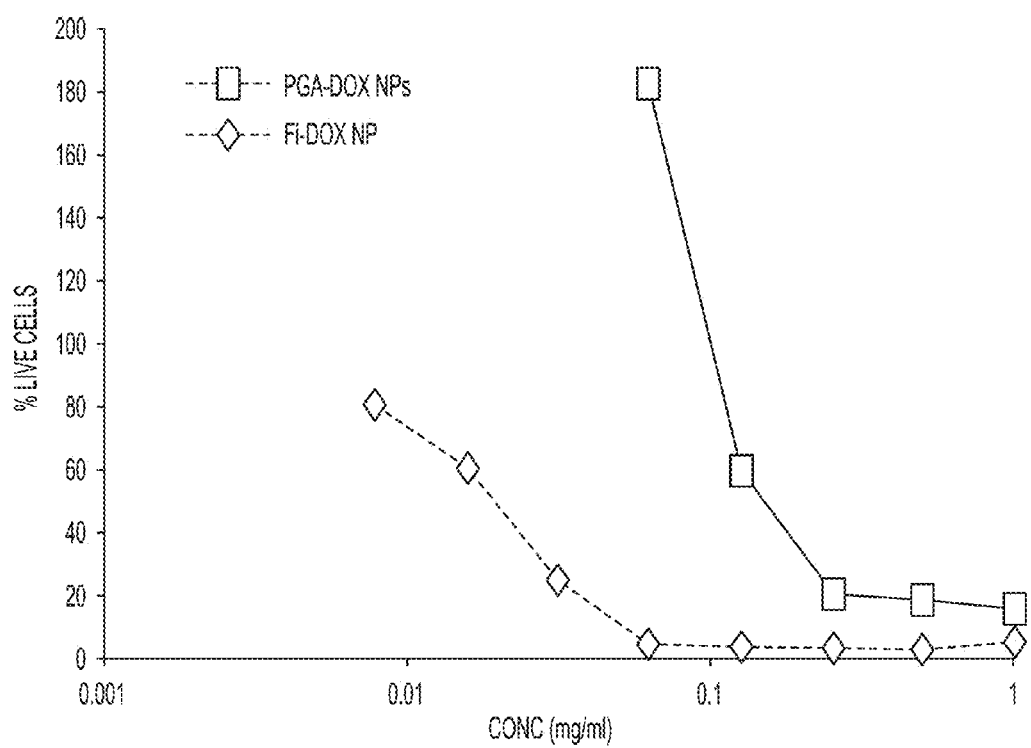
FIG. 5B shows a plot of an MTT cell viability assay, according to an illustrative embodiment of the invention.

FIG. 5B shows a plot of an MTT cell viability assay. The plot shows that FiDOX was more cytotoxic to B16F10 cells compared to polyglutamic acid-based nanogels.

Figure 6:
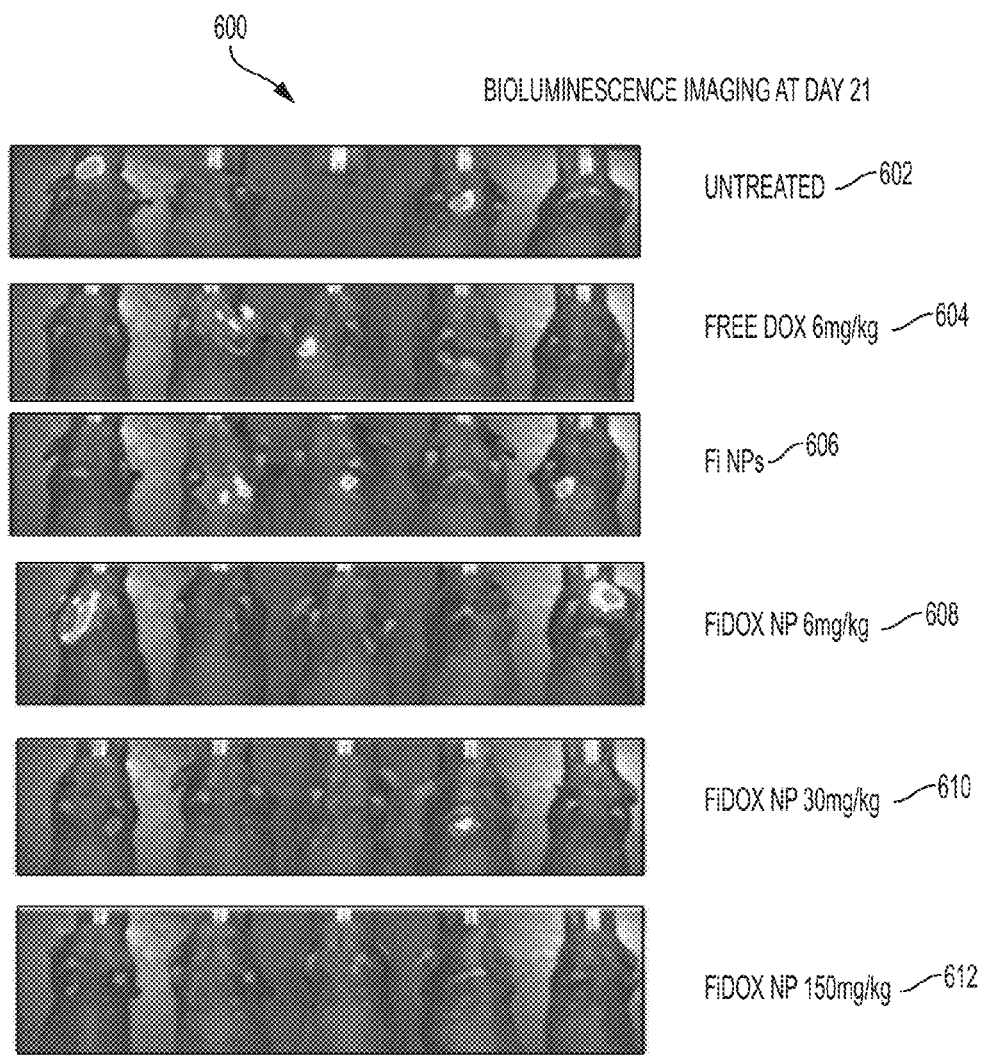
FIG. 6 shows bioluminescence images demonstrating anti-tumor efficacy of FiDOX nanogels, according to an illustrative embodiment of the invention.

FIG. 6 shows bioluminescence images at day 21 of testing, demonstrating anti-tumor efficacy of FiDOX nanogels. A luciferase-expressing B16F10 melanoma lung metastasis model was used. The cells were injected into the tail vein at day 0. The FiDOX particles and controls were injected at day 7. The progression of metastasis was monitored with bioluminescence imaging after injection of luciferin. The bioluminescence images show the luciferase-expressing B16F10 cancer cells after injection of D-luciferin, 21 days after inoculation and 14 days after a single treatment. The FiDOX nanoparticles at 30 mg/kg and above clearly show more effective treatment than the untreated specimens, as well as specimens administered free DOX drug (not in nanoparticle form), or fucoidan nanoparticles without the DOX drug (Fi NPs).

Figure 7:
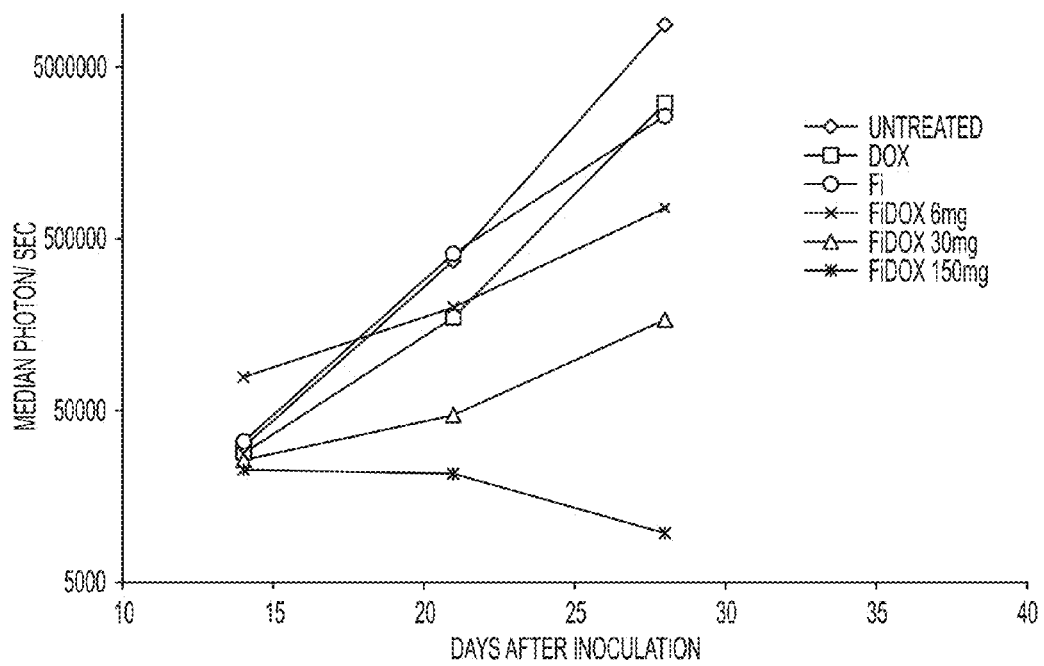
FIG. 7 is a plot of bioluminescence showing anti-tumor efficacy of FiDOX nanogels, according to an illustrative embodiment of the invention.

FIG. 7 is a plot of bioluminescence from the same test, showing anti-tumor efficacy of FiDOX nanogels. Here in FIG. 7, the median number of photons/sec/cm$^2$/steradian was measured at given time points to demonstrate decreased tumor burden in FiDOX treated mice.

Figure 8:
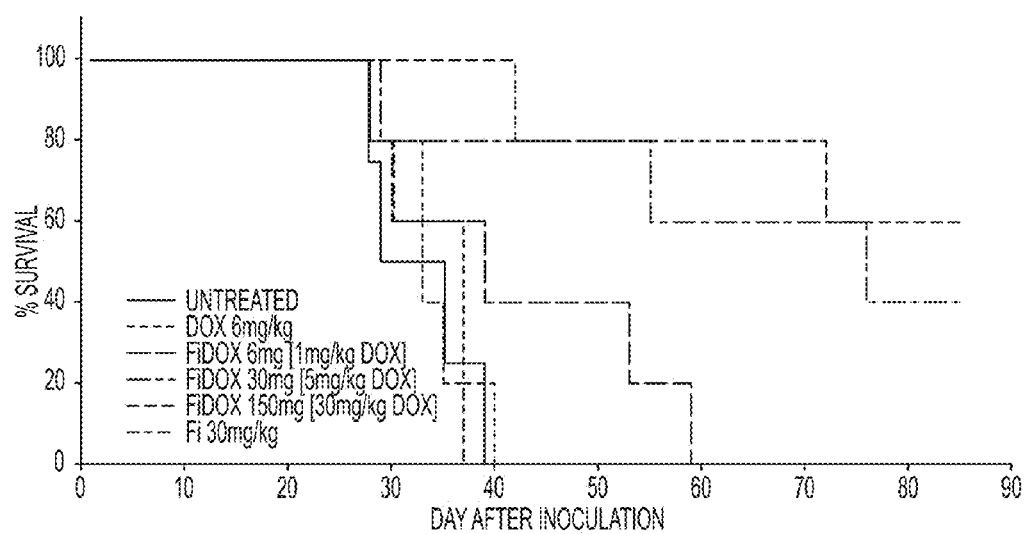
FIG. 8 is a plot showing laboratory mouse survival curve data following injection of FiDOX nanogel, according to an illustrative embodiment of the invention.

FIG. 8 is a plot showing laboratory mouse survival curve data in the B16F10 melanoma lung metastasis model treated with a single injection of FiDOX nanoparticles, injected on day 7. The results compared favorably to an injection of free doxorubicin (DOX), fucoidan alone (Fi), and the untreated control.

Figure 9:
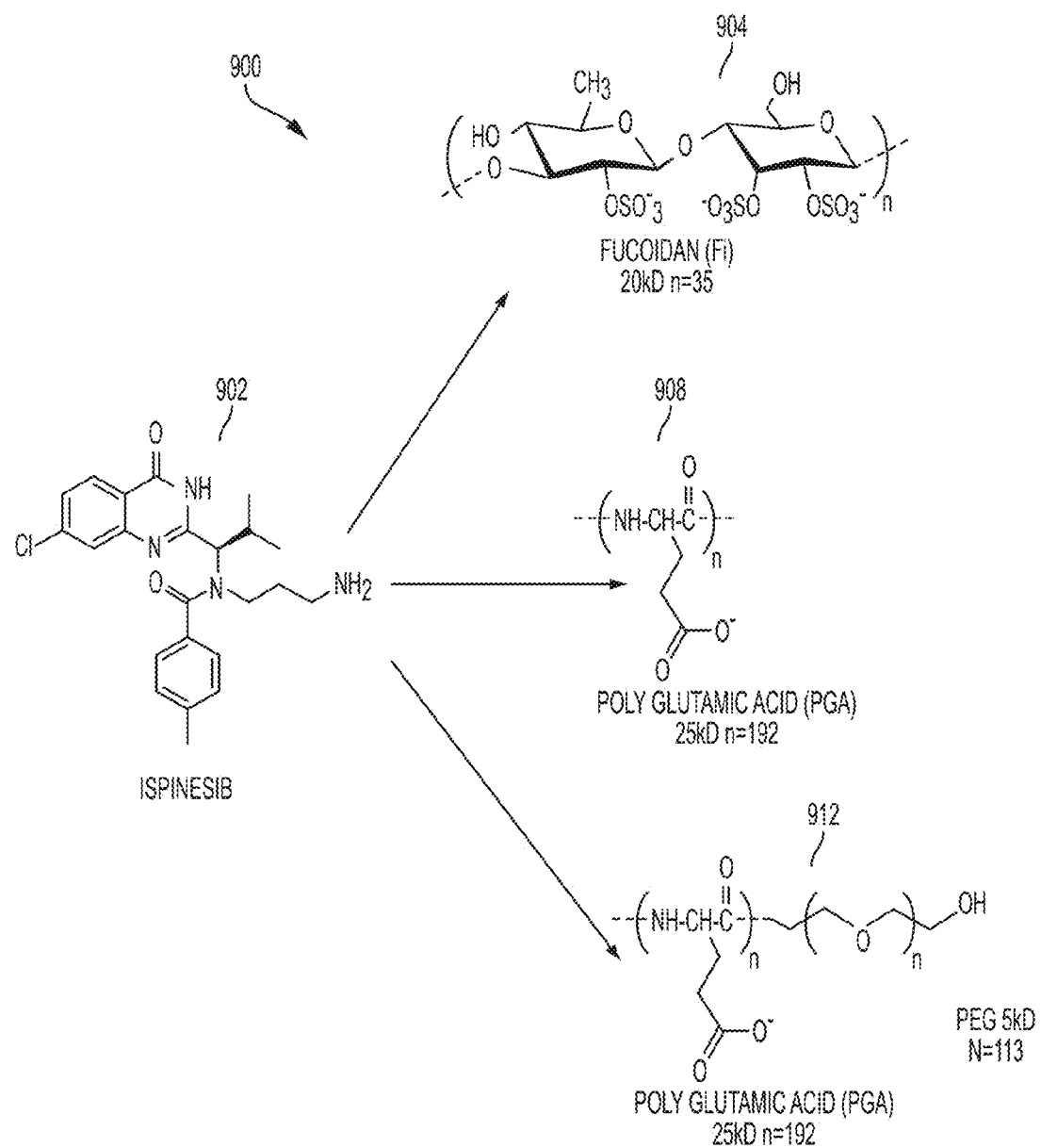
FIG. 9 is a schematic showing fucoidan-ispinesib nanogels (Fi-ISP) and analogous nanoparticles, according to an illustrative embodiment of the invention.
Figure 9:
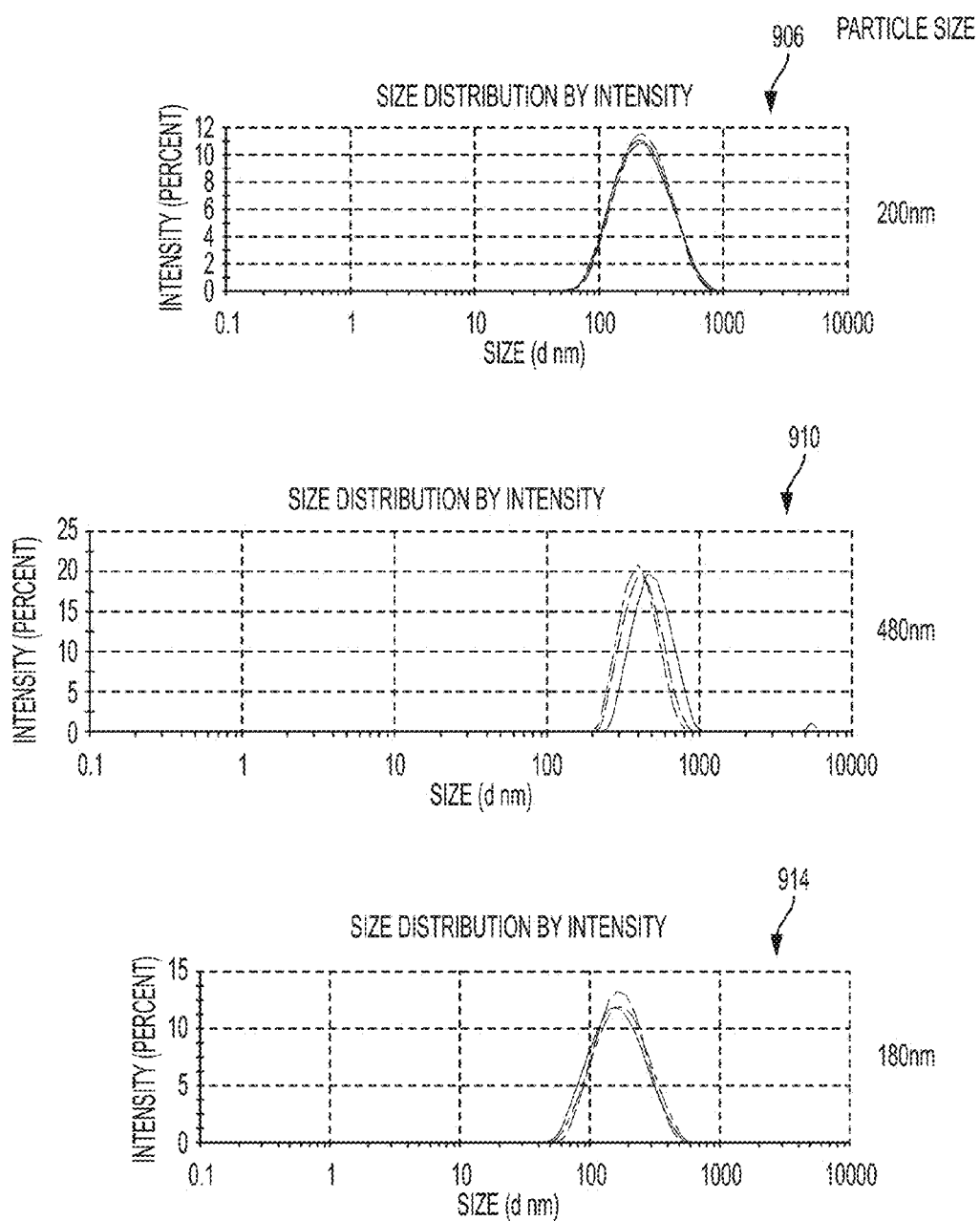
Figure 10A:
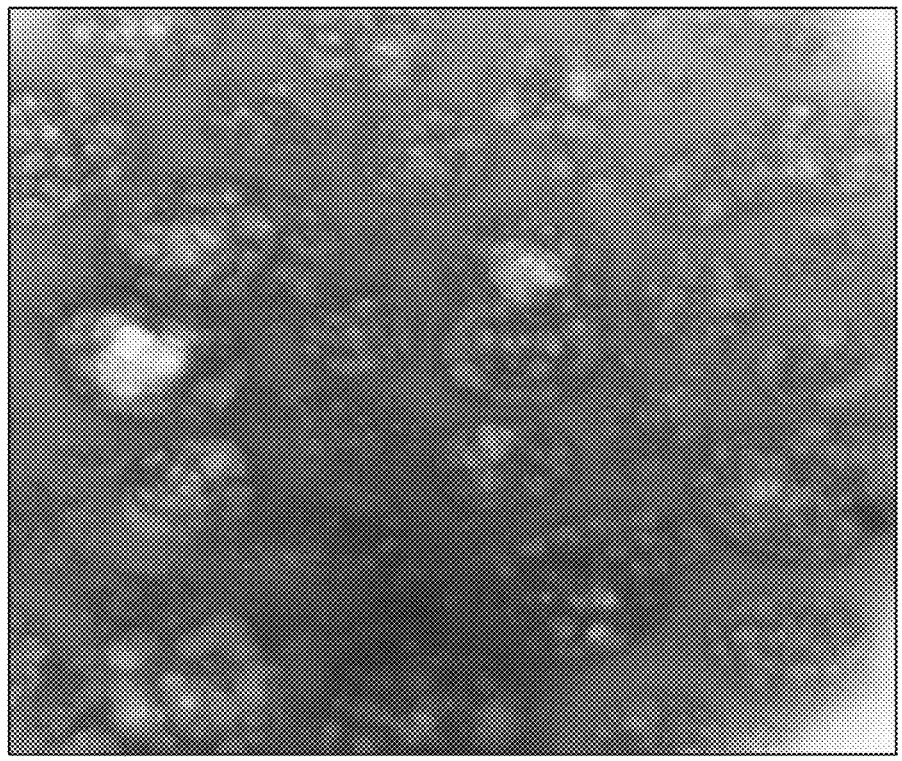
FIGS. 10A and 10B are electron micrographs of fucoidan-ispenesib nanoparticles (Fi-ISP) and PGA-ispinesib nanoparticles, according to an illustrative embodiment of the invention.
Figure 10B:
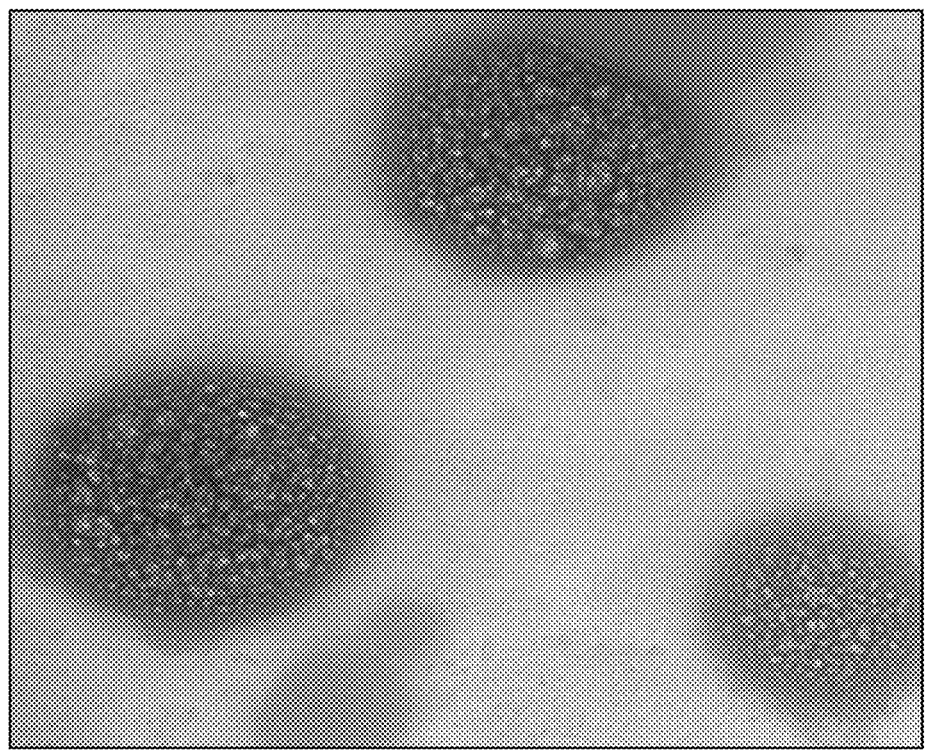
Figure 11:
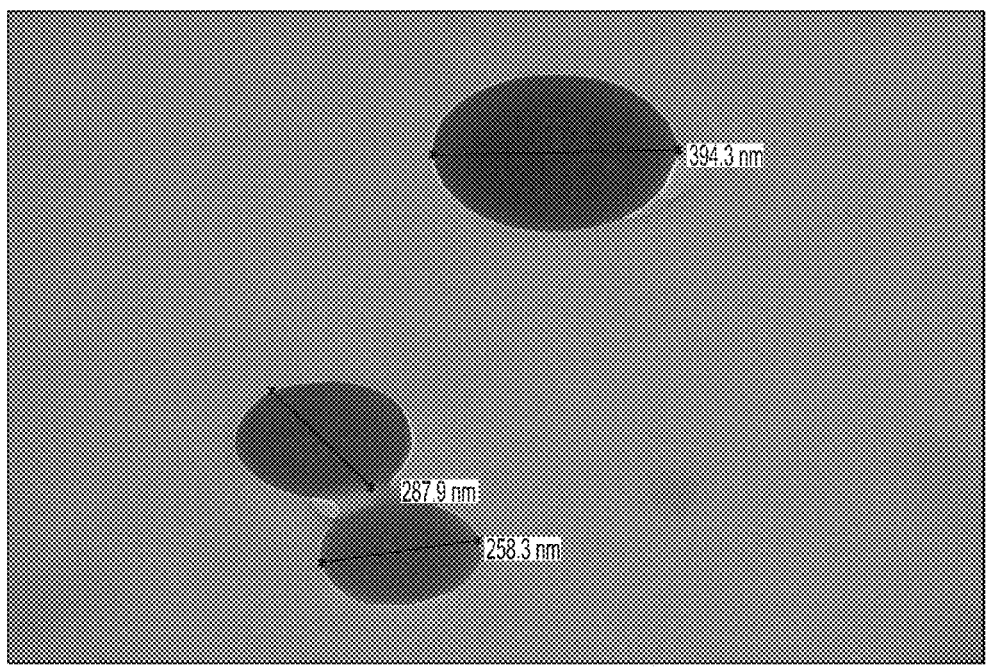
FIG. 11 is an electron micrograph of fucoidan-MEK162 nanoparticles, according to an illustrative embodiment of the invention.

FIG. 9 is a schematic showing fucoidan-ispinesib nanogels (Fi-ISP) and analogous nanoparticles made by combining ispinesib with fucoidan or Poly Glutamic Acid (PGA) or PGA-PEG. Nanoparticles were formed by non-covalent assembly. Dynamic light scattering (DLS) plots are shown at 906, 910, and 914. FIGS. 10A and 10B are electron micrographs of the fucoidan-ispenesib nanoparticles (Fi-ISP) and PGA-ispinesib nanoparticles. FIG. 11 is an electron micrograph of fucoidan-MEK162 nanoparticles.

1 mg of MEK162 in 0.1 ml of DMSO was added dropwise to 15 mg of Fucoidan in 0.5 ml of sodium bicarbonate. The mixture was immediately sonicated for 2 min with a probe sonicator (40%) under ice. The mixture was centrifuged at 20.00 g for 20 min and the pellet was re-suspended in 1 ml PBS containing 1 mg of Fucoidan and was again sonicated for 2 min under ice. The particles were characterized with DLS, TEM and zeta potential measurements. 155 nm particles were obtained with −50 mV surface zeta potential.

Experimental Examples

Preparation of DOX-PEG-DOX (DPD)

10 mg of Hydrazide-PEG-hydrazide, NH2NH-PEG-NHNH2, MW 3400 (from NANOCS) and 10 mg Doxorubicin were dissolved in 3 ml methanol containing 100 μL of glacial acetic acid. The mixture was stirred in the dark for 24 h and then slowly precipitated in cold acetone/ether (2:1), collected with centrifugation (15,000 g, 20 min) and dried with vacuum. The product, DOX-PEG-DOX (DPD) was purified with Sephadex G25 PD10 desalting column with water as eluent and then lyophilized.

Figure 20A:
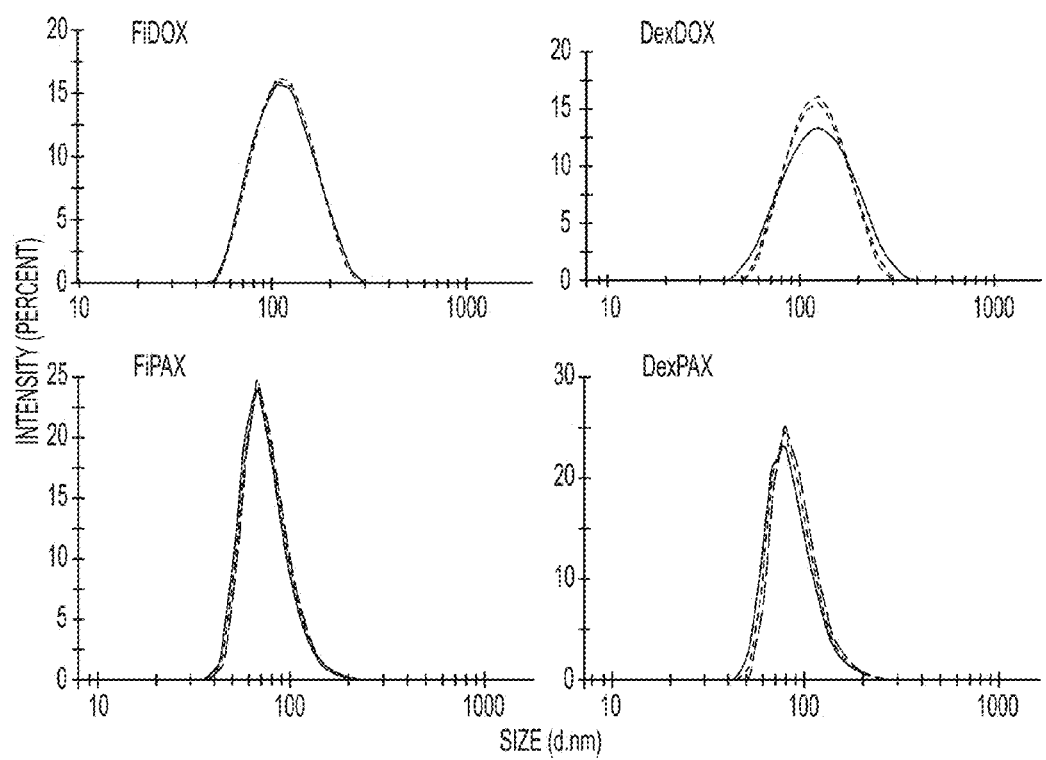
FIG. 20A shows the size distribution of FiDOX, DexDOX, FiPAX, and DexPAX nanoparticles.
Figure 20B:
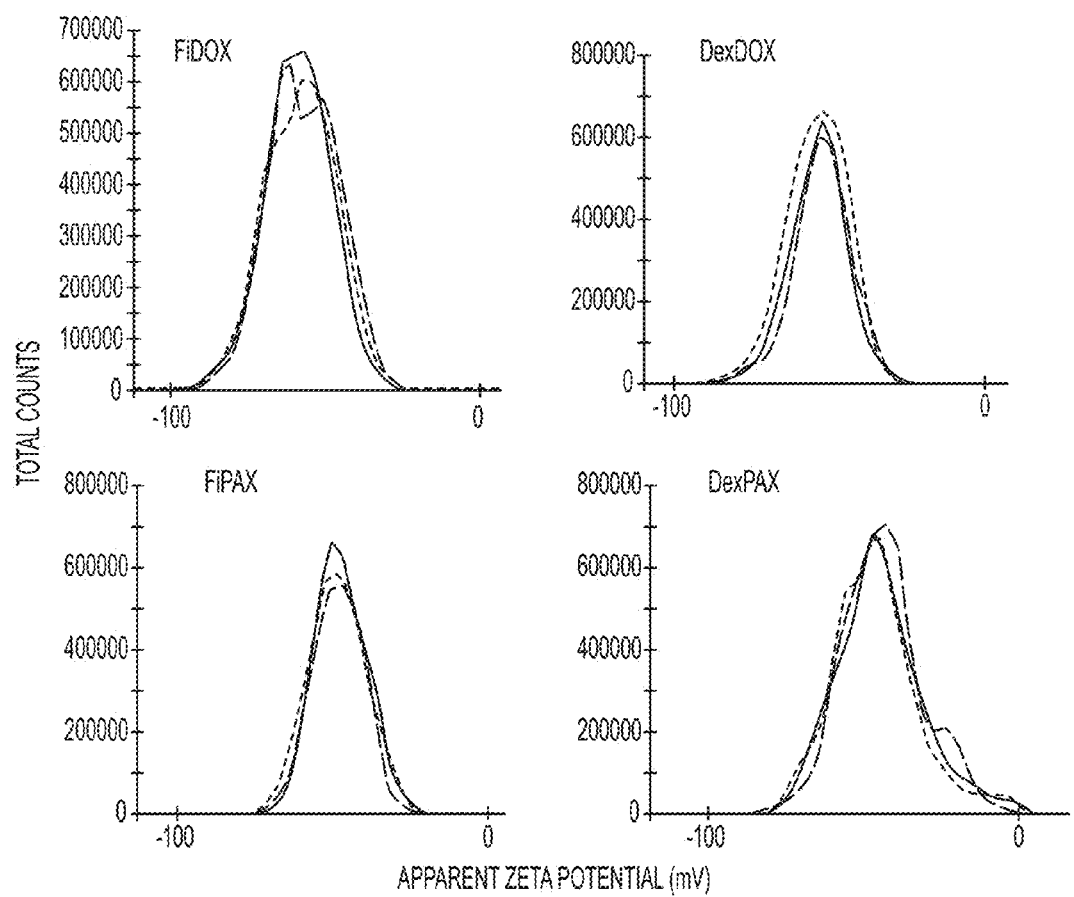
FIG. 20B shows the zeta potential of FiDOX, DexDOX, FiPAX, and DexPAX nanoparticles.
Figure 20C:
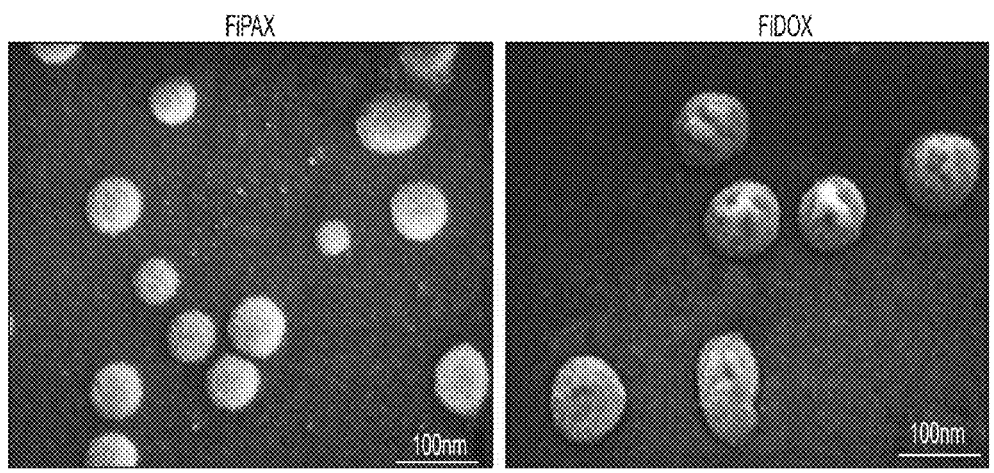
FIG. 20C shows SEM images of FiPAX and FiDOX nanoparticles. Scale bar is 100 nm.
Figure 20D:
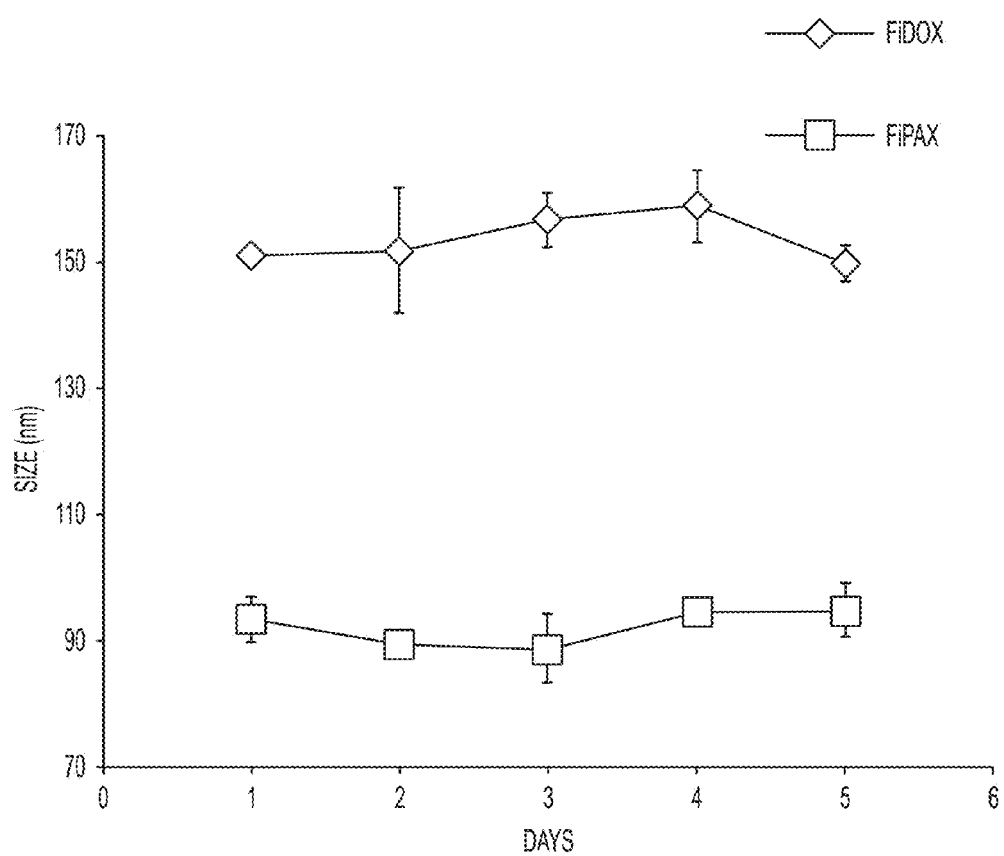
FIG. 20D shows that the sizes of FiDOX and FiPAX stays constant over a 5 day period.
Figure 20E:
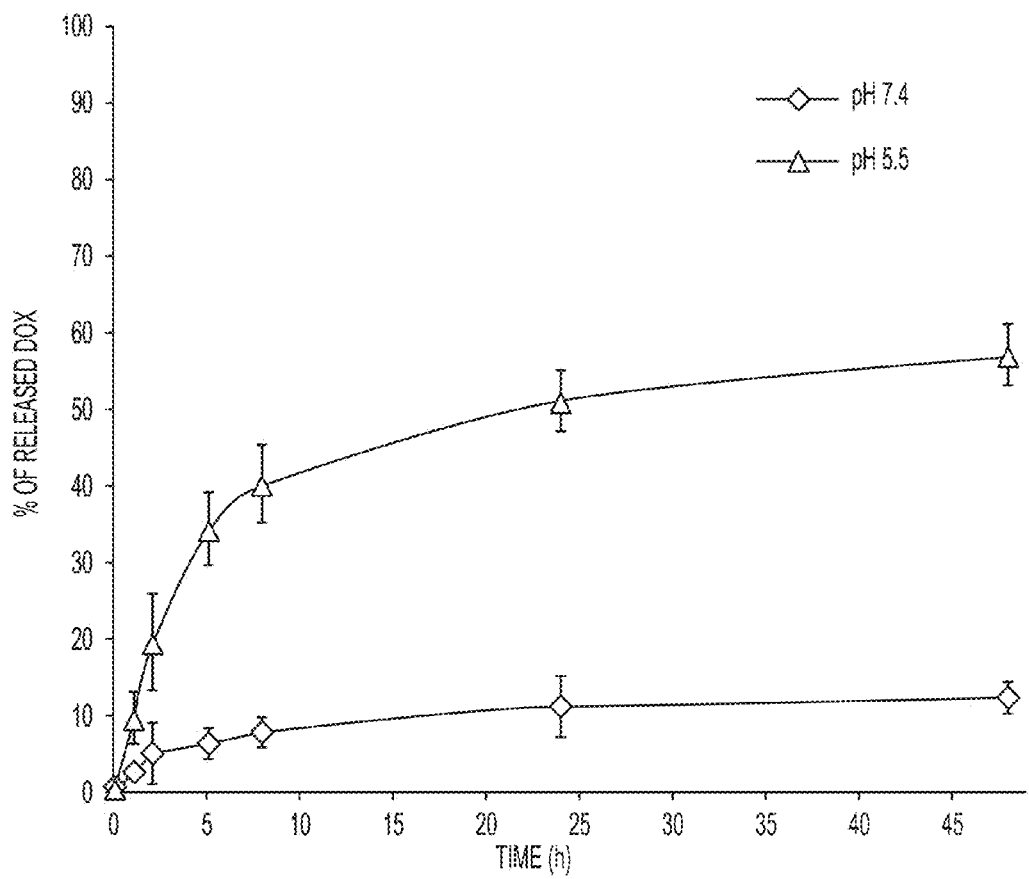
FIG. 20E shows the release of DOX over time for pH 7.4 and pH 5.5.
Figure 20F:
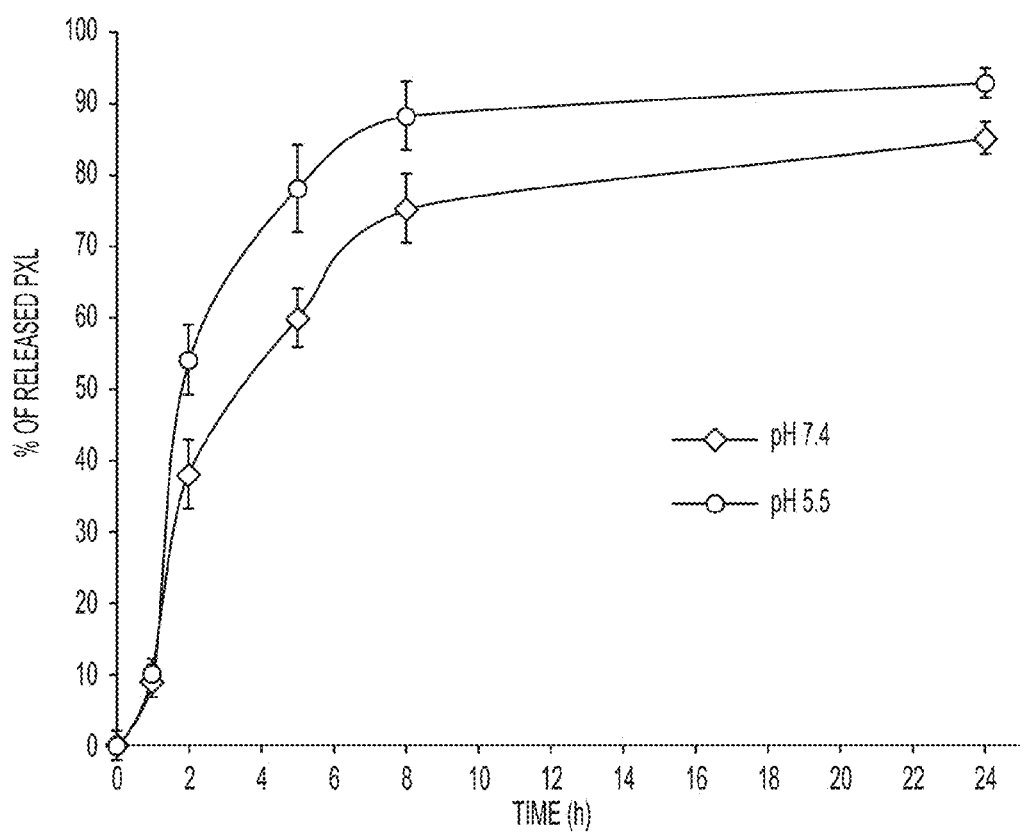
FIG. 20F shows release of PXL over time for pH 7.4 and pH 5.5.

Preparation of FiDOX and DexDOX Nanoparticles:

Fucoidan from Fucus vesiculosus (SIGMA) and DPD were both dissolved in double distilled water and were mixed together at a weight ratio of 1:1 and formed immediate gel aggregates. The aggregates were collected with centrifugation (15,000 g 10 min) and re-suspended in PBS containing excess of ×5 Fucoidan. The mixture was sonicated with a probe sonicator 40% intensity (sonics vibracell) for 10 sec until a clear dark red solution appeared containing nanoparticles. The particles were collected with centrifugation (30,000 g 30 min), re-suspended in PBS, and sonicated in a bath sonicator for 10 min. The particles were characterized with DLS, TEM, and zeta potential measurement, and 150 nm particles were obtained with −55 mV surface zeta potential measurements (FIGS. 20A-B). FIG. 20C shows SEM images of FiDOX nanoparticles. Scale bar is 100 nm. FIG. 20D shows that the sizes of FiDOX stay constant over a 5 day period. FIG. 20E shows the release of DOX over time for pH 7.4 and pH 5.5. FIG. 20E shows release of PXL over time for pH 7.4 and pH 5.5.

Preparation of FiPAX and DexPAX Nanoparticles:

Paclitaxel-encapsulated fucoidan/dextran sulfate nanoparticles (FiPAX and DexPAX) were synthesized using a nano-precipitation method. 0.1 ml of paclitaxel dissolved in DMSO (10 mg/ml), was added drop-wise (20 μL per 15 sec) to a 0.6 ml aqueous polysaccharide solution (15 mg/ml) containing IR783 (1 mg/ml) and 0.05 mM sodium bicarbonate. The solution was centrifuged twice (20,000 G 30 min) and re-suspended in 1 ml of sterile PBS. The suspension of nanoparticles was sonicated for 10 sec with a probe sonicator at 40% intensity (Sonics). The resulted nanoparticles had zeta potential of −52 mV and a size of 95 nm with a PDI of 0.12 (FIGS. 20A-B). By suspending the nanoparticles in lower volumes, it was possible to solubilize Paclitaxel (PXL) up to 16 mg/ml in saline solution, which is 2000 times better than free drug. The nanoparticles were lyophilized with a saline/sucrose 5% solution and reconstituted in water at this concentration. FIG. 20C shows SEM images of FiPAX nanoparticles. Scale bar is 100 nm. FIG. 20D shows that the sizes of FiPAX stay constant over a 5 day period. FIG. 20E shows the release of DOX over time for pH 7.4 and pH 5.5. FIG. 20E shows release of PXL over time for pH 7.4 and pH 5.5.

Preparation of Fucoidan—Albumin Nanoparticles Containing Sorafenib:

1 mg of Sorafenib (LC labs) in DMSO was added to 4 mg of Human Serum Albumin (HSA, Sigma) in 0.3 ml of PBS (pH 4 acidified with HCl) to form a milky white mixture. 3 mg of Fucoidan in 0.3 ml water was added to the mixture. The mixture was bath sonicated for 2 min and 0.3 ml of sodium bicarbonate 100 mM was added until pH 8 was reached. The mixture was sonicated with a probe sonicator for 20 sec under ice and white clear solution containing nanoparticles. The solution was centrifuged at 30.00 g for 20 min and the pellet was re-suspended in PBS followed by bath sonication. 90 nm particles were obtained with −42 mV surface zeta potential (FIGS. 20A-B).

Preparation of Fucoidan Nanoparticles Containing Paclitaxel:

1 mg of Paclitaxel in 0.1 ml of ethanol was added dropwise to 5 mg of Fucoidan in 0.5 ml of water. The mixture was immediately sonicated for 2 min with a probe sonicator (40%) under ice. The mixture was centrifuged at 20.00 g for 20 min and the pellet was re-suspended in 1 ml PBS containing 1 mg of Fucoidan and was again sonicated for 2 min under ice. The particles were characterized with DLS, TEM and zeta potential measurements (FIGS. 20A-B). 180 nm particles were obtained with −51 mV surface zeta potential.

While the invention has been particularly shown and described with reference to specific preferred embodiments, it should be understood by those skilled in the art that various changes in form and detail may be made therein without departing from the spirit and scope of the invention as defined by the appended claims.

Preparation of Fucoidan-Albumin Nanoparticles Containing Paclitaxel and Near-IR Dye:

Conjugation of Fucoidan to BSA Via Maillard Reaction:

150 μl of BSA (20 mg/ml) was mixed with 150 μl of Fucoidan solution (80 mg/ml), then 150 μl of 0.1 M sodium bicarbonate buffer, pH 8.0, was added. The mixture was frozen at −80° C., freeze-dried, and heated at 60° C. for 5 hr. After heating, samples were dissolved in 1 ml of water, and purified with Sephadex G25 PD10 column to remove salts and unbound sugar, then freeze dried.

Preparation of Particles from Ficoidan Conjugated BSA:

The Fucoidan BSA conjugate (Fi-BSA, 15 mg) was dissolved in 0.5 ml of water. 0.1 mg of IR783 (Sigma) in water was added to the solution. 1 mg of Paclitaxel in 0.1 ml of ethanol was added dropwise and the mixture was sonicated with a probe sonicator for 1 min. The mixture was centrifuged at 20.00 g for 20 min and the pellet was re-suspended in 1 ml PBS. 110 nm particles were obtained with −45 mV surface zeta potential.

Binding of Nanoparticles to Immobilized P-Selectin:

Human recombinant P- and E-selectin (50 ng in 50 μl) was added to high hydrophobicity 96 well elisa plate and incubated at 4° C. overnight. The wells were washed with PBS, incubated with BSA (3% 0.2 ml), and incubated with FiPAX or DexPAX in Hank's balanced salt solution (HBSS) for 15 min. The wells were gently washed three times with HBSS and the binding of nanoparticles was evaluated using scanning fluorescence intensity performed by TECAN T2000 ('multiple reads per well' mode, ex 780 nm, em 820 nm).

Binding of Nanoparticles to P-Selectin Expressing Endothelial Cells:

To induce P-selectin expression, monolayers of bEnd3 cells in 24 well plates were pre-incubated with TNF-α (50 ng/ml) for 20 min prior to the onset of experiments. Control cells were left untreated. The cells were then incubated with 20 μg/ml of nanoparticle for 45 min and another 15 min with CellMask Green (Life Technologies) for membrane staining and HOESCHT 66XX for nuclear staining. The cells were then washed twice with PBS. Images were acquired with an inverted Olympus XX fluorescent microscope, equipped with XM10IR Olympus camera with an IR range and EXCITE Xenon lamp. Similar exposure time and excitation intensity were applied throughout all experiments. Merged images were obtained via processing with ImageJ. Green—Cell membrane (ex 488 nm, em 525 nm), Blue—Nucleus (ex 350 nm, em 460 nm), Red—IR783 dye in particles (ex 780 nm, em 820 nm).

Evaluation of Penetration Through Endothelial and Epithelial Barriers:

A modified Transwell assay was used to test penetration of particles through a monolayer of endothelial cells expressing P-selectin.

bEnd3 cells (5' $10^4$ in 0.5 ml) were grown on Transwell inserts in 24 wells plate for 7 days. The medium was replaced every other day. The confluence of the monolayer was validated with imaging of membrane cell staining to validate the lack of gaps between cell junctions. Following activation by TNF-α as described above, the cells were incubated with 20 μg/ml of nanoparticles for 1 h and then samples from the upper chamber (50 μl) and fluorescent intensity was measured with a fluorescence plate reader (TECAN T2000) at ex 780 nm, em 820 nm. To visualize the particles in the endothelial cells on the insert component of the chamber, the cells were washed twice with PBS and then incubated in HBSS. Images were acquired and processed as described above.

Cell Viability Assay:

bEnd3 cells ($5 \times 10^4$) were seeded in a 96-well plate. Nanoparticles were added to cells that were pre-activated by TNF-α for 30 min, at equivalent drug concentration, and were incubated for 1 h at 37° C. Cells not activated with TNF-α were treated similarly. The drug solution was then removed and replaced with fresh medium, followed by 72 h of incubation at 37° C. Cell survival was assayed by discarding the medium and adding 100 μl of fresh medium and 25 μl of 5 mg/ml MTT solution in PBS to each well. After 90 minutes, the solution was removed and 200 μl of DMSO were 10 added. Cell viability was evaluated by measuring the absorbance of each well at 570 nm relative to control wells.

Anti-Tumor Efficacy in Bilateral s.c Model of 3LL:

Murine Lewis lung carcinoma (LLC) were maintained in Dulbecco's Modified Eagle Medium (DMEM) cell culture medium supplemented with 10% fetal bovine serum, 1 mM Na pyruvate, and 50 ug/ml penicillin and streptomycin. Tumor cells were subcutaneously implanted ($1 \times 10^6$ cells per injection) in both hind limbs of eightweek old hairless SKH-1 mice. The tumor models were used for biodistribution and tumor growth studies when the tumor size reached 0.5 cm in diameter.

Irradiation of the tumors was conducted at 6 gy doses using X-ray irradiator.

Near Infrared Imaging In Vivo:

Four hours after irradiation, 200 μl (1 mg/ml) of the nanoparticles labeled with IR783 were injected via the tail vein. Biodistribution of the particles within the tumor-bearing mice was monitored with near infrared (NIR) imaging. NIR images were taken with an IVIS imaging system at various time points. Radiance (photons/sec/cm$^2$) was measured within the tumor region (region of interest, ROI) using the program LivingImage 4.2 provided by Xenogen.

Inhibition of Tumor Growth and Lung Metastasis of B16-F10 Melanoma:

C57BL/6 mice were inoculated intravenously (i.v.) with $1 \times 10^5$ B16-F10 cells on day 0 and the tumor was allowed to establish until day 7. In one experiment, mice were divided randomly into 5 groups and injected i.v. with FiDOX, Fi, DexDOX.

After treatment, mice were monitored up to 8 or 17 weeks, depending on the treatment received. At the end of the experiments, mice were sacrificed, their lungs were collected, and the number of surface-visible tumors was examined. The Kaplan-Meier method was used to evaluate survival.

Establishment of Tumor Xenografts and Studies in Nude Mice:

Six-week-old female athymic NU/NU nude mice were injected subcutaneously with $5 \times 10^5$ of A375, SW620, LOVO, and HCT116 in 100 ml culture media/Matrigel at a 1:5 ratio. For cell-line-derived xenografts, animals were randomized at a tumor volume of 70 to 120 mm$^3$ to four to six groups, with n=8-10 tumors per group. Animals were orally treated daily with MEK162 (10 mg/kg or 30 mg/kg in 0.5% carboxymethylcel-lulose sodium salt [CMC]; Sigma). Xenografts were measured with digital caliper, and tumor volumes were determined with the formula: (length× width$^2$)×($\pi$/6). Animals were euthanized using $CO_2$ inhalation. Tumor volumes are plotted as means±SEM. Mice were housed in air-filtered laminar flow cabinets with a 12-hr light/dark cycle and food and water ad libitum.

Immunohistochemistry (IHC):

For xenograft samples, dissected tissues were fixed after (e.g, immediately after) removal in a 10% buffered formalin solution for a maximum of 24 h at room temperature before being dehydrated and paraffin embedded under vacuum. The tissue sections were deparaffinized with EZPrep buffer, antigen retrieval was performed with CC1 buffer, and sections were blocked for 30 minutes with Background Buster solution (Innovex). Human P-Selectin/CD62P Monoclonal Antibody (Catalog #BBA30) at 5-15 µg/mL overnight at 4° C. Other antibodies (CD31, P-selectin IFC, Tunel and Cle-PARP) were applied and sections were incubated for 5 hr, followed by a 60 minute incubation with biotinylated goat anti-rabbit IgG (Vector labs, cat#PK6101) at a 1:200 dilution.

As described herein, it has been identified that human tumors (e.g., lymphomas) express P-selectin primarily on cancer cells and to a lesser extent in the vasculature. Because of the augmented expression on certain tumor cells and vasculature, P-selectin was tested on targeted nanoparticles in a murine model that express P-selectin in both cancer and endothelial cells, models that only express endothelial P-selectin, and models that do not express P-selectin but it can be induced by radiation. For each of the models, appropriate drugs were chosen to achieve high response to a single injection, which demonstrated the platform capabilities of Fi-based nanoparticles.

There was a significant increase in fucodian particle accumulation in P-selectin expressing tumors on cancer cells and endothelial cells (PDX and irradiated 3LL) in tumor bearing mice. An active mechanism of delivery of the chemotherapeutic agents loaded fucoidan nanoparticles (Fi-DOX and FiPAX) in P-selectin positive aggressive lung metastases and PDX models was not seen in the control nanoparticles with similar charge and size (DexDOX and DexPax. To further characterize the pharmacodynamics of fucoidan based particles, the activities of a reversible kinase inhibitor were investigated. The use of a reversible MEK inhibitor encapsulated in fucoidan nanoparticles allowed evaluation of kinase inhibition in cancer cells and correlation with drug delivery to cancer cells. Comparison of a clinically relevant regimen of daily administration of MEK162 to a single or weekly dose of the nanoparticle formulation was performed. A single or a weekly administration of a reversible inhibitor such as MEK162 encapsulated in a nanoparticle was similar to or more effective as a daily administration. This demonstrates the effectiveness of the delivery system to reach not just endothelial cells but also cancer cells. The reduction of a chronic and systemic inhibition of the pathway and the increase in local tumor concentrations for prolonged periods of time using Fi nanoparticles will be more efficacious and better tolerated.

Because the overexpression of P-selectin on endothelial cells and cancer cells varies substantially from patient to patient, radiation was examined as a way to induce P-selectin locally. In tumors without P-selectin expression, it was demonstrated that radiation increases endothelial P-selectin levels as well as particle accumulation and anti-tumor efficacy. The ability to 'turn on' expression of and translocation of P-selectin using radiation has a unique advantage since it could render virtually any tumor vulnerable to P-selectin targeted systems. Also, unexpectedly, non-irradiated tumors experienced a significant therapeutic benefit by a mechanism which may be akin to the abscopal effect.

P-selectin was investigated as a target for localized drug delivery to tumor sites, including metastases. It was found that many human tumors surprisingly express P-selectin spontaneously within their stroma, tumor cells, and tumor vasculature. A nanoparticle carrier was synthesized for chemotherapeutic and targeted therapies using the algae-derived polysaccharide, fucoidan, which exhibits nanomolar affinity for P-selectin. It was found that the targeting of activated endothelium improved the penetration of fucoidan-based nanoparticles through endothelial barriers, leading to a therapeutic advantage in P-selectin-expressing tumors and metastases. The encapsulation of both chemotherapeutic drugs and a reversible MEK inhibitor conferred a therapeutic benefit in P-selectin-expressing tumors, suggesting improved delivery to tumor tissue. On exposing tumors to ionizing radiation, which induced expression of P-selectin, a significant increase in nanoparticle localization and anti-tumor efficacy in tumors that do not spontaneously express the target was observed.

Figure 12A:
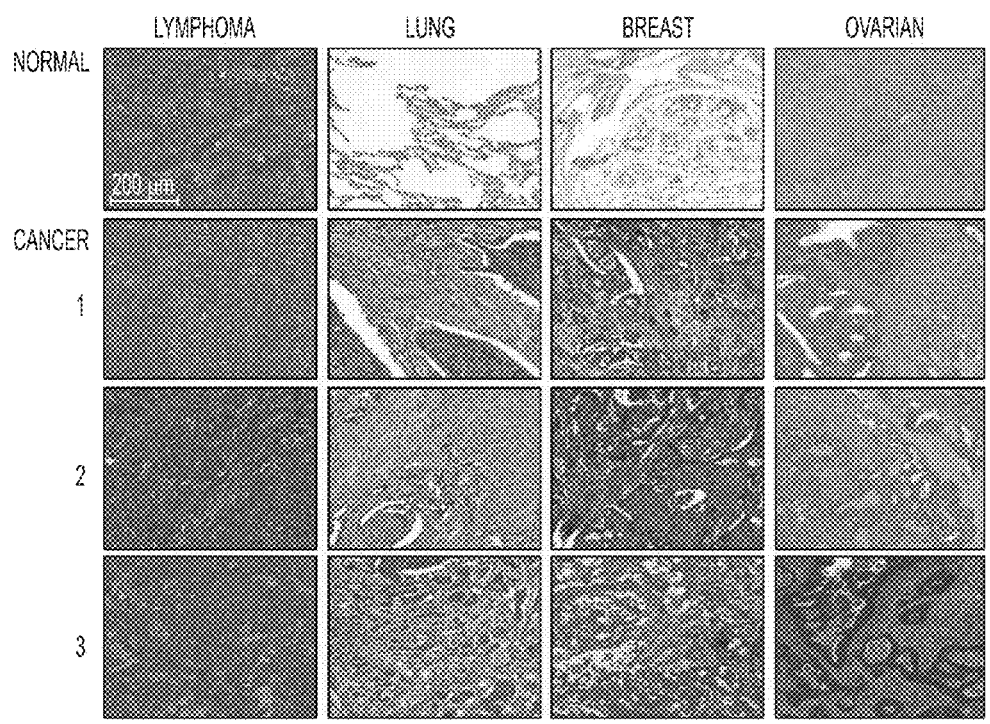
FIGS. 12A-12C illustrate P-selectin expression in human cancers.
Figure 12B:
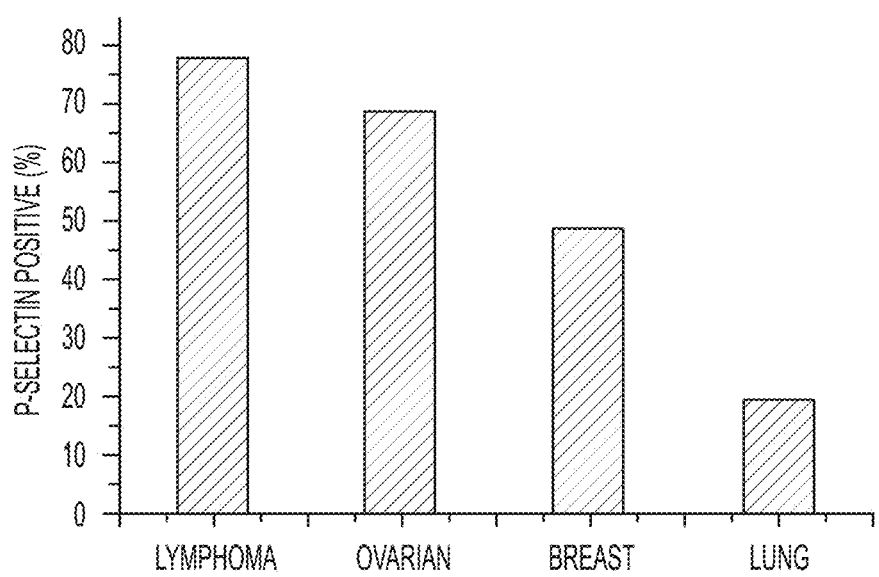
Figure 12C:
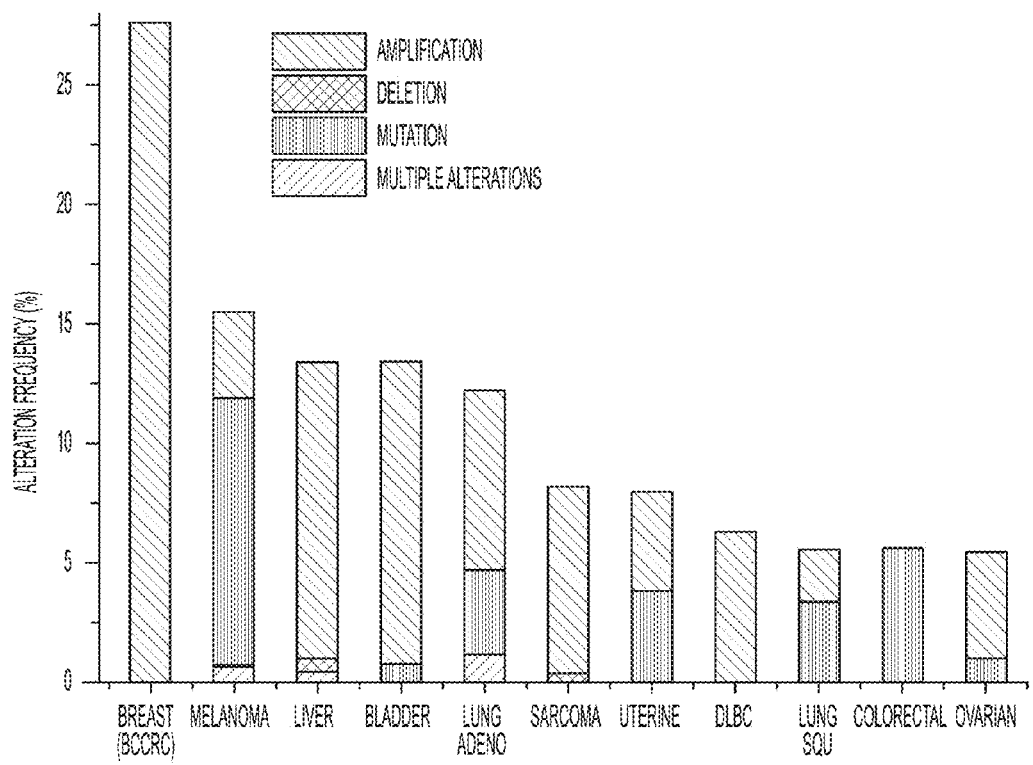

Expression of P-Selectin in Human Cancers:

In order to determine the prevalence of P-selectin expression in cancer tissues, ~400 clinical samples were assessed via immunohistochemistry. (Table S1). As shown in FIGS. 12A and 12B, it was found that P-selectin is highly expressed within multiple types of tumors and their metastases, including human lung (19%), ovarian (68%), lymphoma (78%) and breast (49%). Abundant expression of P-selectin was found in the stroma and vasculature surrounding the tumor cells. However in a subset of cancers, expression of P-selectin on tumor cells was observed. Moreover, significant genomic alterations to the P-selectin gene (SELP) were noted in The Cancer Genome Atlas (TCGA) (FIG. 12C). It was found that SELP is amplified in many cancers including breast (27.5%), liver (15%), bladder urothelial carcinoma (13.4%), and lung adenocarcinoma (12.2%). Moreover, the expression of SELP is associated with poor prognosis in squamous cell carcinoma of the lung and renal cell carcinoma. (FIG. 12C). The abundant expression of P-selectin in cancer prompted the development a P-selectin-targeted vehicle for selective drug delivery.

Figure 12D:
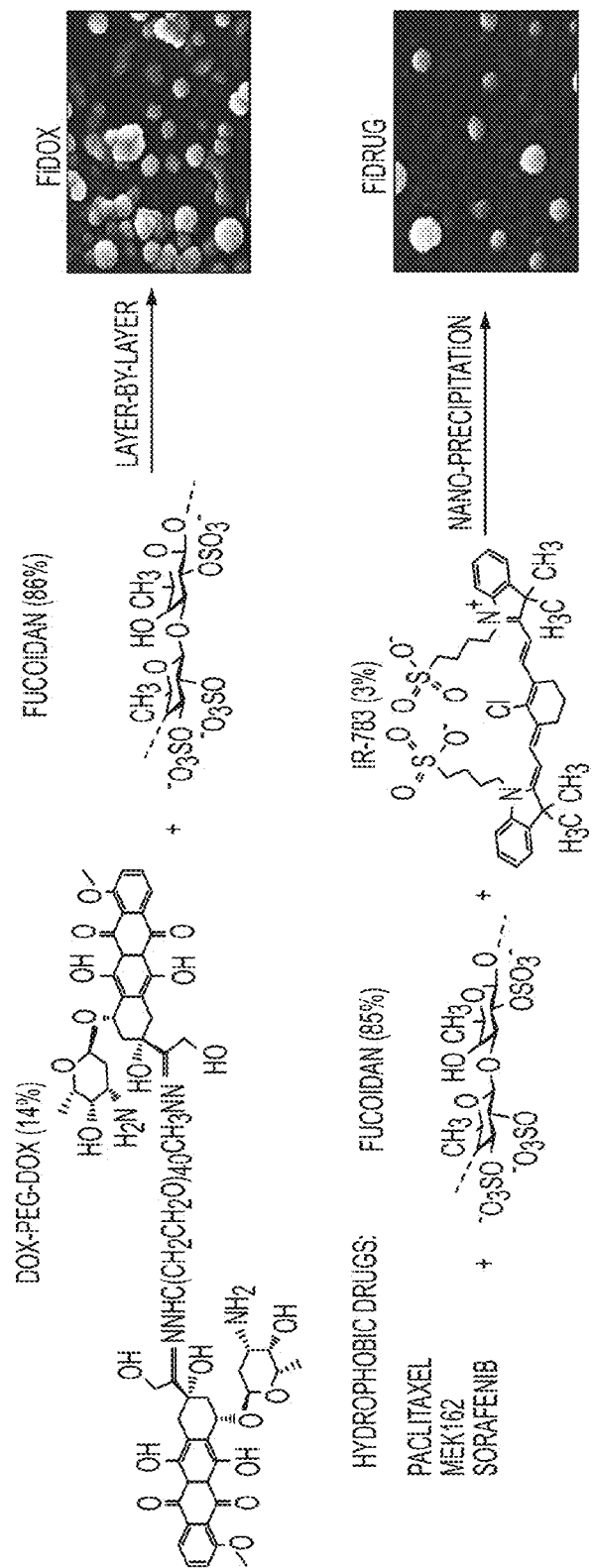
FIGS. 12D-12E illustrate a preparation scheme of P-selectin targeted nanoparticles.
Figure 12E:
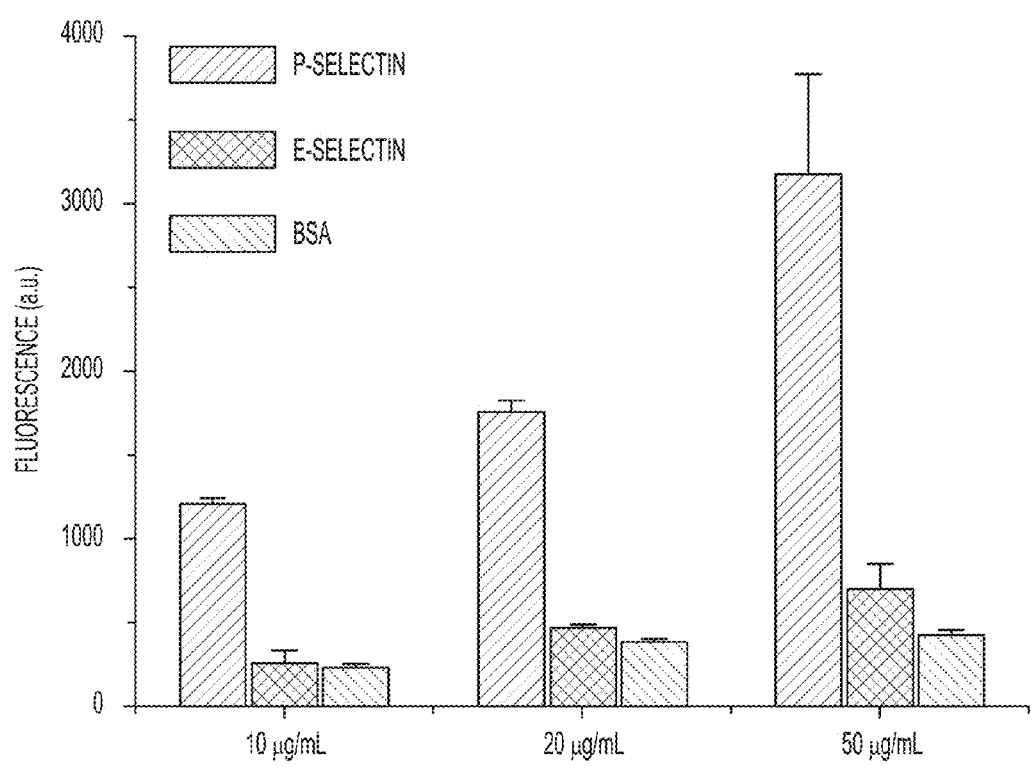
Figure 13A:
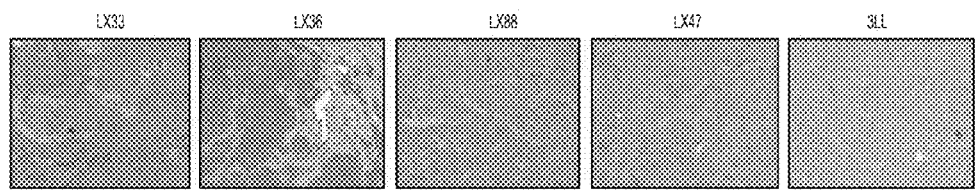
FIGS. 13A-13E illustrate anti-tumor efficacy of FiPAX vs. DexPAX with and without radiation.
Figure 13B:
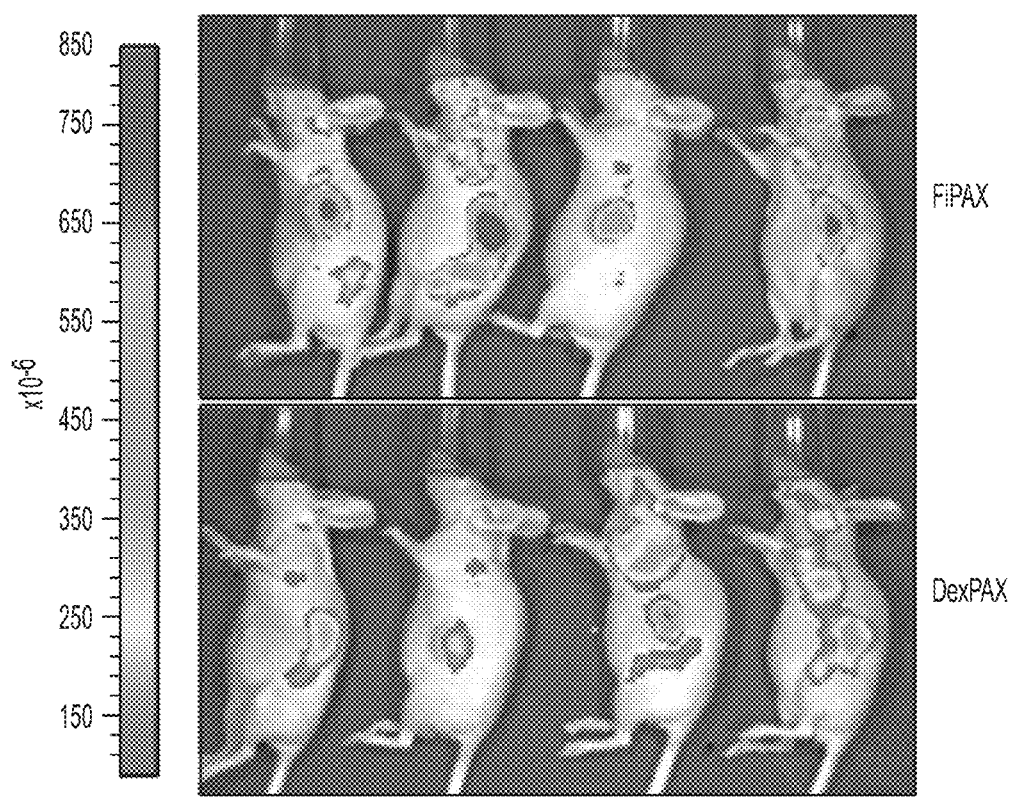
Figure 13C:
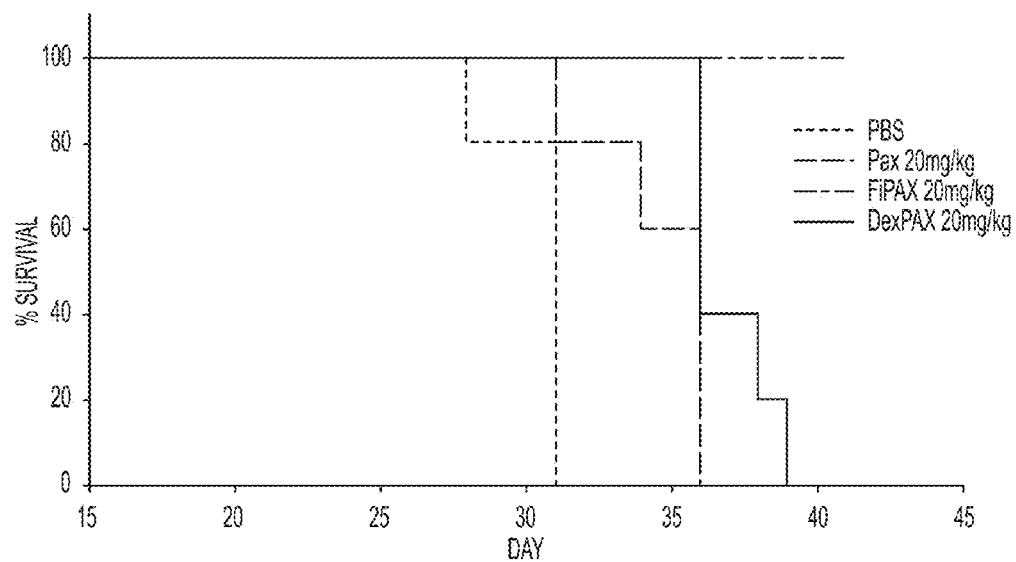
Figure 13D:
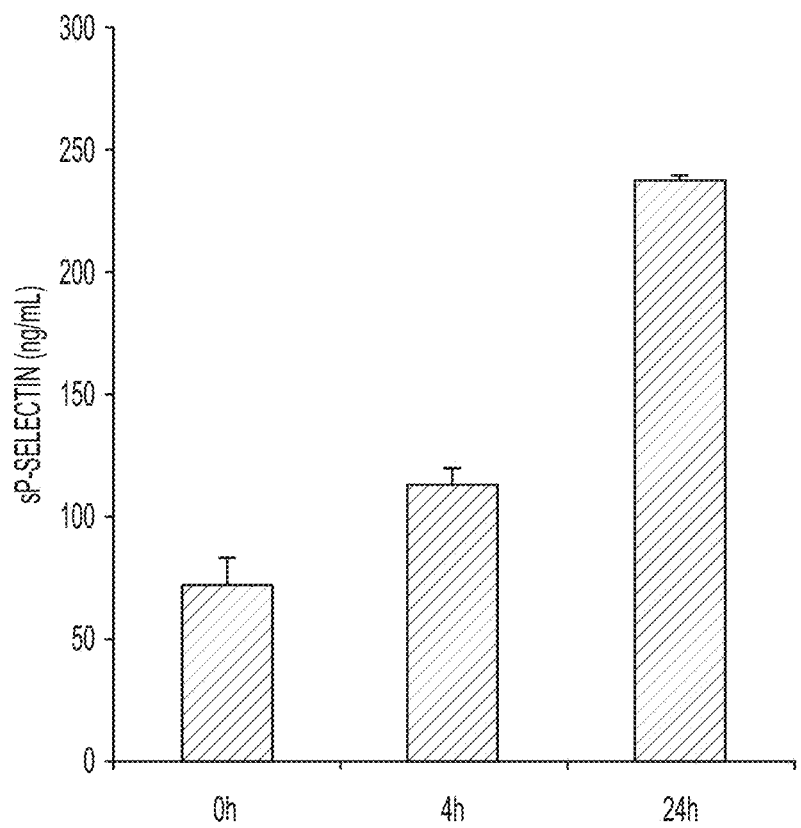
Figure 13E:
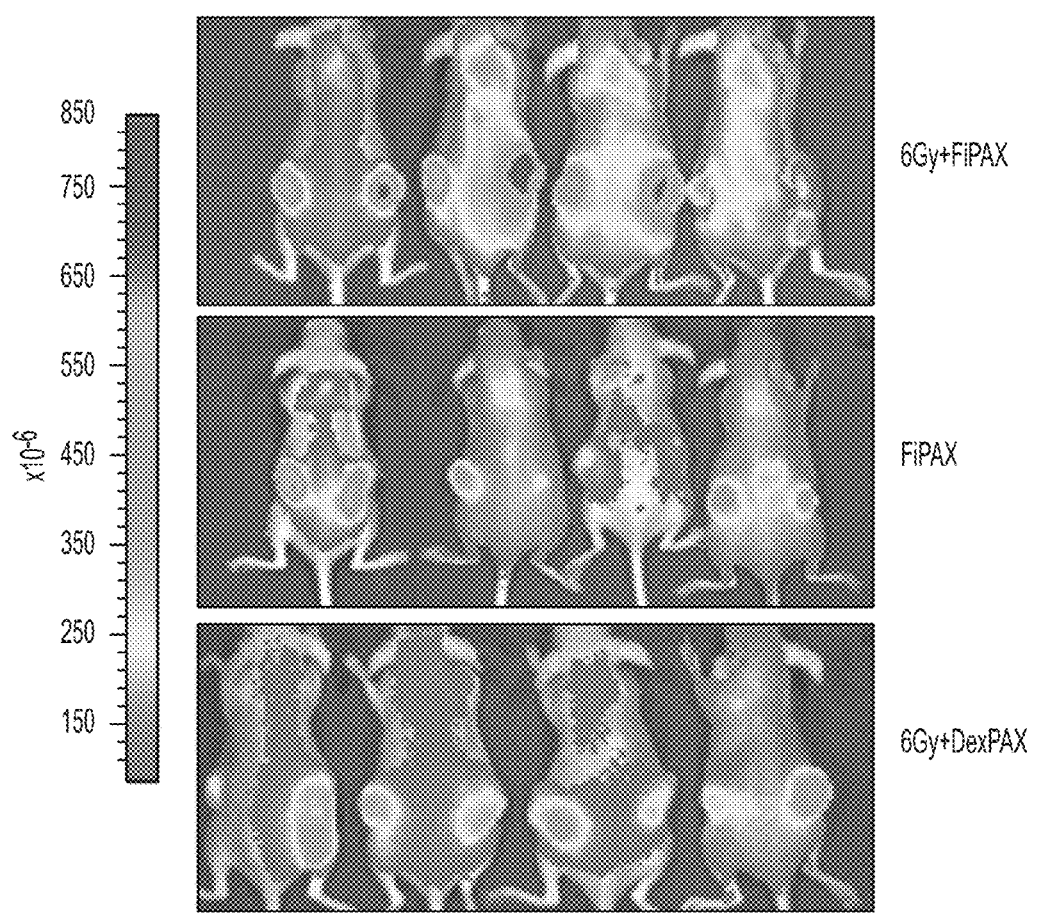

P-Selectin Mediated Transport of Nanoparticles:

To design a P-selectin targeted drug delivery system, fucoidan (Fi)-based nanoparticles were prepared to encapsulate three different drug classes with dose-limiting toxicities. Fucoidan-encapsulated paclitaxel (PAX) nanoparticles (FiPAX) were synthesized by co-encapsulating paclitaxel, and a near infra-red dye (IR783) to facilitate imaging, via nano-precipitation as described above in Preparation of FiPAX and DexPAX nanoparticles (FIG. 12D). A reversible MEK inhibitor, MEK162 was encapsulated in fucodian nanoparticles (FiMEK) in the same manner that FiPAX was prepared. Fucoidan-encapsulated doxorubicin (DOX) nanoparticles (FiDOX) were synthesized via layer-by-layer assembly of a cationic doxorubicin-polymer conjugate via pH sensitive hydrazone bond (DOX-PEG-DOX, DPD) and the anionic fucoidan (FIG. 12E). The DPD conjugate was synthesized via pH-cleavable hydrazine linkages to promote release of the drug in the acidic tumor microenvironment or lysosomes. The FiDOX, FiPAX and FiMEK nanoparticles measured 150±8.1, 105±4.2 and 85±3.6 nm in diameter respectively, and exhibited approximately −55 mV surface charge (zeta potential). Microscopy showed relatively uniform spherical morphology. As shown in Table 1 below and in FIGS. 13A-E, the particles exhibited good serum stability and reconstituted after lyphilization.

TABLE 1

| Parameters (units) | Control (NT) | FiDox (24 Hrs) | FiPax (24 Hrs) |
|---|---|---|---|
| WBCs (K/µL) | 6.90 ± 0.91 | 4.71 ± 0.28 | 5.21 ± 0.70 |
| NE (K/µL) | 3.71 ± 3.23 | 1.46 ± 0.12 | 1.61 ± 0.48 |
| LY (K/µL) | 3.03 ± 2.41 | 3.20 ± 0.29 | 3.51 ± 0.26 |
| MO (K/µL) | 0.15 ± 0.05 | 0.06 ± 0.03 | 0.07 ± 0.02 |
| EO (K/µL) | 0.03 ± 0.02 | 0.01 ± 0.01 | 0.01 ± 0.01 |
| BA (K/µL) | 0.00 ± 0.00 | 0.00 ± 0.00 | 0.00 ± 0.00 |
| RBC (M/µL) | 10.30 ± 0.69 | 10.55 ± 0.60 | 10.55 ± 0.54 |
| Hb (g/dL) | 13.30 ± 0.99 | 13.87 ± 0.50 | 13.70 ± 0.52 |
| HCT (%) | 45.05 ± 2.05 | 45.73 ± 1.96 | 45.30 ± 2.78 |
| MCV (fL) | 43.75 ± 0.92 | 43.40 ± 1.14 | 42.90 ± 0.95 |
| MCH (pg) | 12.90 ± 0.14 | 13.20 ± 0.61 | 13.00 ± 0.40 |
| MCHC (g/dL) | 29.50 ± 0.85 | 30.40 ± 0.69 | 30.30 ± 0.89 |
| PLT (K/µL) | 1082.00 ± 203.65 | 753.33 ± 50.08 | 890.33 ± 125.92 |

To assess the selectivity of nanoparticle targeting to P-selectin, an untargeted control drug-loaded nanoparticle lacking the fucoidan component was synthesized. Dextran sulfate-encapsulated paclitaxel (DexPAX) nanoparticles were assembled with the same methods as used above. The binding of FiPAX and DexPAX was compared to immobilized human recombinant P-selectin, E-selectin, and BSA, thereby confirming the selective binding to P-selectin in a dose dependent manner (FIG. 12E: P<0.05).

Figure 14A:
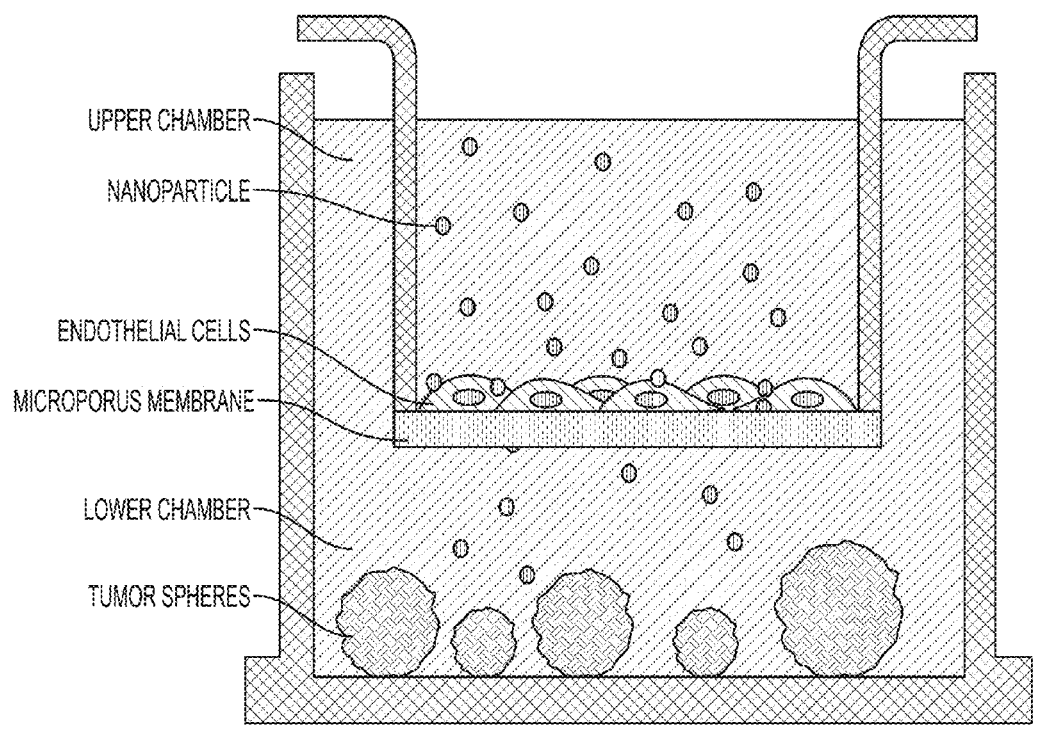
FIGS. 14A-14E illustrate selective endothelial/tumor penetration assessments in vitro.
Figure 14B:
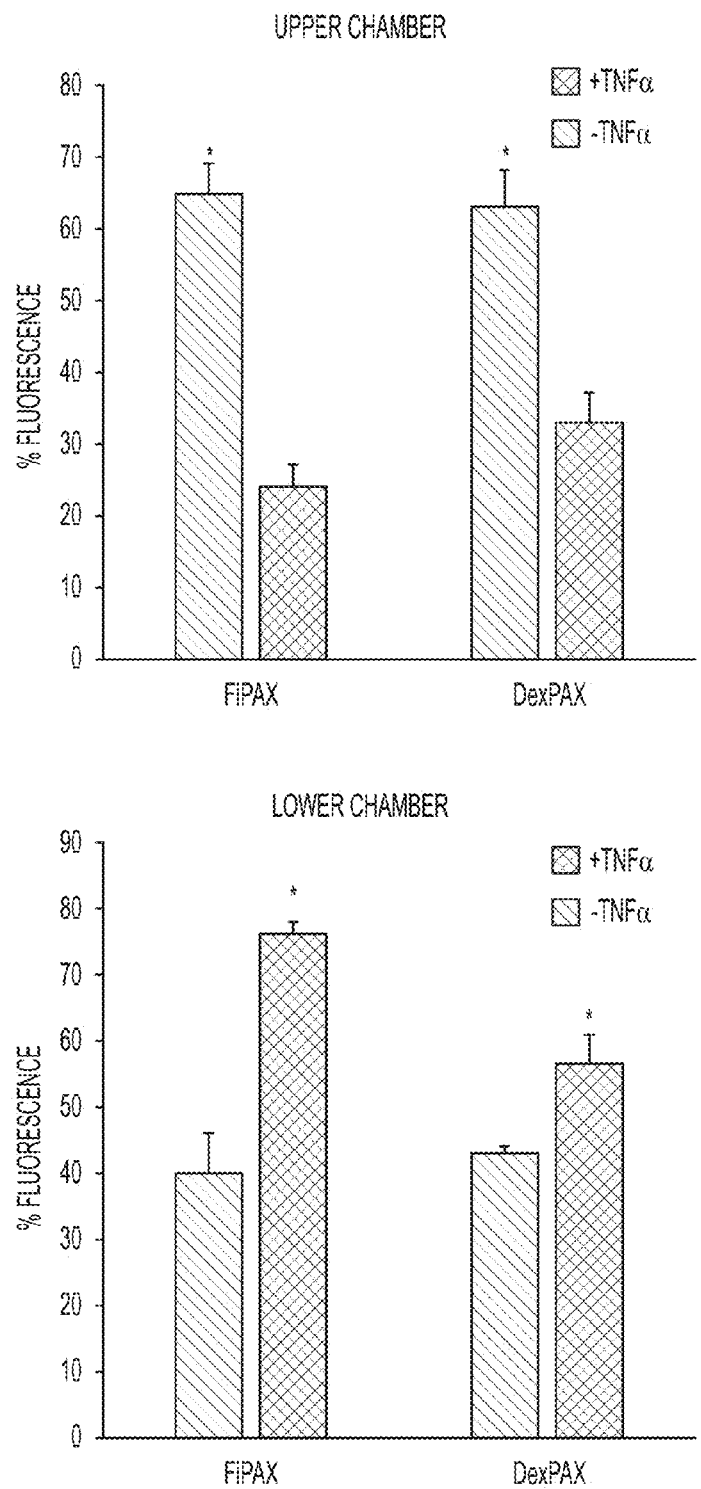
Figure 14C:
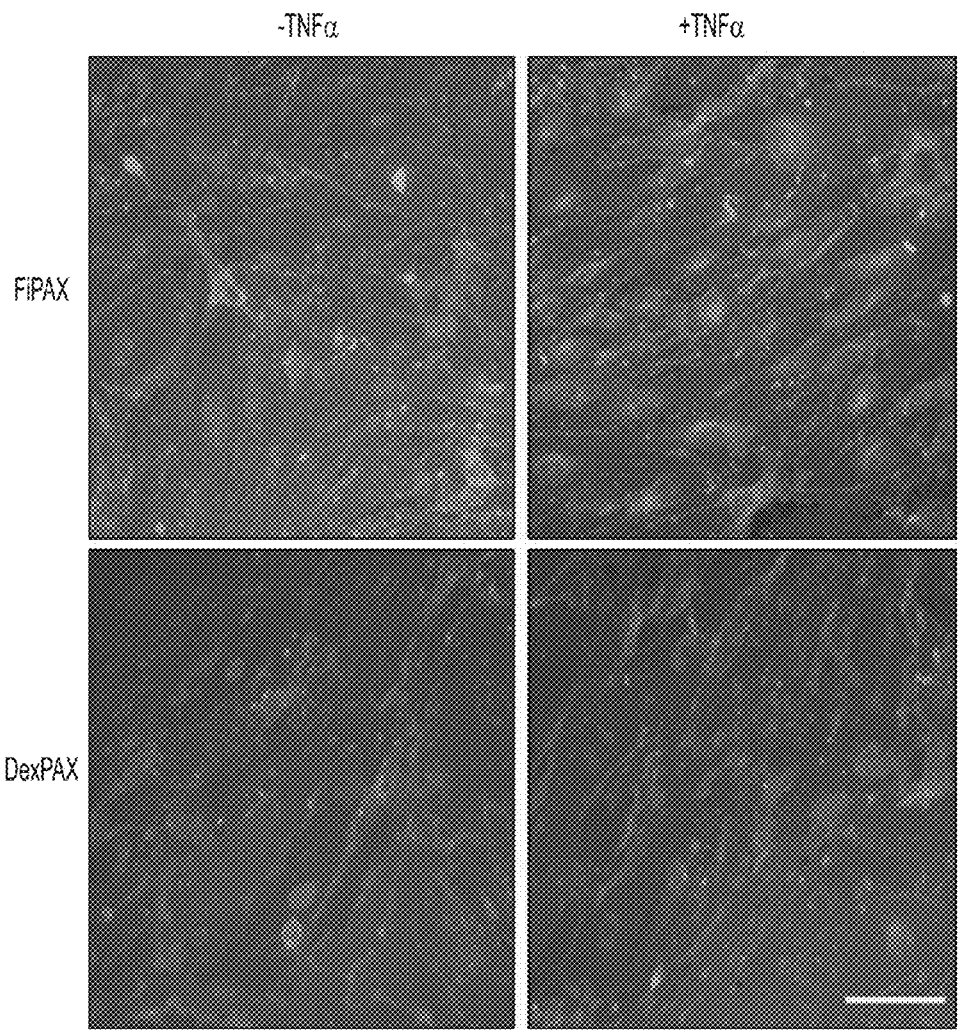
Figure 14D:
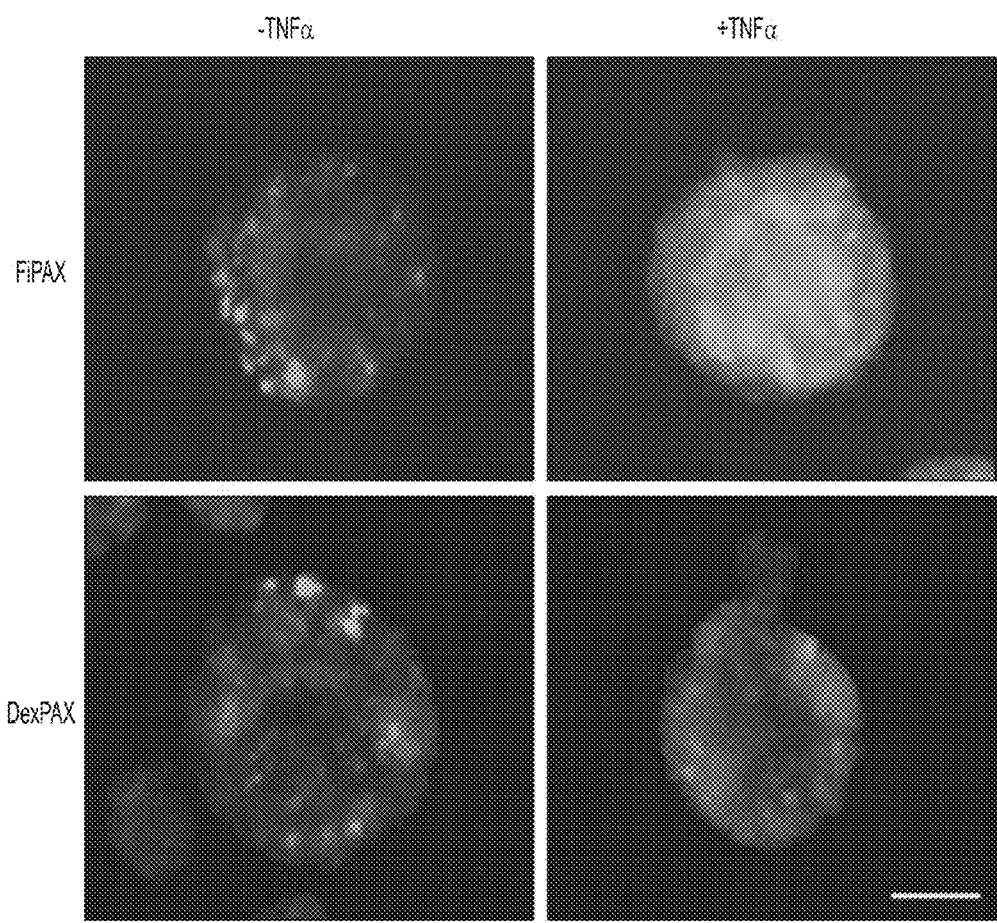
Figure 14E:
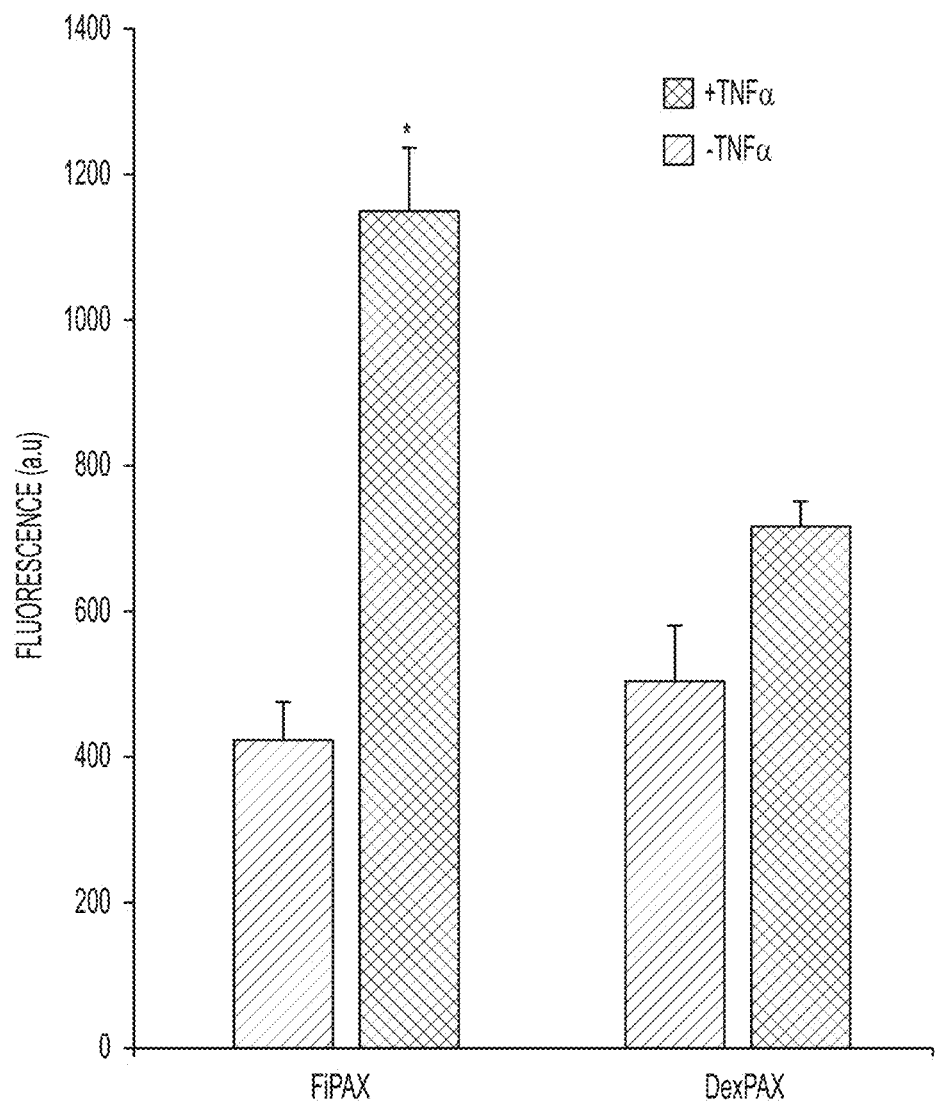

It was investigated whether a fucoidan-based nanoparticle would bind to activated endothelium and translocate the endothelial barrier. The ability of fucoidan nanoparticles to penetrate through endothelium and into tumor tissue was assessed using a modified Transwell assay. Murine brain endothelial (bEnd.3) cells were grown on the top chamber's membrane, and P-selectin expressing tumor spheroids were grown in the bottom chamber (FIG. 14A). The penetration of the nanoparticles through the bEnd.3 monolayer upon activation by TNF-α was measured. The quantity of FiPAX nanoparticles recovered from the bottom chamber increased significantly by ~30% (FIG. 14B) in the presence of TNF-α, while DexPAX increased by 15%, suggesting that endothelial activation enhanced the translocation of the FiPAX nanoparticles. The FiPAX nanoparticles were taken up by the endothelial cells only upon activating with TNF-α, and the cells did not take up the control DexPAX nanoparticle in either case (FIG. 14C). Penetration of the nanoparticles into tumor spheres via fluorescence microscopy was quantified. As shown in FIGS. 2D to 2E, a 3-fold increase in the FiPAX-encapsulated dye fluorescence in the tumor spheres upon activation with TNF-α, as well as greater penetration into the spheres, compared to the DexPAX nanoparticles (FIGS. 14D-14E). These observations suggest that endothelial activation mediates increased transport of P-selectin-targeted nanoparticles across an endothelial barrier and into solid tumor tissue compared to untargeted particles. These findings support that particle extravasation and tumor penetration to P-selectin expressing tumors in vivo is possible.

Figure 15A:
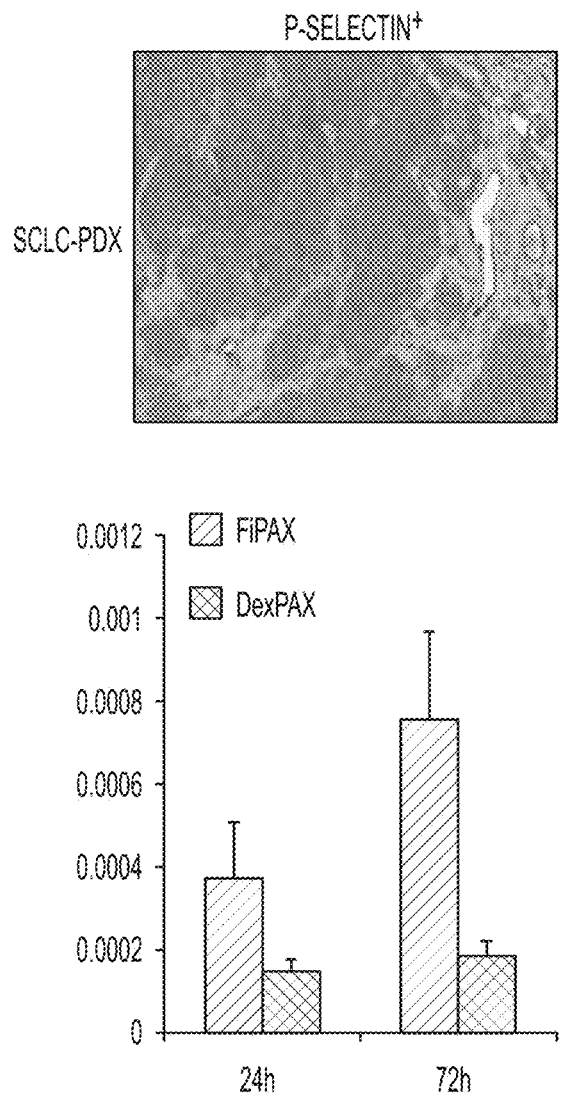
FIGS. 15A-15F illustrate targeting P-selectin positive and negative tumors in-vivo.
Figure 15B:
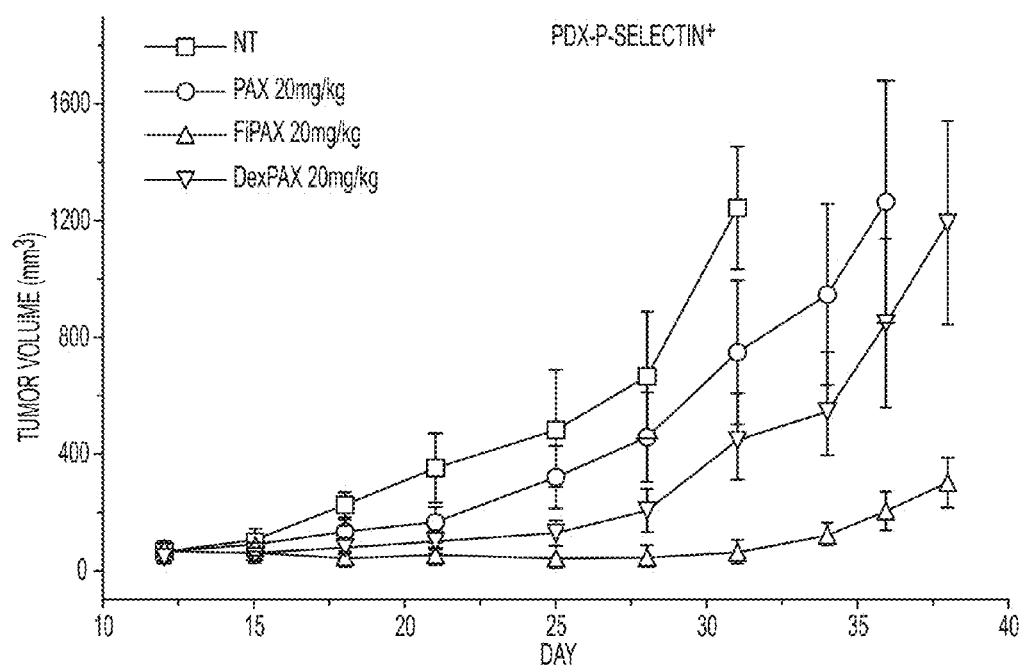
Figure 16A:
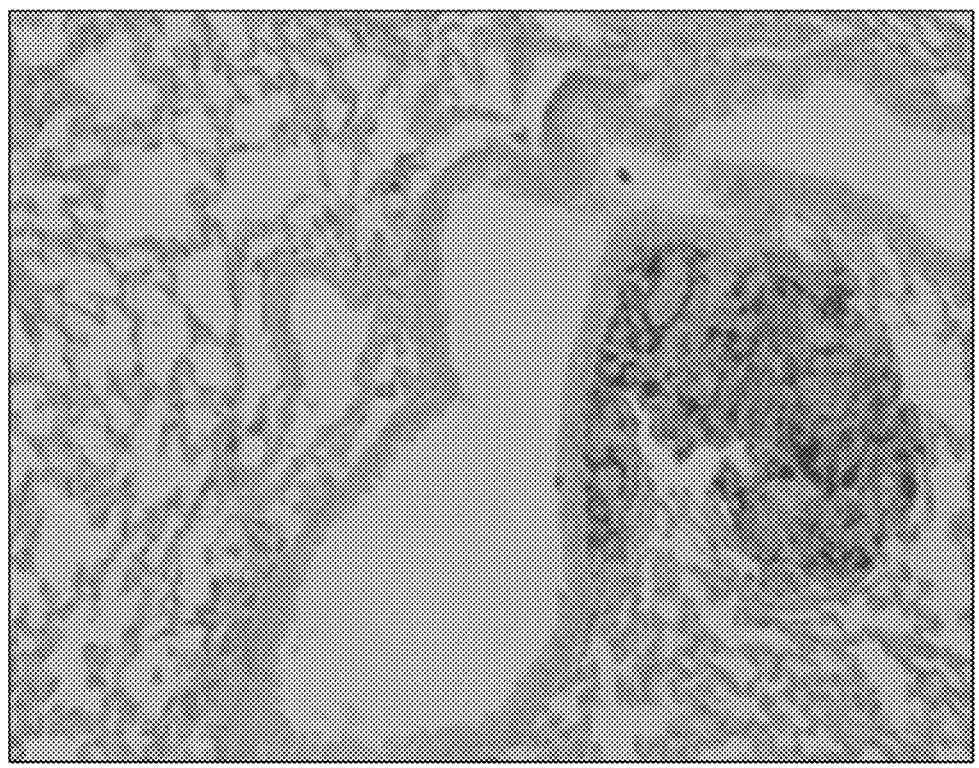
FIGS. 16A-16D illustrate FiDOX efficacy in lung metastasis, P-selectin expression, and Bio distribution of FiDOX.
Figure 16B:
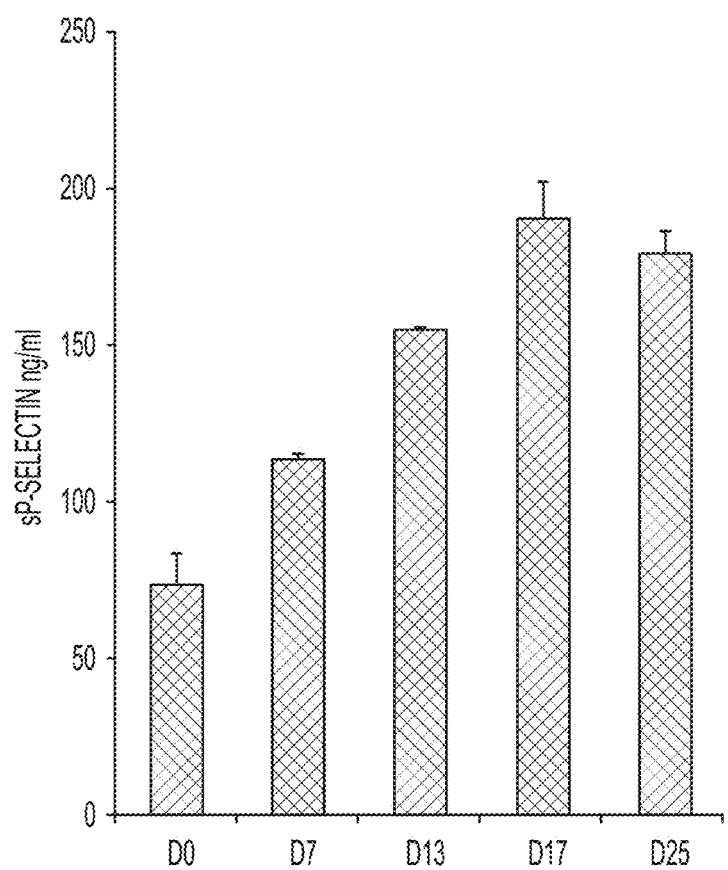
Figure 16C:
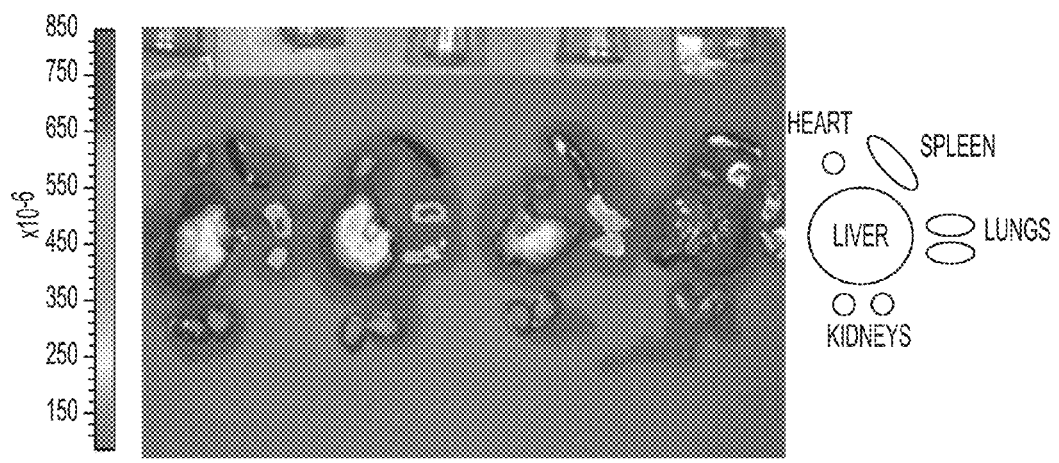

Anti-Tumor Efficacy Mediated by P-Selectin:

To determine the net efficacy of P-selectin targeting in vivo, a patient-derived xenograft (PDX) model of SCLC which expresses P-selectin was used (FIG. 15A). This PDX expressed P-selectin both in tumor endothelium and cancer cells (FIG. 13A: LX36). When tumors reached 70 mm³, mice were randomized into 4 arms: PBS, FiPAX, DexPAX and paclitaxel (PAX). Upon 24 h and 72 h after injection of nanoparticles, the mice were imaged to compare particle localization. The average fluorescence intensity was 2.5 times higher than that of DexPAX after 24 h, and the signal difference increased to 4.1 times at 72 h (FIG. 15A, FIG. 16B). Upon administration of a single injection of each treatment, FiPAX nanoparticles significantly inhibited tumor progression as compared to free paclitaxel or untargeted DexPAX nanoparticles (FIG. 15B).

Figure 15C:
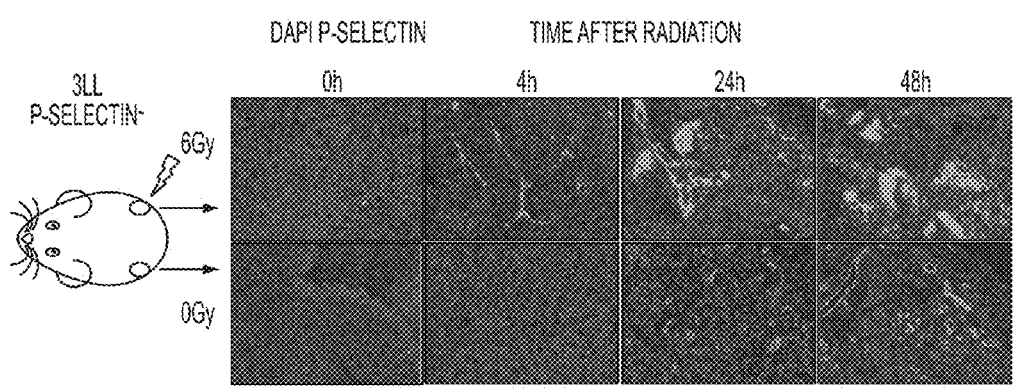
Figure 15D:
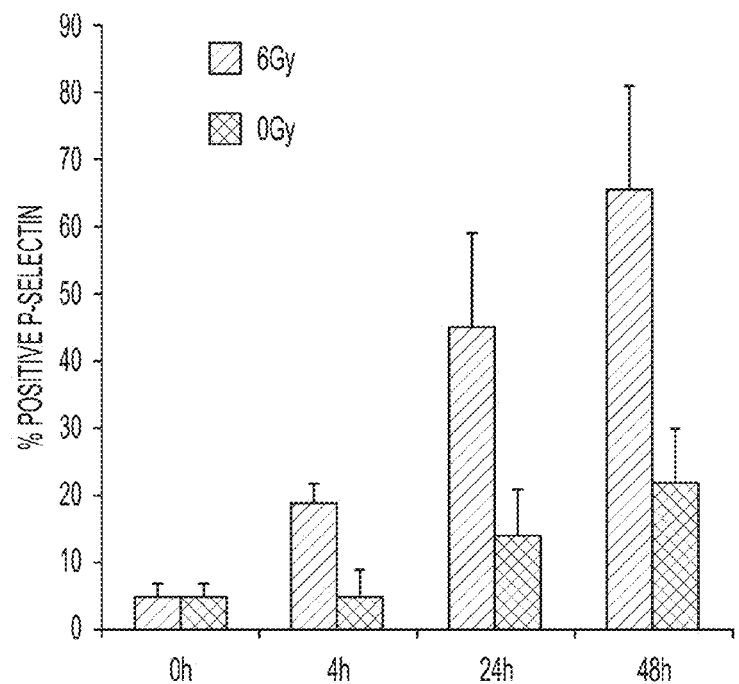

To investigate the radiation-induced expression of P-selectin in a model that does not spontaneously express the target, nude mice were inoculated in both flanks with Lewis lung carcinoma (3LL) cells. The resulting tumor did not endogenously express P-selectin, as observed by tissue staining (FIG. 15C). The right flank tumor of each mouse was irradiated with 6 Gy, while the left tumors were left un-irradiated. It was observed that the expression of P-selectin in the irradiated tumor was apparent by 4 hours and increased substantially by 24 hours (FIG. 15C). Notably, P-selectin expression was found in the non-irradiated tumors of the irradiated mice after a 24 hour delay (FIG. 15C), as well as an increase in soluble P-selectin (sP-selectin) in the blood of the irradiated mice (FIGS. 16A-16D).

Figure 15E:
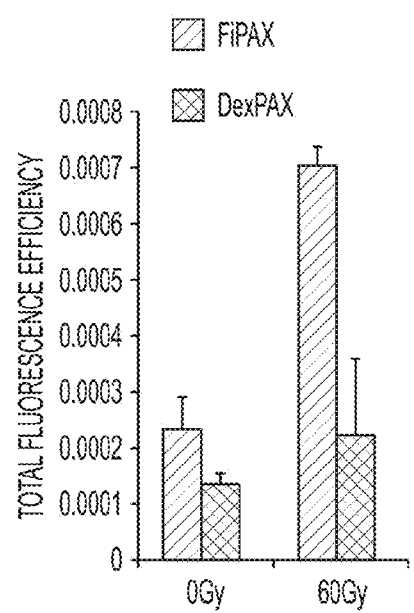
Figure 15F:
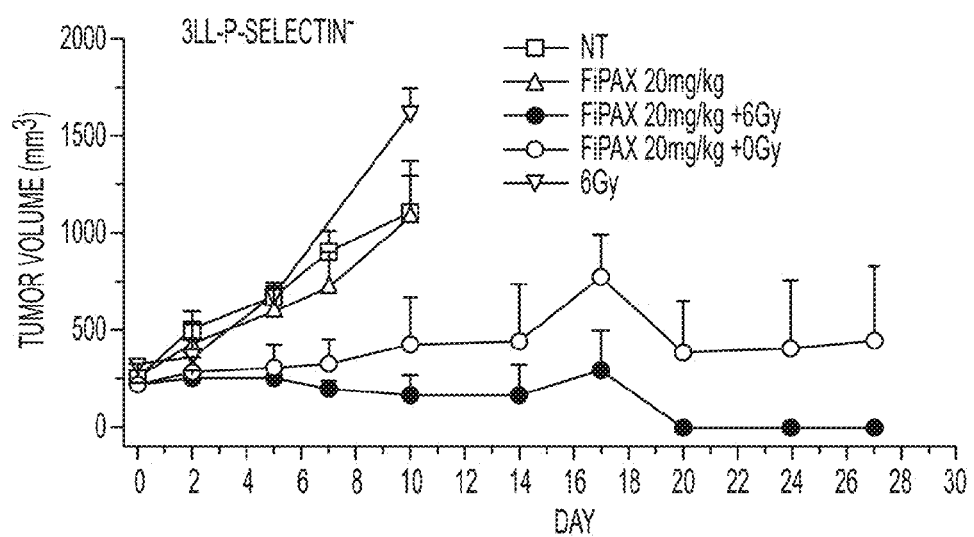
Figure 16D:
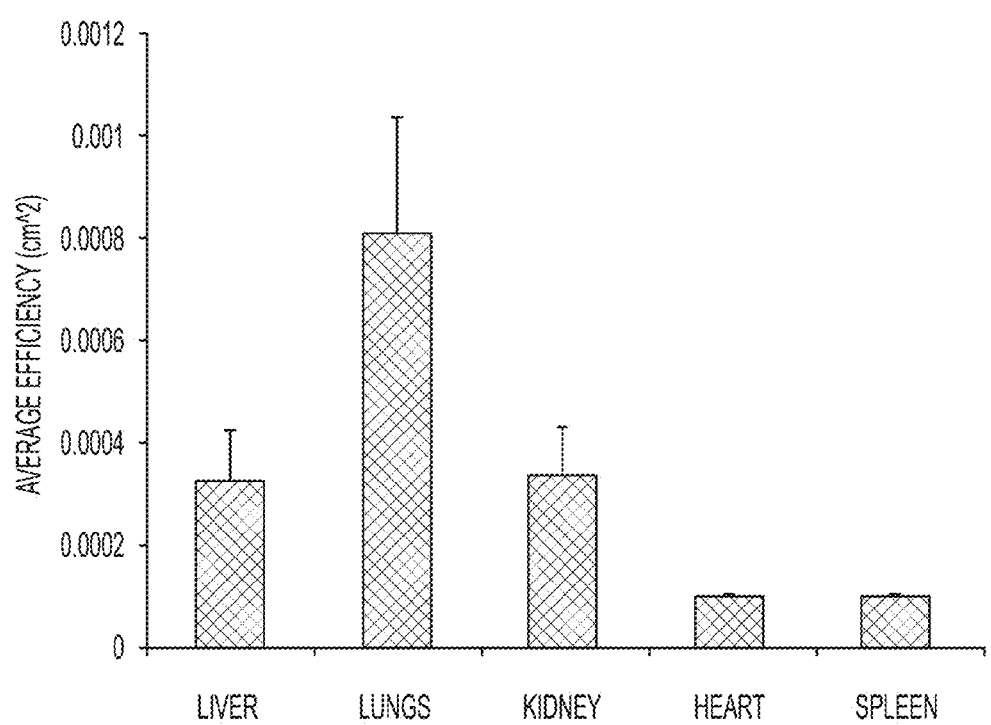

It was investigated whether radiation could selectively guide P-selectin-targeted drug carrier nanoparticles to a tumor site to result in a net therapeutic benefit. The 3LL bilateral tumor model was irradiated with 6 Gy on the right tumor before injecting the mice i.v. with nanoparticles 4 hours later. To distinguish the effects of radiation-induced P-selectin targeting from an EPR effect or non-induced P-selectin, untargeted DexPAX nanoparticles and non-irradiated control mice were included. At 24 hours after treatment, the fluorescence signal from FiPAX nanoparticles were 3.8 times higher in the irradiated tumors over non-irradiated tumors, while there was no difference in the DexPAX-treated mice (FIG. 15E, 16D). Growth was halted in tumors receiving both radiation and FiPAX nanoparticles, resulting in their complete tumor disappearance (FIG. 15F). Notably, in mice treated with FiPAX nanoparticles and radiation, significant inhibition was observed in the non-irradiated tumors, suggesting an abscopal-like effect on anti-tumor efficacy mediated by the nanoparticle. To corroborate the in vivo observations, FiPAX binding to radiation-induced P-selectin expression in vitro were evaluated. In bEnd.3 endothelial cells, radiation-mediated P-selectin expression was observed in a dose-dependent manner. The irradiated cells took up FiPAX nanoparticles, while little uptake of DexPAX nanoparticles was measured (FIGS. 16A and 16B: P<0.05).

Figure 17A:
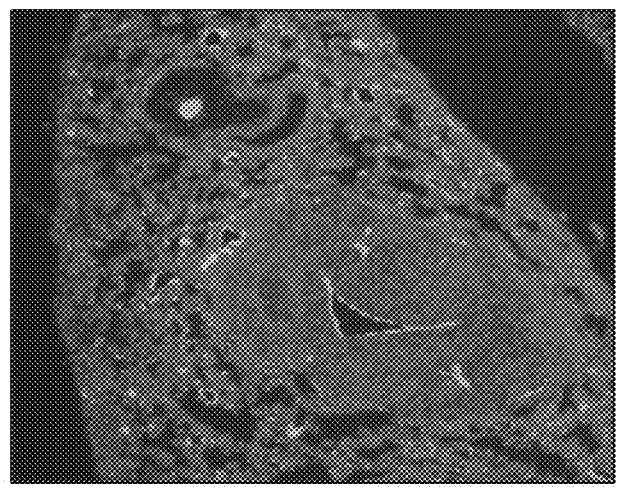
FIGS. 17A-17E illustrate the efficacy of P-selectin targeted nanoparticles in metastases.
Figure 17A:
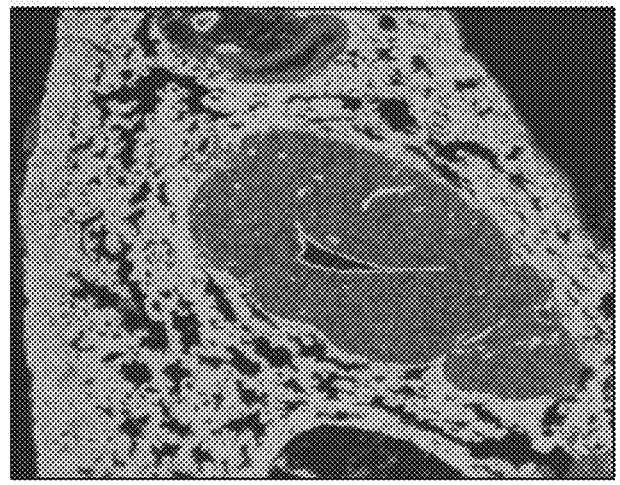
Figure 17B:
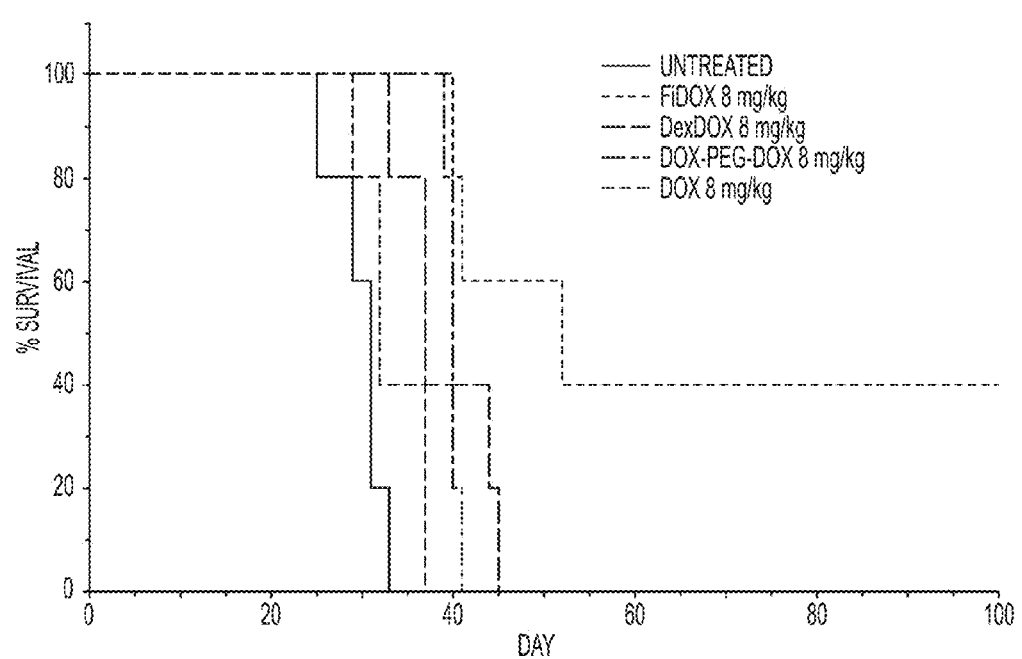
Figure 17C:
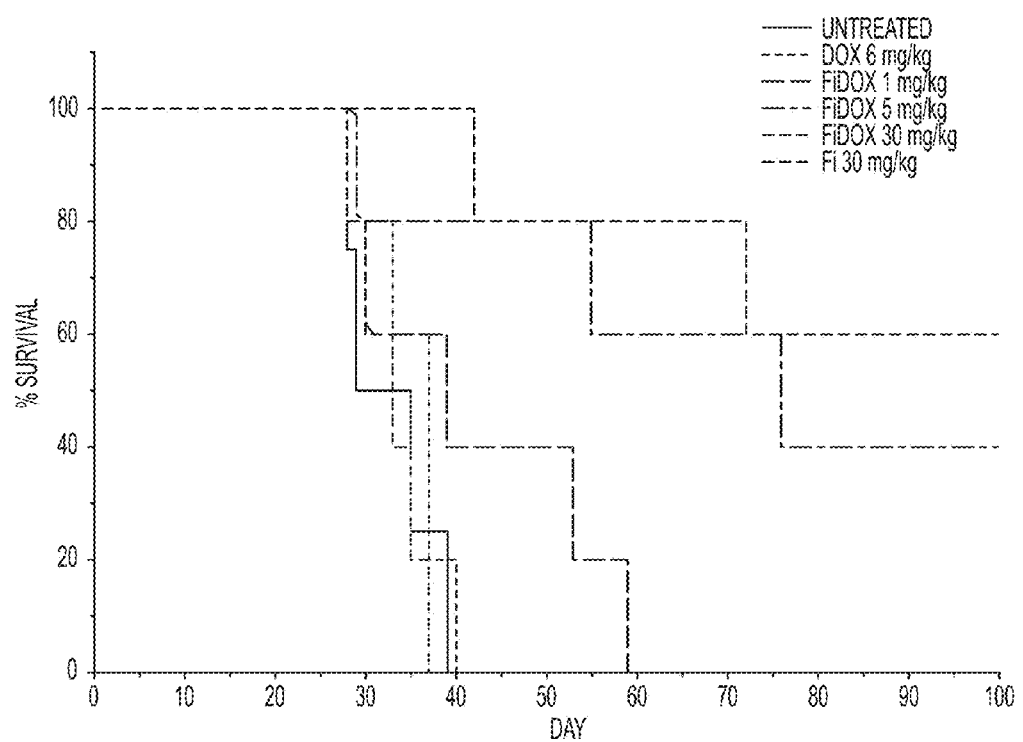
Figure 17D:
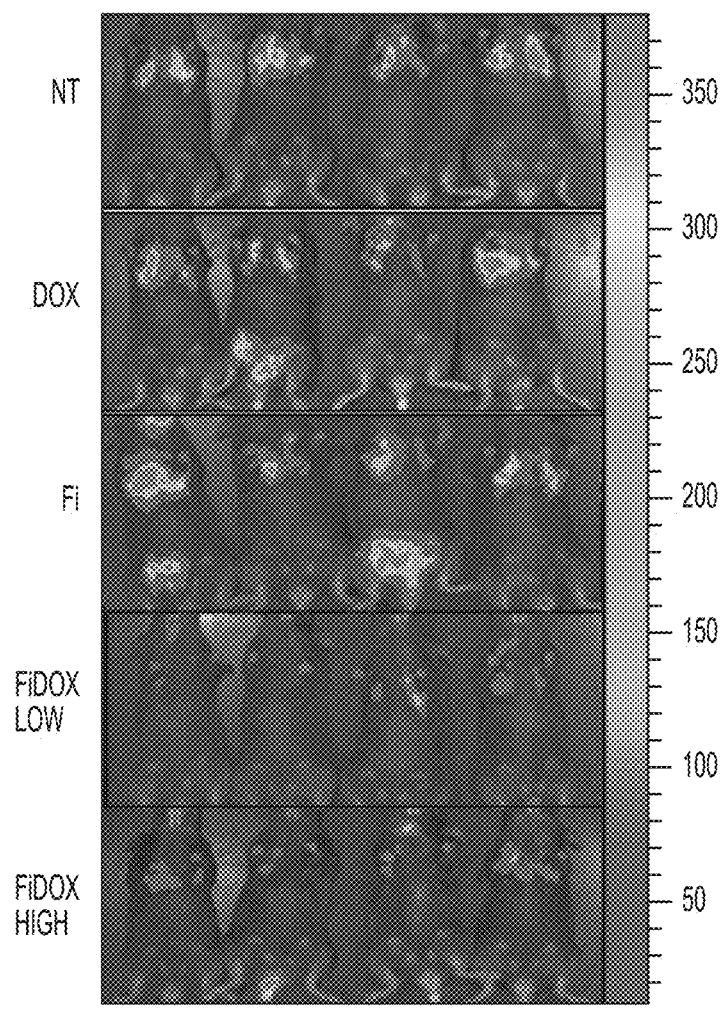
Figure 17E:
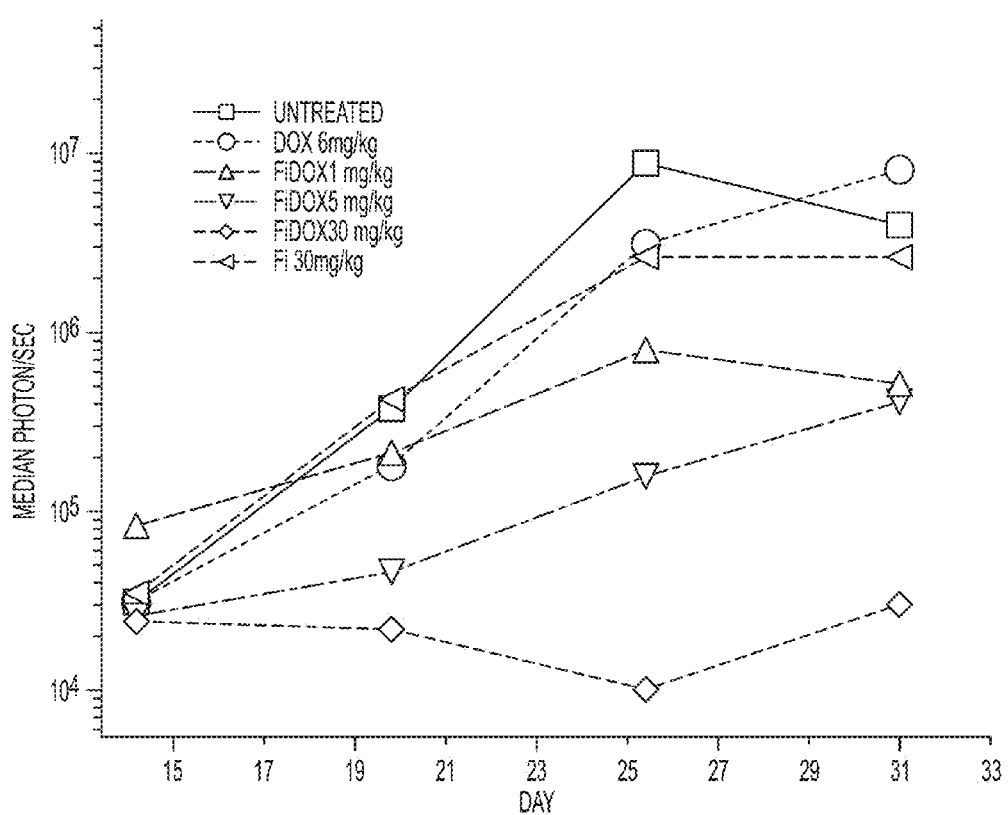
Figure 18A:
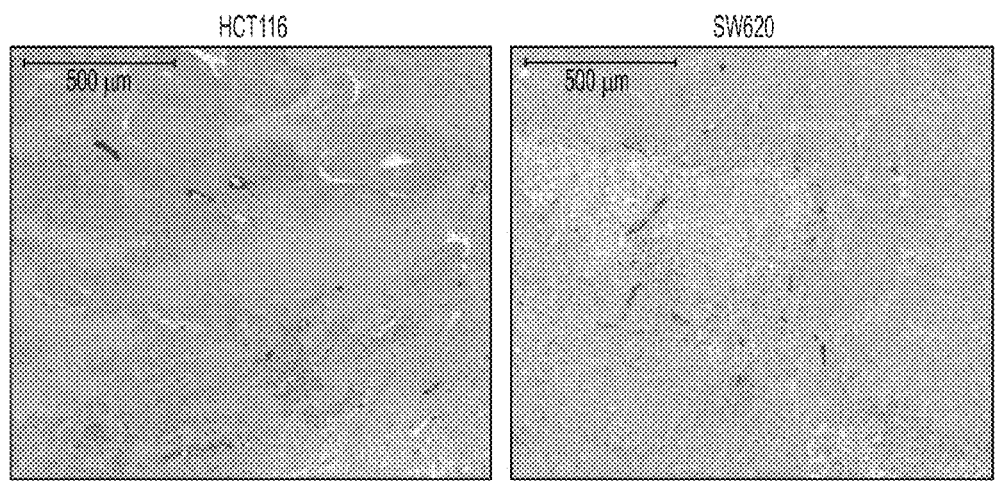
FIGS. 18A-18E illustrate FiMEK improved pERK inhibition and efficacy.
Figure 18B:
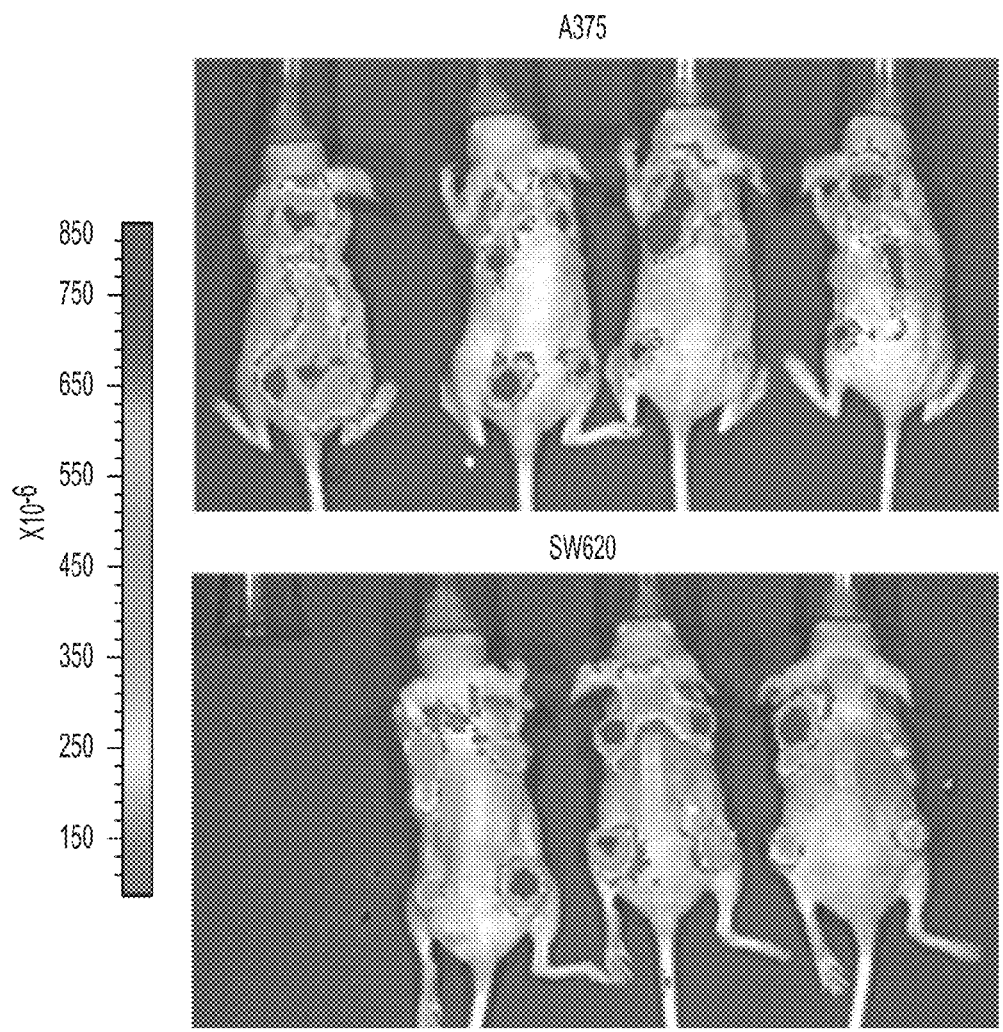
Figure 18C:
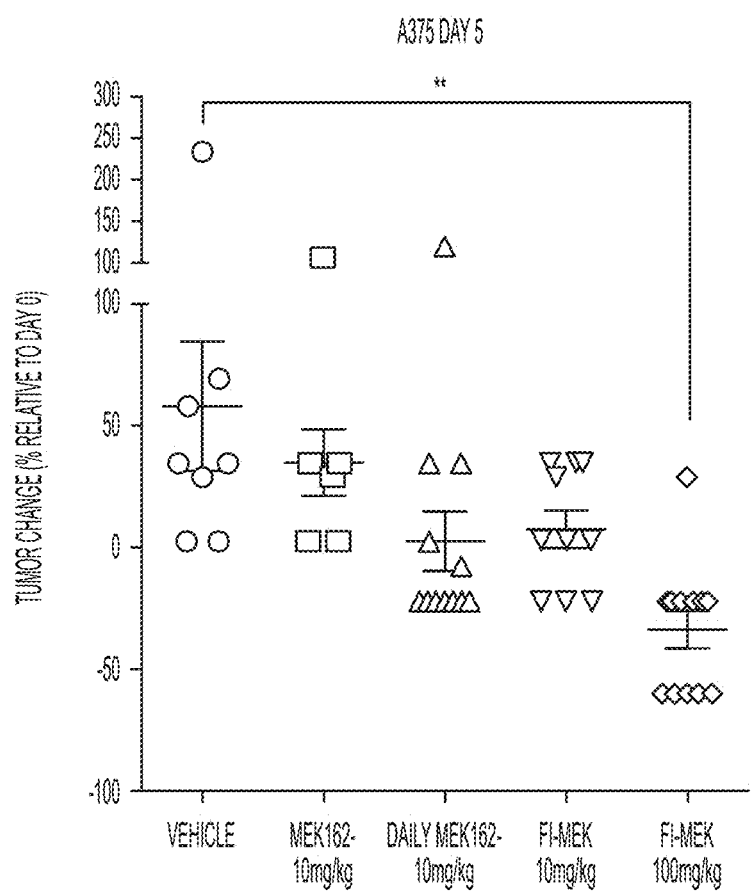
Figure 18D:
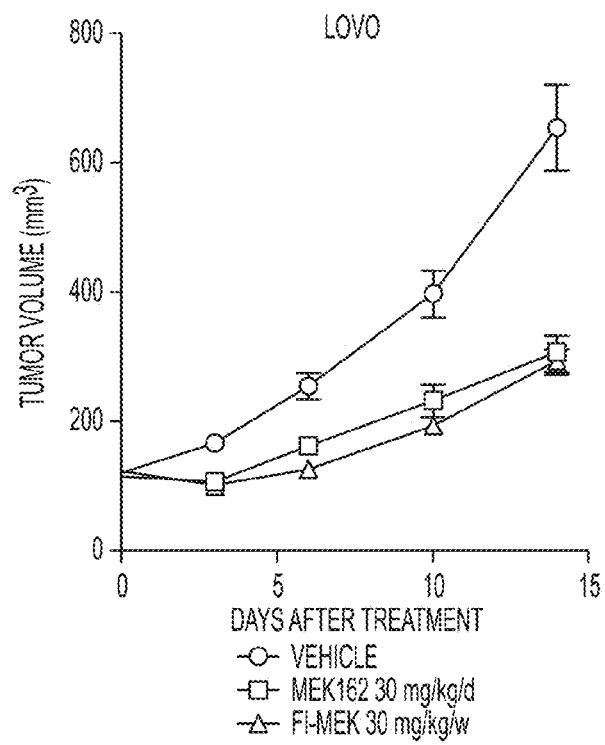
Figure 18D:
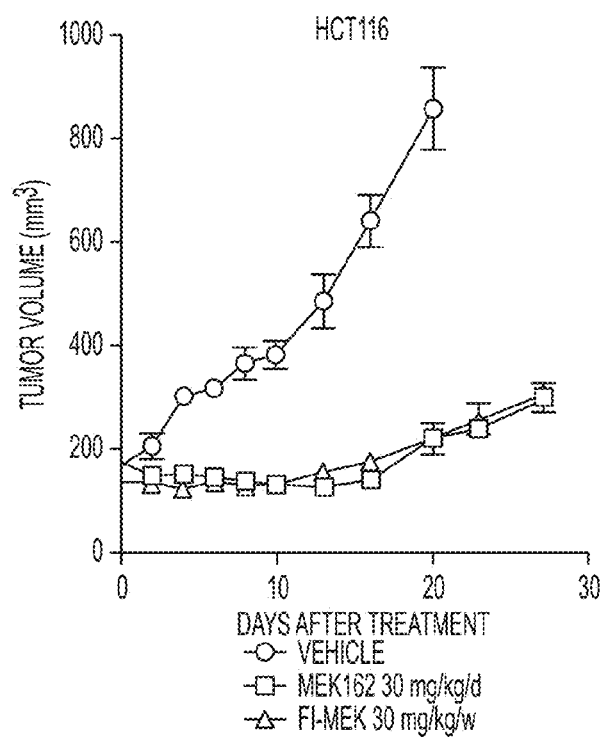
Figure 18E:
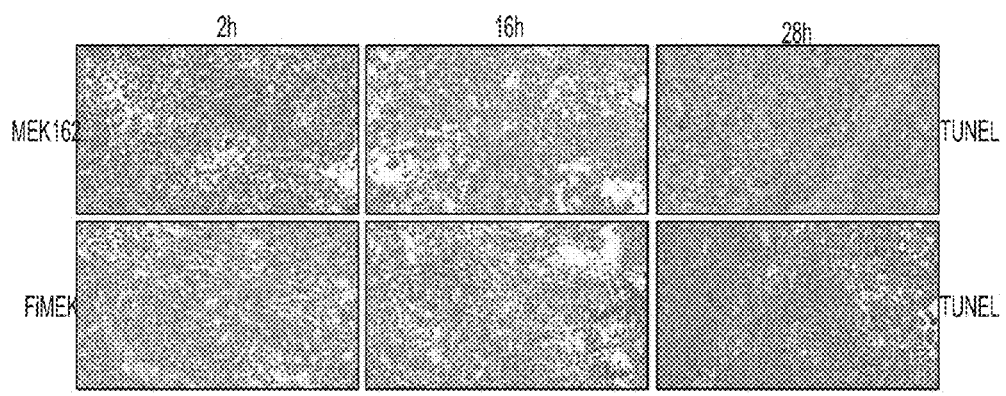

Anti-Tumor Efficacy in Endogenous P-Selectin Expressing Metastases:

The anti-tumor efficacy of P-selectin-targeted drug carrier nanoparticles was assessed against an aggressive experimental metastasis model. The i.v. injection of 10' B16F10 melanoma cells results in lung metastases which exhibit P-selectin expression in the associated vasculature (FIG. 17A-B). Three different doses of FiDOX (fucoidan-encapsulated doxorubicin) nanoparticles were then administered to identify a therapeutic window. The mice were divided into 6 groups of 5 mice and treated with a single dose of either free doxorubicin at 6 mg/kg or 8 mg/kg, close to the maximum tolerated dose, fucoidan (30 mg/kg), as a vehicle control, and three concentrations of Fi DOX (1 mg/kg, 5 mg/kg and 30 mg/kg). The treatment with Fi DOX nanoparticles at all three concentrations resulted in decreased tumor burden and prolonged survival upon a single injection, whereas an equivalent amount of free doxorubicin at its maximum tolerated dose, did not have a significant effect (FIG. 17C). Fucoidan alone also showed no survival benefit. After 7 days post-treatment, tumor bioluminescence shows a clear reduction in median photon count in the medium and the high dose groups (FIG. 17D, 17E). Signs of toxicity as measured by weight loss or complete blood count were not observed (FIGS. 18A-18E). The anti-tumor efficacy of FiDOX nanoparticles was also compared to the untargeted DexDOX nanoparticle control and untargeted drug-polymer conjugate, DOX-PEG-DOX at equivalent doxorubicin doses of 8 mg/kg. The mean survival of the FiDOX group was significantly higher at 68.8 days with 400 cured mice compared to DexDOX at 40.2 days with no cures, DOX-PEG-DOX at 39.2 days, and untreated 32.4 at days (FIG. 17B, p=0.005).

P-Selecting Targeting of Mechanistically Targeted Drugs:

The Ras-ERK pathway is frequently hyperactive in substantial types of cancers including melanoma, colorectal, and lung cancers, and therefores MEK/ERK reversible inhibitors have been tested in large number of clinical trials in RAS- and BRAF-mutated cancers. Blocking this pathway using systemic MEK/ERK inhibitors is, however, dose-limiting with only temporal target inhibition. At high dosage, these treatments cause toxicity in patients such as severe rash and chronic serous retinoscopy (CSR).

It is described herein how P-selectin-targeted delivery improved the efficacy of reversible kinase inhibitors which are specific to cancer cells. For example, the delivery of MEK inhibitor to the tumor microenvironment using P-selectin targeted nanoparticles increased the concentration of drug in the tumor itself, therefore prolonging the duration of inhibition and reduce systemic toxicity.

Figure 19A:
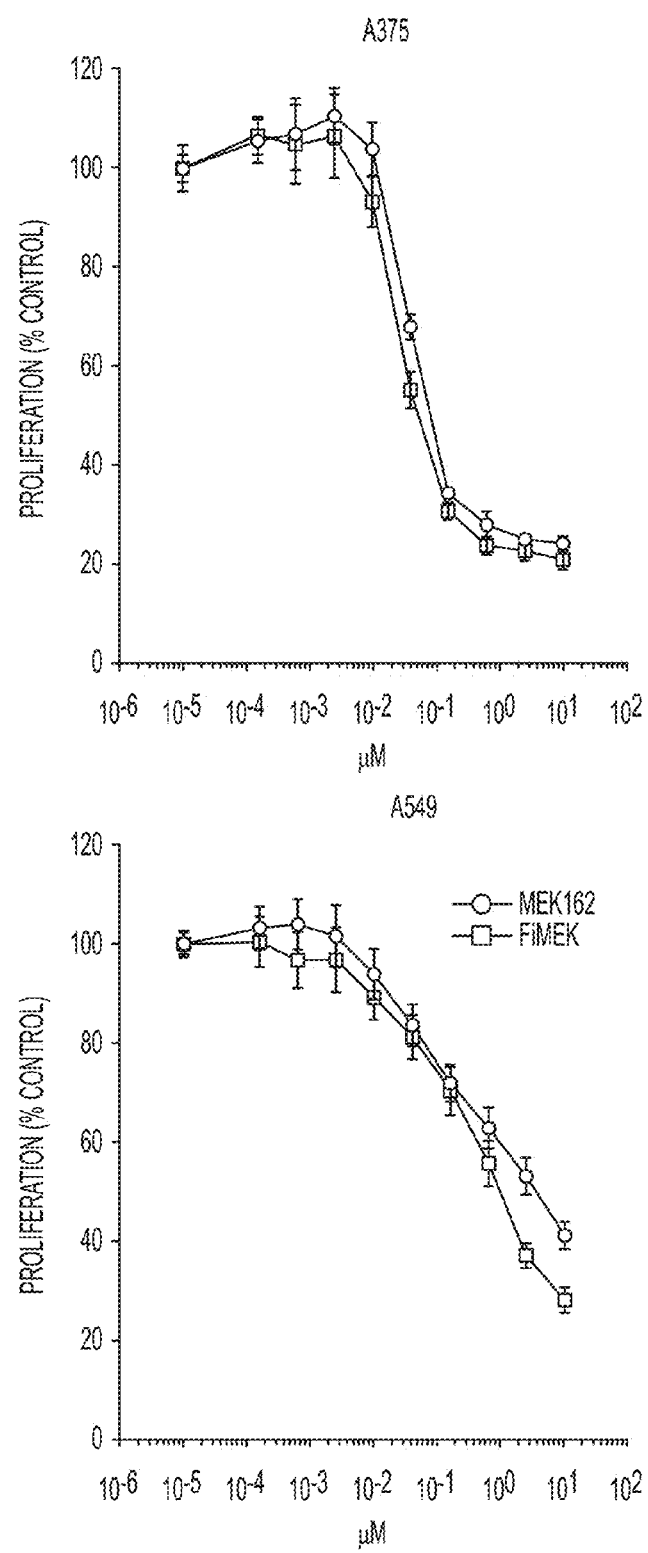
FIGS. 19A-19D illustrate inhibition of MEK improved anti-tumor efficacy and induced apoptosis by P-selectin targeted nanoparticles in vitro and in vivo.
Figure 19B:
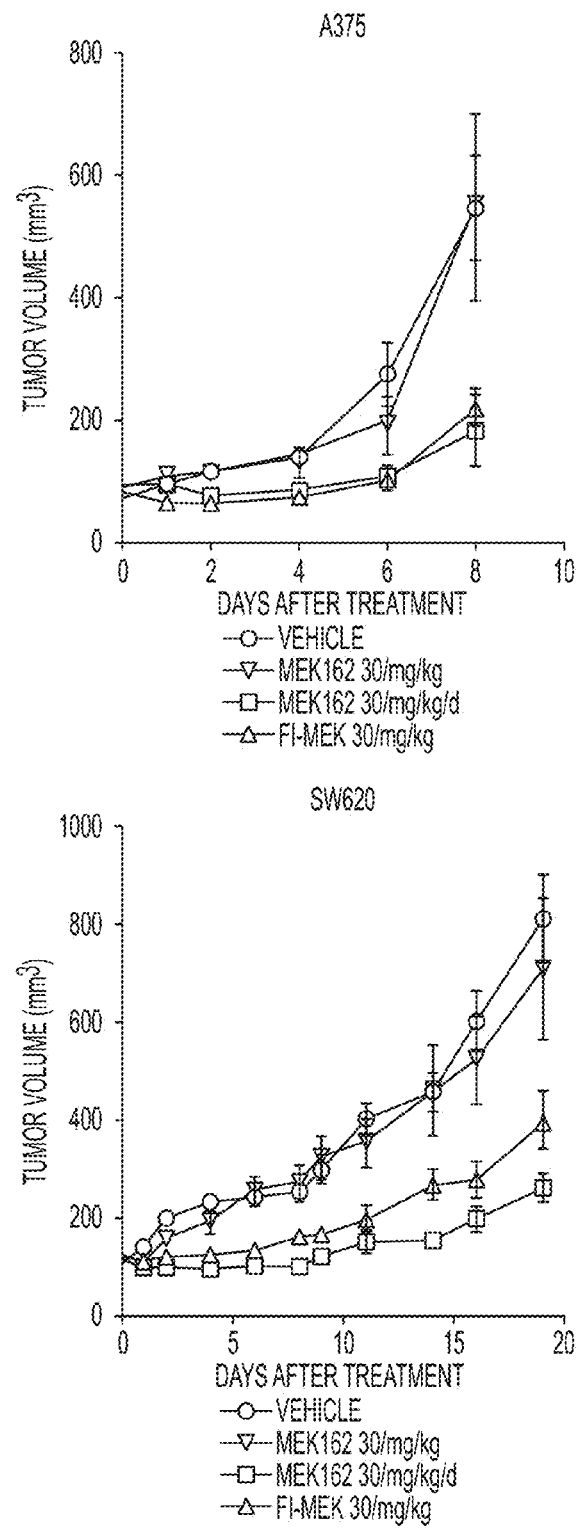
Figure 21:
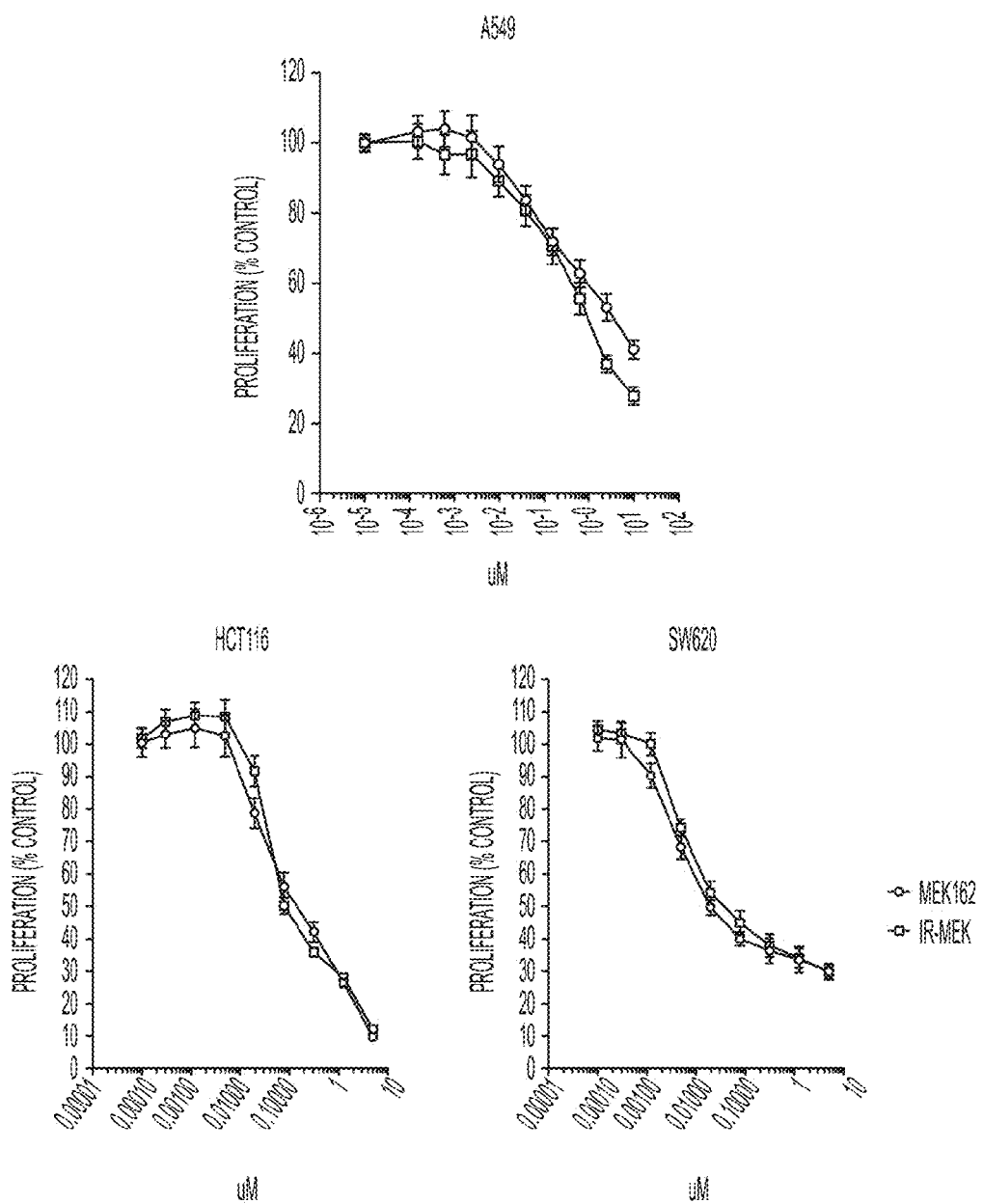
FIG. 21 shows proliferation of cell lines was measured after 4 days of treatment with MEK162 or FI-MEK as indicated. Open circle-MEK162, Open Square-FiMEK.
Figure 23A:
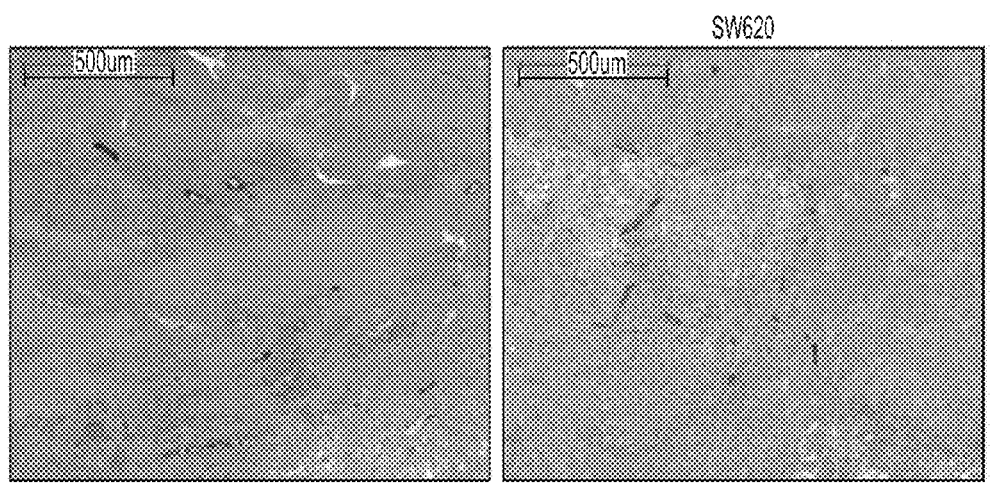
FIG. 23A shows IHC staining of P-selectin expression in MEK162 sensitive HCT116 and SW620 xenografts.
Figure 23B:
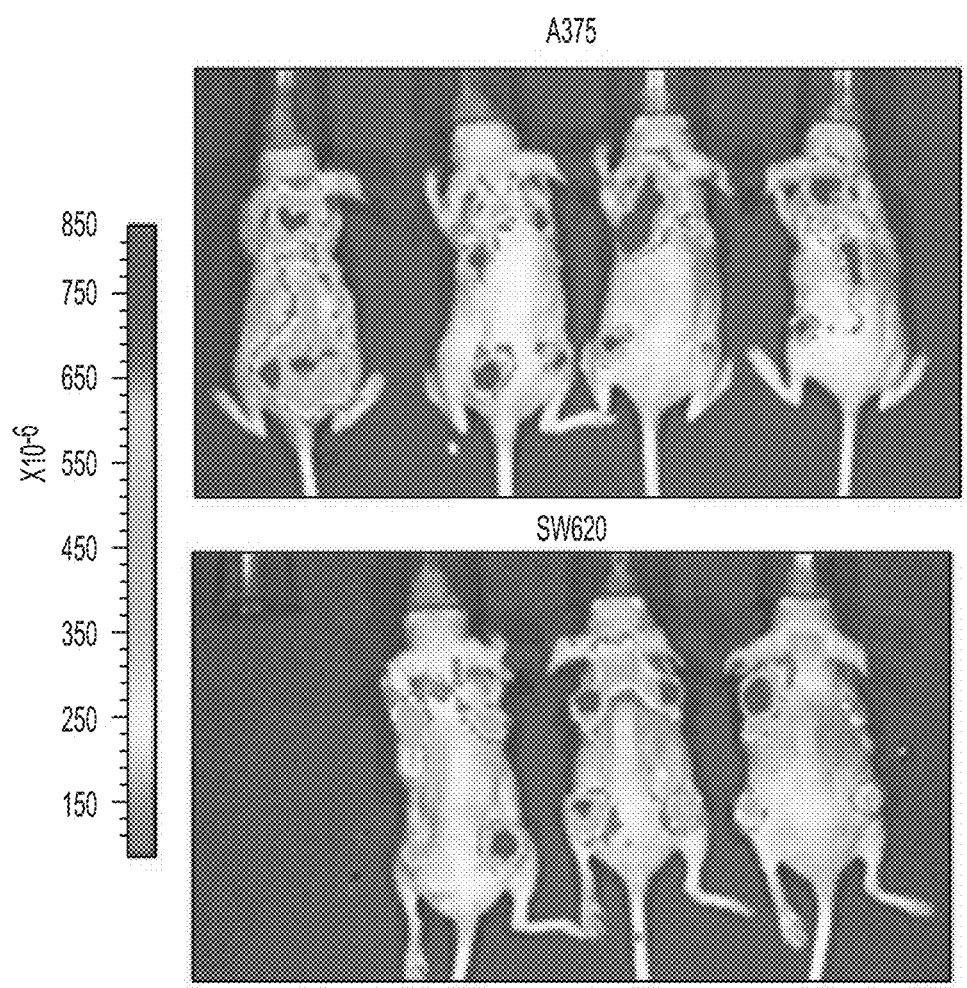
FIG. 23B shows whole body imaging of FiMEK nanoparticles in A375 and SW620 xenografts 24 h post administration.
Figure 23C:
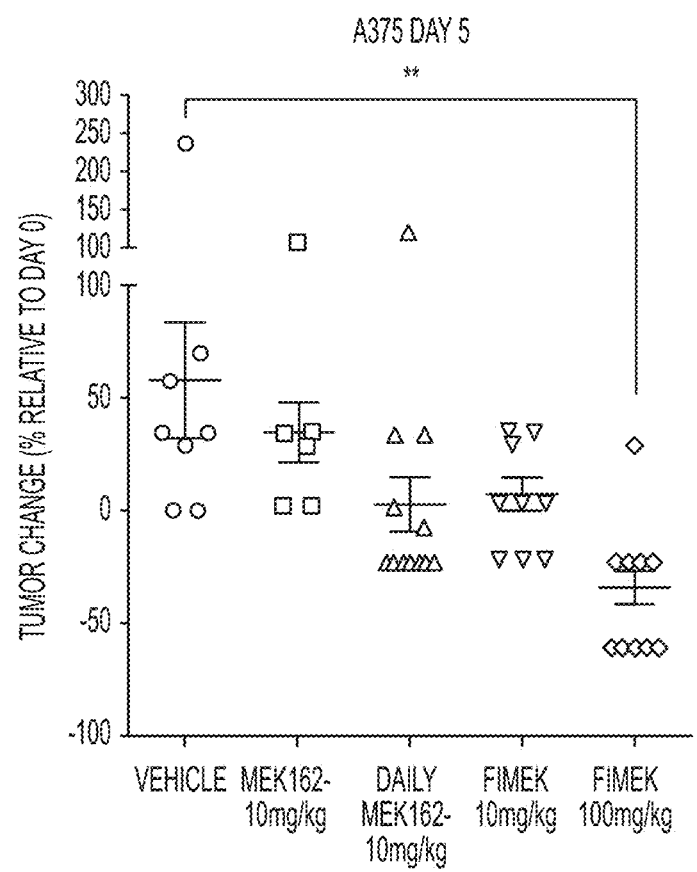
FIG. 23C shows percentage % of tumor size change as calculated from day 0.
Figure 23D:
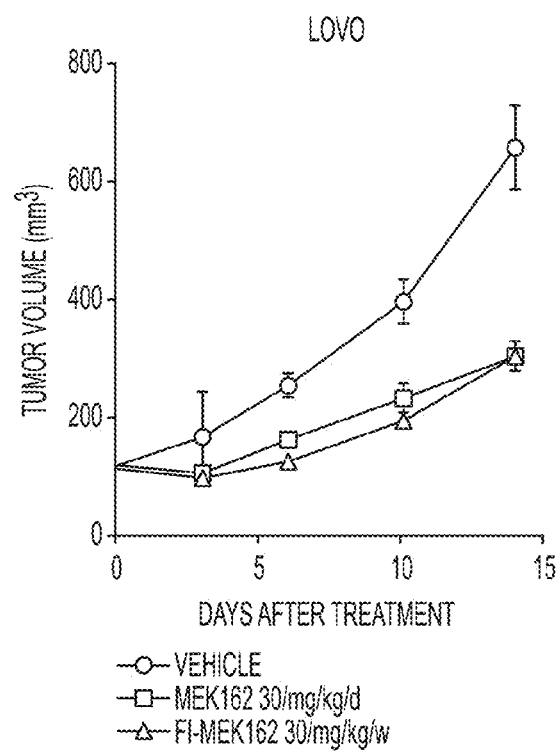
FIG. 23D shows growth inhibition of different regiments.
Figure 23D:
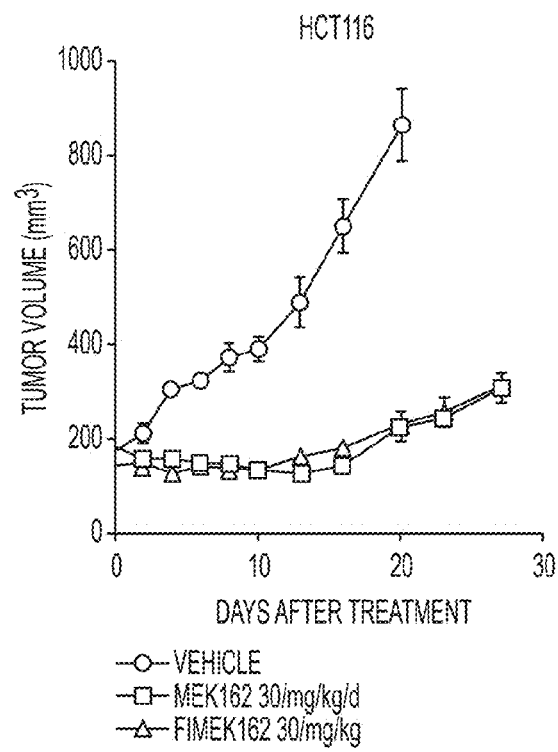
Figure 23E:
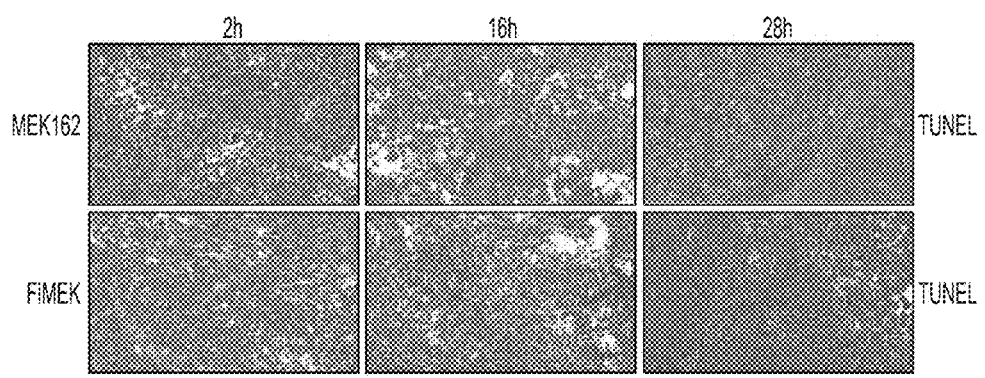
FIG. 23E shows evaluation of apoptosis after single administration of MEK162 or FiMEK.

To this end, MEK162 was co-encapsulated with IR783 within fucoidan-based nano-particles (FiMEK) in the same manner that FiPAX was prepared. In vitro, the release of the MEK162 by the nano-particle was sustained with maximum of 85% reached in 24 hours and accelerated by acidic pH (FIG. 23A). Data shows that free MEK162 and MEK162 loaded fucoidan nanoparticles (FI-MEK) had similar biochemical and anti-tumor activity against BRAF mutated melanoma (A375), and NRAS mutated lung (A549) and KRAS mutated colorectal (HCT116 and SW620) cancer cells in vitro (FIG. 19A, FIG. 21).

In tumor bearing mice, a single administration of FIMEK induced significant tumor growth inhibition compared to no effect of oral treatment. A375 and SW620 tumor bearing mice were treated with a weekly dose of MEK162, FiMEK and a daily dose of free MEK162. It was observed that a weekly dose of FiMEK was more effective than a weekly dose of free MEK, and had comparable efficacy with a daily administration. This result was validated in two other models of LOVO and HCT116 xenografts (FIGS. 23A-23E).

Figure 19C:
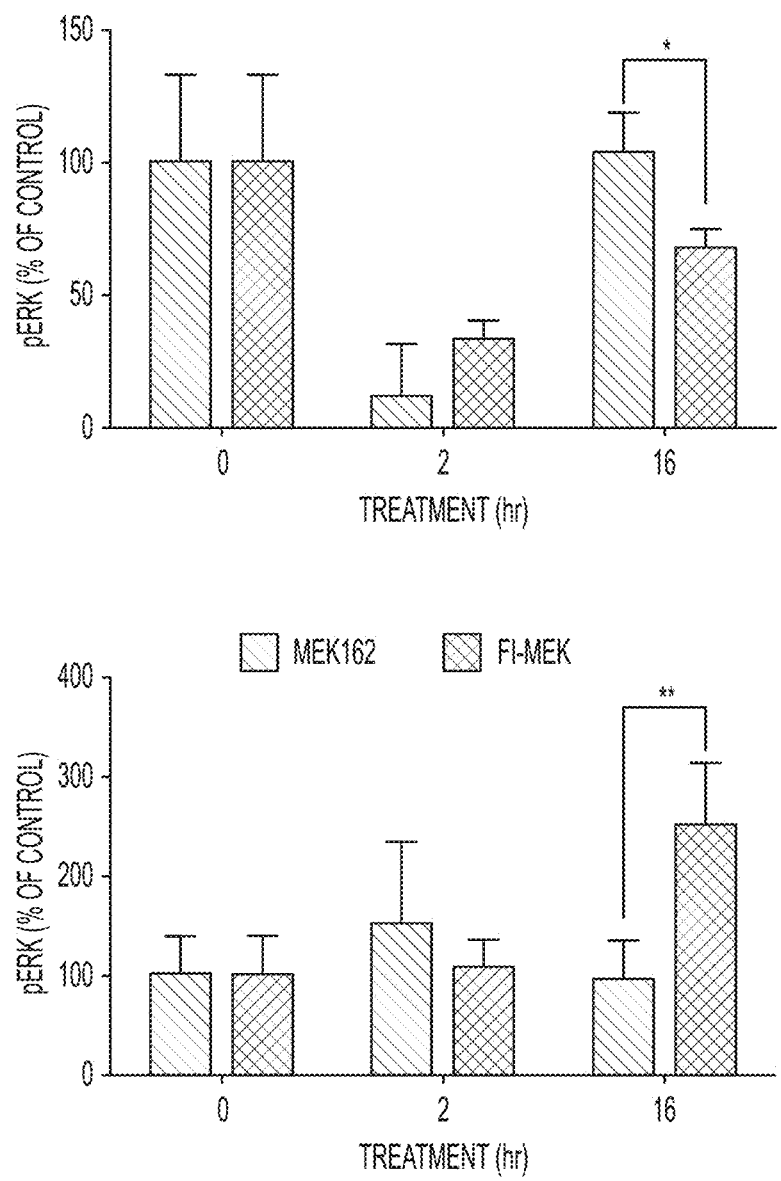
Figure 19D:
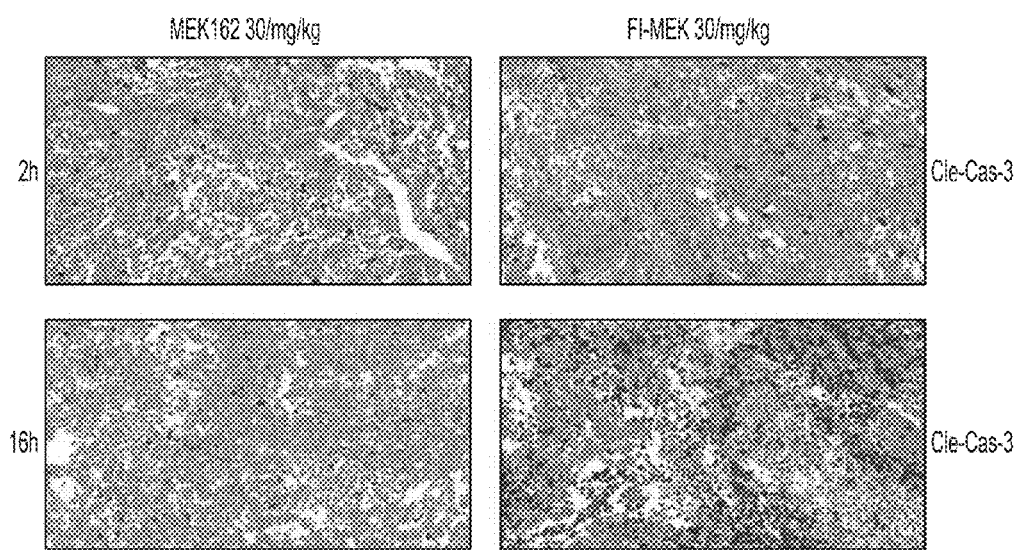
Figure 22:
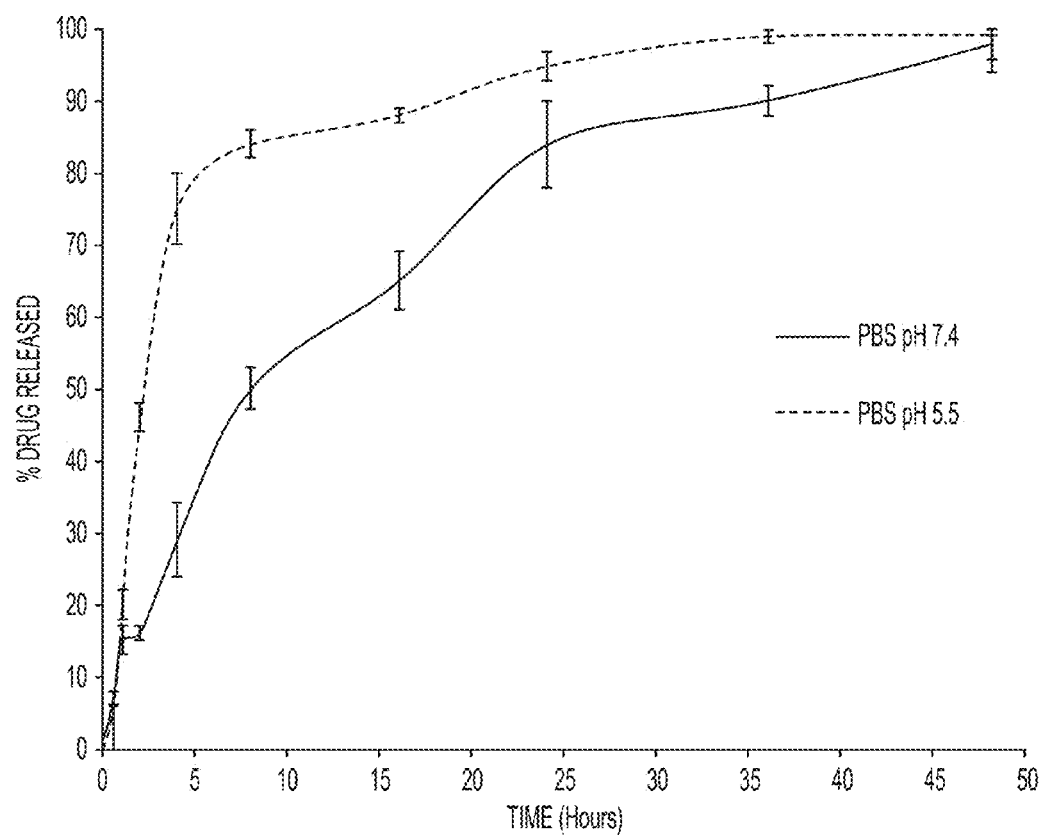
FIG. 22 shows the drug release profile MEK162 drug from nanoparticles over time at different pH.

To further understand the enhanced efficacy of FiMEK compared to oral MEK162, the pharmacodynamics were assessed by measuring the levels of pERK and cleavage of PARP on tumors treated with MEK162 or FiMEK at 2 h and 16 h after administration (FIG. 19C). The data shows a similar inhibition of pERK after 2 hours of treatment. However, significant prolong of pERK inhibition was observed in mice treated with FIMEK when compared to mice treated with oral MEK162. An association between prolong inhibition of ERK and induction of apoptosis was observed, indicating the importance of the duration of pathway inhibition. Immunohistochemistry of Clevage PARP on xenogfrat HCT116 tumors treated with MEK162 or MEK-IR was assessed to confirm the death of tumor cells (FIG. 19D, 19E). FIG. 22 shows the drug release profile MEK162 from nanoparticles over time at different pH.

What is claimed is:

1. A polymeric nanoparticle with affinity to P-selectin, the nanoparticle comprising
   a non-covalent assembly of:
   (i) a sulfated polymer species comprising free hydroxyl moieties and free sulfate moieties capable of targeting P-selectin; and
   (ii) a hydrophobic drug,
   wherein the nanoparticle has an average particle diameter of between about 20 and about 200 nm, and wherein the non-covalent assembly is a self-assembly of the sulfated polymer species around the hydrophobic drug.

2. The nanoparticle of claim 1, wherein the sulfated polymer species comprises one or more members selected from the group consisting of a sulfated polysaccharide, protein, and a fucoidan.

3. The nanoparticle of claim 1, wherein the sulfated polymer species comprises a fucoidan.

4. The nanoparticle of claim 1, wherein the hydrophobic drug comprises a member selected from the group consisting of paclitaxel, MEK162, docetaxel, Camptothecin, sorafenib, ispinesib, LY294002, Selumetinib, PD184352, 5-fluorouracil, Cyclophosphamide, Atorvastatin, Lovastatin, etoposide, dexamethasone, gemcitabine, Rapamycin (Sirolimus), and methotrexate.

5. The nanoparticle of claim 1, wherein the nanoparticle has an average particle diameter of from about 100 nm to about 200 nm.

6. The nanoparticle of claim 1, wherein the nanoparticle further comprises a fluorophore.

7. The nanoparticle of claim 6, wherein the fluorophore is a near infra-red dye.

8. The nanoparticle of claim 7, wherein the infra-red dye is IR783.

9. A method for manufacturing the nanoparticle of claim 1, the method comprising:
   contacting the hydrophobic drug to the sulfated polymer species to form a mixture; and
   agitating the mixture to form nanoparticles.

10. The method of claim 9, wherein agitating the mixture comprises sonicating the mixture.

11. The method of claim 9, wherein the hydrophobic drug and the sulfated polymer species are precipitated together.

12. The method of claim 9, wherein the hydrophobic drug and the sulfated polymer species are precipitated together via nano-precipitation.

13. The nanoparticle of claim 1, wherein the nanoparticle is negatively charged.

* * * * *